(12) United States Patent
Ahn et al.

(10) Patent No.: US 11,201,295 B2
(45) Date of Patent: Dec. 14, 2021

(54) HETEROCYCLIC COMPOUND AND ORGANIC LIGHT-EMITTING DEVICE INCLUDING THE SAME

(71) Applicant: SAMSUNG DISPLAY CO., LTD., Yongin-si (KR)

(72) Inventors: Heechoon Ahn, Yongin-si (KR); Soobyung Ko, Yongin-si (KR); Mieun Jun, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 188 days.

(21) Appl. No.: 15/642,399

(22) Filed: Jul. 6, 2017

(65) Prior Publication Data

US 2018/0040833 A1 Feb. 8, 2018

(30) Foreign Application Priority Data

Aug. 2, 2016 (KR) .................. 10-2016-0098448

(51) Int. Cl.
*H01L 51/00* (2006.01)
*C07D 401/10* (2006.01)
(Continued)

(52) U.S. Cl.
CPC ........ *H01L 51/0072* (2013.01); *C07D 401/04* (2013.01); *C07D 401/10* (2013.01);
(Continued)

(58) Field of Classification Search
None
See application file for complete search history.

(56) References Cited

U.S. PATENT DOCUMENTS 5,723,413 A * 3/1998 Bratz .................... A01N 43/90
504/245
8,722,208 B2 5/2014 Kai et al.
(Continued)

FOREIGN PATENT DOCUMENTS

CN 104449665 A * 3/2015
GB 1096049 * 12/1967
(Continued)

OTHER PUBLICATIONS

Machine English translation of Jeon et al. (KR 10-2014-0127702). Mar. 7, 2019.*
(Continued)

*Primary Examiner* — Jay Yang
(74) *Attorney, Agent, or Firm* — Lewis Roca Rothgerber Christie LLP

(57) ABSTRACT

A heterocyclic compound and an organic light-emitting device including the heterocyclic compound, the heterocyclic compound being represented by the following Formula 1:

$$A_1\text{-}(A_2)_{n2},  \quad \text{<Formula 1>}$$

wherein, in Formula 1, $A_1$ is a group represented by one of Formulae 2A and 2B, and $A_2$ is a group represented by Formula 3, Formula 2A (Continued)

-continued

Formula 2B

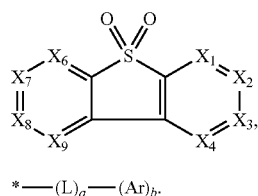

Formula 3

*—(L)$_a$—(Ar)$_b$.

20 Claims, 4 Drawing Sheets

(51) Int. Cl.
    *C07D 401/12* (2006.01)
    *C07D 401/14* (2006.01)
    *H01L 51/52* (2006.01)
    *C07D 401/04* (2006.01)
    *H01L 51/50* (2006.01)

(52) U.S. Cl.
    CPC ......... *C07D 401/12* (2013.01); *C07D 401/14* (2013.01); *H01L 51/005* (2013.01); *H01L 51/006* (2013.01); *H01L 51/0061* (2013.01); *H01L 51/0067* (2013.01); *H01L 51/0094* (2013.01); *H01L 51/5218* (2013.01); *H01L 51/0052* (2013.01); *H01L 51/0085* (2013.01); *H01L 51/5016* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | |
|---|---|---|---|
| 2003/0176416 A1* | 9/2003 | Peters | C07D 487/08 |
| | | | 514/214.03 |
| 2014/0061545 A1 | 3/2014 | Leroy et al. | |
| 2015/0141642 A1 | 5/2015 | Adachi et al. | |
| 2016/0079546 A1* | 3/2016 | Park | H01L 51/0073 |
| | | | 257/40 |
| 2016/0285011 A1 | 9/2016 | Park et al. | |

FOREIGN PATENT DOCUMENTS

| | | |
|---|---|---|
| JP | 2004-220931 A | 8/2004 |
| KR | 10-2011-0129421 A | 12/2011 |
| KR | 10-2014-0031171 A | 3/2014 |
| KR | 10-2014-0127702 * | 11/2014 |
| KR | 10-2015-0016242 A | 2/2015 |
| KR | 10-2016-0114238 A | 10/2016 |
| WO | WO 2014/017045 A1 | 1/2014 |

OTHER PUBLICATIONS

Machine English translation of Zhou et al. (CN 104449665 A). Mar. 7, 2019.*
Cook et al. (J. Chem. Soc., Perkin Trans. 2 1978, 12, p. 1215).*
Armstrong et al. (Angew. Chem. Int. Ed. 2014, 53, p. 12822).*
Su, et al. "RGB Phosphorescent Organic Light-Emitting Didoes by Using Host Materials with Heterocyclic Cores: Effect of Nitrogen Atom Orientations" Chem. Mater., vol. 23, 274-284 (2011).
Zhang, et al. "Efficient Blue Organic Light-Emitting Diodes Employing Thermally Activated Delayed Fluorescence" Nature Photonics, vol. 8, 326-332 (2014).

* cited by examiner

| 190 |
|-----|
| 150 |
| 110 |

| 190 |
|---|
| 150 |
| 110 |
| 210 |

| 220 |
|---|
| 190 |
| 150 |
| 110 |

| 220 |
|---|
| 190 |
| 150 |
| 110 |
| 210 |

HETEROCYCLIC COMPOUND AND ORGANIC LIGHT-EMITTING DEVICE INCLUDING THE SAME

CROSS-REFERENCE TO RELATED APPLICATION

Korean Patent Application No. 10-2016-0098448, filed on Aug. 2, 2016, in the Korean Intellectual Property Office, and entitled: "Heterocyclic Compound and Organic Light-Emitting Device Including the Same," is incorporated by reference herein in its entirety.

BACKGROUND

1. Field

Embodiments relate to a heterocyclic compound and an organic light-emitting device including the same.

2. Description of the Related Art

Organic light-emitting devices are self-emission devices; have wide viewing angles, high contrast ratios, short response times, and excellent luminance, driving voltage, and response speed characteristics; and produce full-color images.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state, thereby generating light.

SUMMARY

Embodiments are directed to a heterocyclic compound and an organic light-emitting device including the same.

The embodiments may be realized by providing a heterocyclic compound represented by Formula 1:

$$A_1\text{-}(A_2)_{n2}.$$ <Formula 1> wherein, in Formula 1, $A_1$ may be a group represented by one of Formulae 2A and 2B:

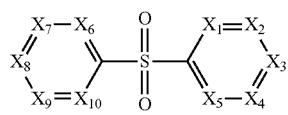

Formula 2A

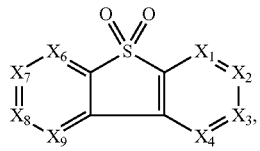

Formula 2B $A_2$ is a group represented by Formula 3:

$$\text{*-}(L)_a\text{-}(Ar)_b$$ Formula 3

The embodiments may be realized by providing an organic light-emitting device, the device including a first electrode; a second electrode facing the first electrode; and an organic layer between the first electrode and the second electrode, the organic layer including an emission layer, wherein the organic layer includes the heterocyclic compound according to an embodiment.

BRIEF DESCRIPTION OF THE DRAWINGS

Features will be apparent to those of skill in the art by describing in detail exemplary embodiments with reference to the attached drawings in which:

FIG. 1 illustrates a schematic sectional view of an organic light-emitting device according to an embodiment;

FIG. 2 illustrates a schematic sectional view of an organic light-emitting device according to an embodiment;

FIG. 3 illustrates a schematic sectional view of an organic light-emitting device according to an embodiment; and FIG. 4 illustrates a schematic sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments of the present disclosure are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list. The term "or" is not an exclusive term, e.g., A or B means: A, B, or A and B.

A heterocyclic compound according to an embodiment may be represented by Formula 1 below.

$$A_1\text{-}(A_2)_{n2}.$$ <Formula 1>

In Formula 1, $A_1$ may be a group represented by one of Formulae 2A and 2B, and $A_2$ may be a group represented by Formula 3.

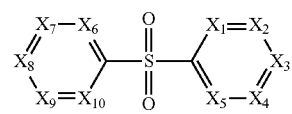

Formula 2A

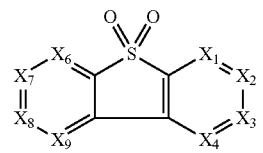

Formula 2B $$\text{*}\text{---}(L)_a\text{---}(Ar)_b.$$ Formula 3 n2, $X_1$ to $X_{10}$, L, a, Ar, and b in Formulae 1 to 3 are described below.

n2 Formula 1 may be an integer from 1 to 7. In one embodiment, n2 may be an integer from 1 to 3. For example, n2 may be 1 or 2. When n2 is two or more, groups represented by Formula 3 may be identical to or different from each other.

In Formulae 2A and 2B, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_9$ may be N or $C(R_9)$, and $X_{10}$ may be N or $C(R_{10})$.

In one embodiment, $A_1$ may be a group represented by one of Formulae 2A and 2B, wherein, in Formula 2A, $X_1$ may be N, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_9$ may be $C(R_9)$, and $X_{10}$ may be $C(R_{10})$, and at least one from $R_2$ to $R_{10}$ may be a binding site to $A_2$ in Formula 1; and, in Formula 2B, $X_1$ may be N, $X_2$ may be $C(R_2)$, $X_3$ may be $C(R_3)$, $X_4$ may be $C(R_4)$, $X_6$ may be $C(R_6)$, $X_7$ may be $C(R_7)$, $X_8$ may be $C(R_8)$, and $X_9$ may be $C(R_9)$. At least one selected from $R_2$ to $R_4$ and $R_6$ to $R_9$ may be a binding site to $A_2$ in Formula 1.

In one embodiment, $A_1$ may be a group represented by one of Formulae 2A and 2B, wherein, in Formula 2A, $X_2$ may be N, $X_1$ may be $C(R_1)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_9$ may be $C(R_9)$, and $X_{10}$ may be $C(R_{10})$, and at least one selected from $R_1$ and $R_3$ to $R_{10}$ may be a binding site to $A_2$ in Formula 1; and, in Formula 2B, $X_2$ may be N, $X_1$ may be $C(R_1)$, $X_3$ may be $C(R_3)$, $X_4$ may be $C(R_4)$, $X_6$ may be $C(R_6)$, $X_7$ may be $C(R_7)$, $X_8$ may be $C(R_8)$, and $X_9$ may be $C(R_9)$, and at least one selected from $R_1$, $R_3$, $R_4$, and $R_6$ to $R_9$ may be a binding site to $A_2$ in Formula 1.

In one embodiment, $A_1$ may be a group represented by one of Formulae 2A and 2B, wherein, in Formula 2A, $X_3$ may be N, $X_1$ may be $C(R_1)$, $X_2$ may be $C(R_2)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_9$ may be $C(R_9)$, and $X_{10}$ may be $C(R_{10})$, and at least one selected from $R_1$, $R_2$ and $R_4$ to $R_{10}$ may be a binding site to $A_2$ in Formula 1; and, in Formula 2B, $X_3$ may be N, $X_1$ may be $C(R_1)$, $X_2$ may be $C(R_2)$, $X_4$ may be $C(R_4)$, $X_6$ may be $C(R_6)$, $X_7$ may be $C(R_7)$, $X_8$ may be $C(R_8)$, and $X_9$ may be $C(R_9)$, and at least one selected from $R_1$, $R_2$, $R_4$, and $R_6$ to $R_9$ may be a binding site to $A_2$ in Formula 1.

In one embodiment, $A_1$ may be a group represented by one of Formulae 2A and 2B, wherein, in Formula 2A, $X_1$ and $X_3$ may each be N, $X_2$ may be $C(R_2)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_9$ may be $C(R_9)$, and $X_{10}$ may be $C(R_{10})$, and at least one selected from $R_2$, $R_4$ and $R_5$ to $R_{10}$ is may be a binding site to $A_2$ in Formula 1; and, in Formula 2B, $X_1$ and $X_3$ may each be N, $X_2$ may be $C(R_2)$, $X_4$ may be $C(R_4)$, $X_6$ may be $C(R_6)$, $X_7$ may be $C(R_7)$, $X_8$ may be $C(R_8)$, and $X_9$ may be $C(R_9)$, and at least one selected from $R_2$, $R_4$, and $R_6$ to $R_9$ may be a binding site to $A_2$ in Formula 1.

In one embodiment, $A_1$ may be a group represented by one of Formulae 2A and 2B, and, in Formula 2A, $X_1$ and $X_6$ may each be N, $X_2$ may be $C(R_2)$, $X_3$ may be $C(R_3)$, $X_4$ may be $C(R_4)$, $X_5$ may be $C(R_5)$, $X_7$ may be $C(R_7)$, $X_8$ may be $C(R_8)$, $X_9$ may be $C(R_9)$, and $X_{10}$ may be $C(R_{10})$, and at least one selected from $R_2$ to $R_5$ and $R_7$ to $R_{10}$ may be a binding site to $A_2$ in Formula 1; and, in Formula 2B, $X_1$ and $X_6$ may each be N, $X_2$ may be $C(R_2)$, $X_3$ may be $C(R_3)$, $X_4$ may be $C(R_4)$, $X_7$ may be $C(R_7)$, $X_8$ may be $C(R_8)$, and $X_9$ may be $C(R_9)$, and at least one selected from $R_2$ to $R_4$ and $R_7$ to $R_9$ may be a binding site to $A_2$ in Formula 1.

In one embodiment, $A_1$ may be a group represented by Formula 2A, and, in Formula 2A, $X_1$, $X_3$, and $X_5$ may each be N, $X_2$ may be $C(R_2)$, $X_4$ may be $C(R_4)$, $X_6$ may be $C(R_6)$, $X_7$ may be $C(R_7)$, $X_8$ may be $C(R_8)$, $X_9$ may be $C(R_9)$, and $X_{10}$ may be $C(R_{10})$, and at least one selected from $R_2$, $R_4$ and $R_6$ to $R_{10}$ may be a binding site to $A_2$ in Formula 1.

In Formulae 2A and 2B, at least one from $X_1$ to $X_{10}$ may be N. For example, two or more from $X_1$ to $X_{10}$ in Formula 2A may be N, and two or more from $X_1$ to $X_4$ and $X_6$ to $X_9$ in Formula 2B may be N.

$R_1$ to $R_{10}$ may each independently be selected from:
a binding site to $A_2$ in Formula 1, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-N(Q_1)(Q_2)$, $-C(=O)(Q_1)$, and $-P(=O)(Q_1)(Q_2)$.

In one embodiment, $R_1$ to $R_{10}$ may each independently be selected from:
a binding site to $A_2$ in Formula 1;
hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group; and $-Si(Q_1)(Q_2)(Q_3)$, wherein $R_1$ to $R_{10}$ may be separate or may optionally be linked to form a substituted or unsubstituted condensed ring, and
$Q_1$ to $Q_3$ may each independently be selected from a $C_1$-$C_{10}$ alkyl group, a $C_1$-$C_{10}$ alkoxy group, a phenyl group, and a naphthyl group.

$R_1$ to $R_{10}$ may optionally form a substituted or unsubstituted condensed ring together.

In one embodiment, $R_8$ and $R_9$ may form dihydroindole together.

L in Formula 3 may be selected from:
a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In one embodiment, L in Formula 3 may be selected from:
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a dihydroacridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a dihydroacridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

In one embodiment, L may be a group represented by one of Formulae 4-1 to 4-27:

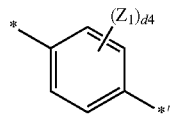

Formula 4-1

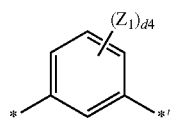

Formula 4-2

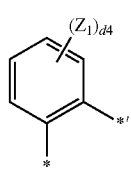

Formula 4-3

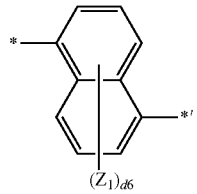

Formula 4-4

-continued
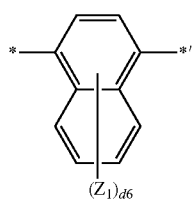
Formula 4-5
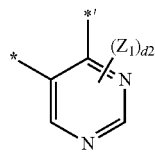
Formula 4-14
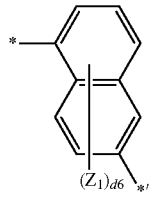
Formula 4-6
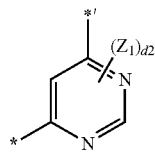
Formula 4-15
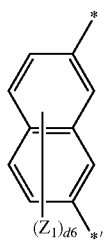
Formula 4-7
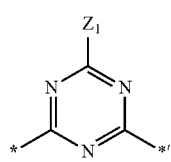
Formula 4-16
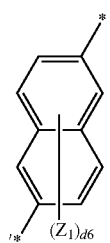
Formula 4-8
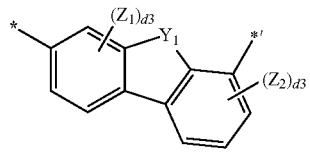
Formula 4-17
Formula 4-9
Formula 4-18
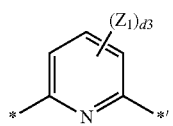
Formula 4-10
Formula 4-19
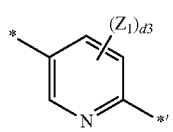
Formula 4-11
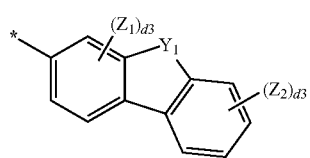
Formula 4-20
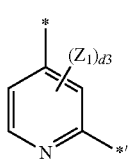
Formula 4-12
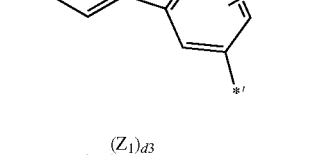
Formula 4-21
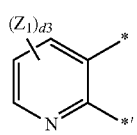
Formula 4-13
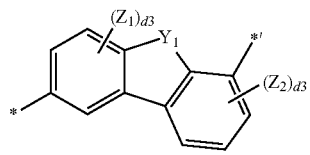
Formula 4-22
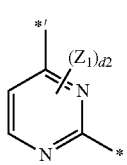
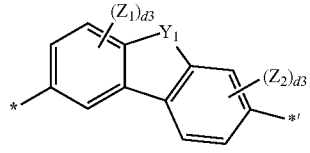
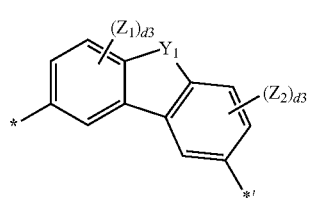

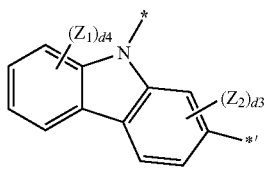

Formula 4-23

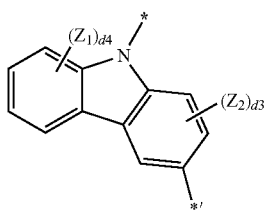

Formula 4-24

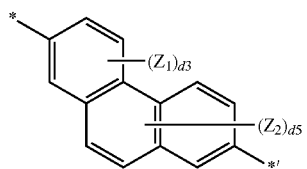

Formula 4-25

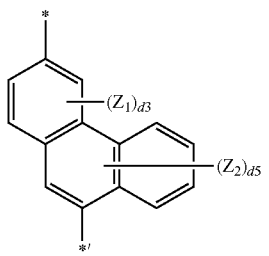

Formula 4-26

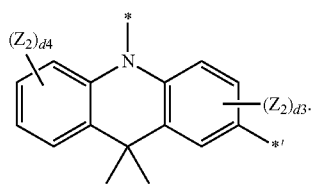

Formula 4-27

In Formulae 4-1 to 4-27, $Y_1$ may be O, S, $C(Z_3)(Z_4)$, $N(Z_5)$, or $Si(Z_6)(Z_7)$, $Z_1$ to $Z_7$ may each independently be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a Spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, and a naphthyl group, d2 may be an integer from 0 to 2,
d3 may be an integer from 0 to 3,
d4 may be an integer from 0 to 4,
d5 may be an integer from 0 to 5,
d6 may be an integer from 0 to 6, and
d8 may be an integer from 0 to 8.

For example, L may be a group represented by one of Formulae 4-1, 4-2, and 4-27.

$Z_1$ and $Z_2$ in Formulae 4-1, 4-2, and 4-27 may each independently be selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, and a naphthyl group.

a may be an integer from 0 to 3. For example, a may be 0 or 1. When a is two or more, L(s) may be identical to or different from each other.

Ar in Formula 3 may be selected from:

a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, Ar may be selected from:

a group represented by one of Formulae 5-1 to 5-8;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group a dibenzosilolyl group, a thiadiazolyl group, an imidazopyridinyl group and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$).

In Formulae 5-1 to 5-8, $Y_{21}$ may be 0 or S, at least one of $Y_{22}$ and $Y_{23}$ may be N, $Z_{21}$ to $Z_{24}$ may each independently be selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, a benzoacridinyl group, a benzophenanthrenyl group, a dibenzophenanthrenyl group, a benzophenanthridinyl group, a dibenzophenanthridinyl group, an indenophenanthrenyl group, an indolophenanthrenyl group, a benzofuranophenanthrenyl group, a benzothiophenanthrenyl group, a benzosilolphenanthrenyl group, an indenophenanthridinyl group, an indolophenanthridinyl group, a benzofuranophenanthridinyl group, a benzothiophenanthridinyl group, a benzosilolphenanthridinyl group, a dinaphthopyrrolyl group, a benzoanthracenyl group, and —Si(Q$_{31}$)(Q$_{32}$)(Q$_{33}$), wherein Q$_{31}$ to Q$_{33}$ may each independently be selected from a C$_1$-C$_{10}$ alkyl group, a C$_1$-C$_{10}$ alkoxy group, a phenyl group, and a naphthyl group, f2 may be an integer from 0 to 2,
f3 may be an integer from 0 to 3,
f4 may be an integer from 0 to 4, and
f5 may be an integer from 0 to 5:

Formula 5-1
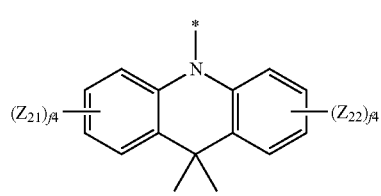

Formula 5-2
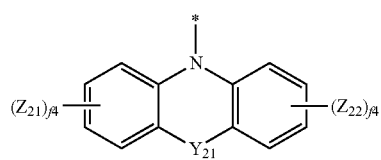

Formula 5-3
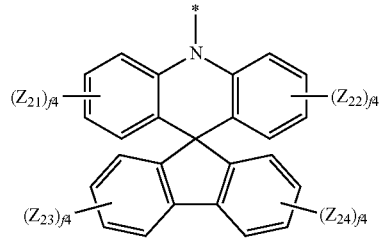

Formula 5-4
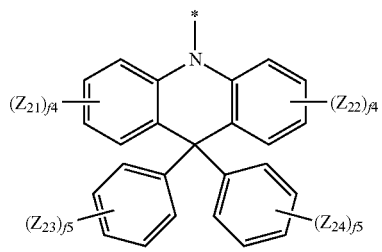

Formula 5-5
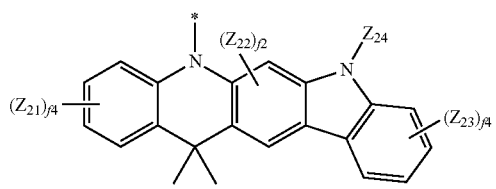

Formula 5-6
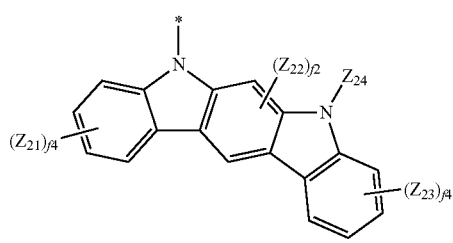

Formula 5-7
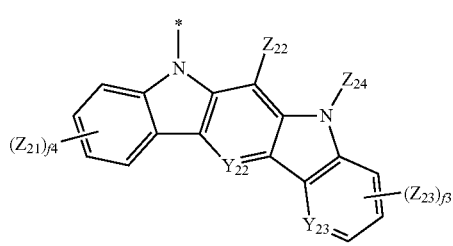

Formula 5-8
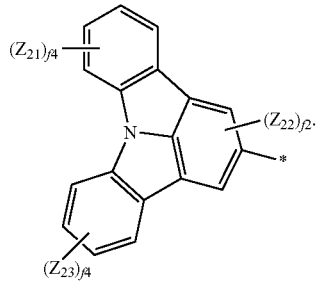

In one embodiment, Ar may be selected from
a group represented by one of Formulae 5-1 to 5-8; and
a group represented by one of Formulae 6-1 to 6-55:

Formula 5-1
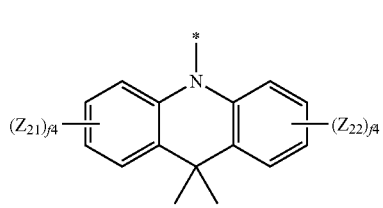

Formula 5-2
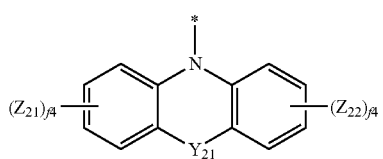
Formula 5-3
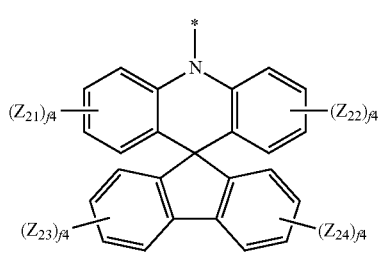
Formula 5-4
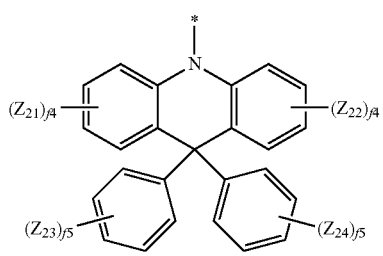
Formula 5-5
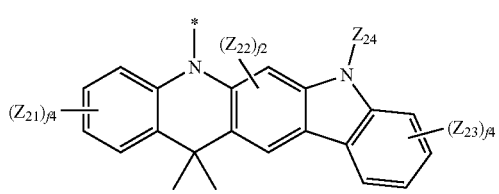
Formula 5-6
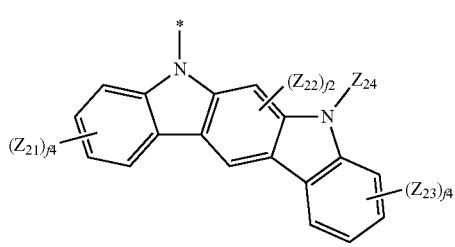
Formula 5-7
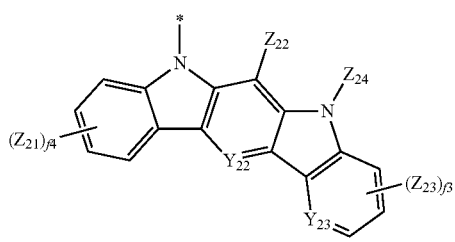
Formula 5-8
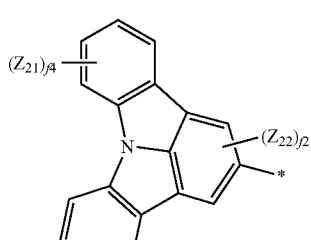
Formula 6-1
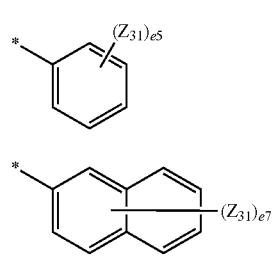
Formula 6-2
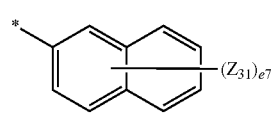
Formula 6-3
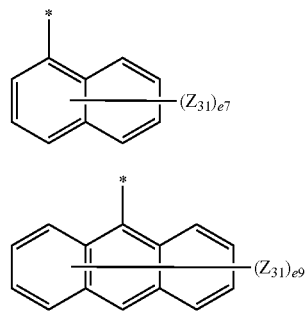
Formula 6-4
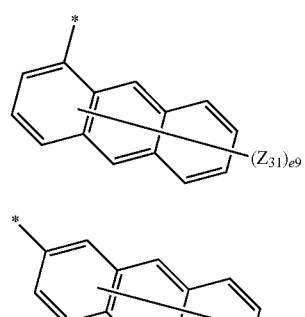
Formula 6-5
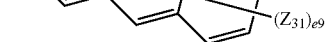
Formula 6-6
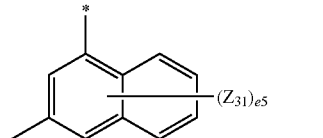
Formula 6-7
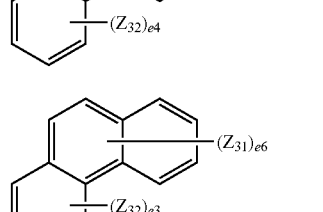
Formula 6-8
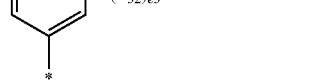

-continued
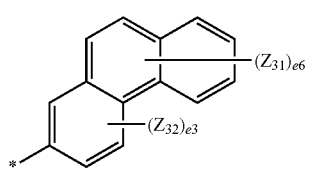
Formula 6-9
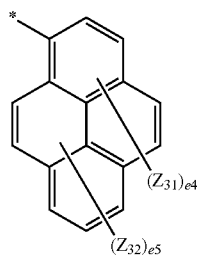
Formula 6-10
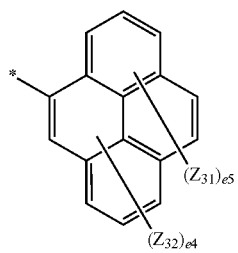
Formula 6-11
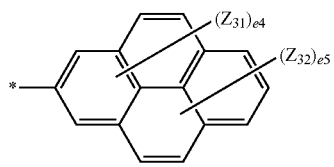
Formula 6-12
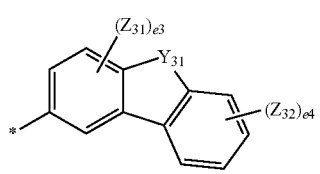
Formula 6-13
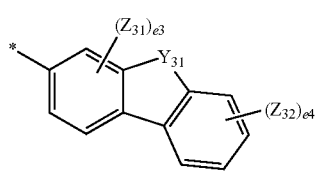
Formula 6-14
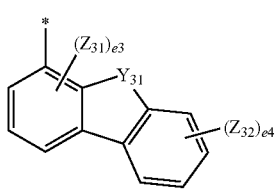
Formula 6-15
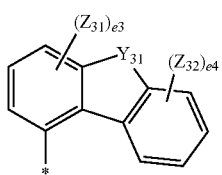
Formula 6-16
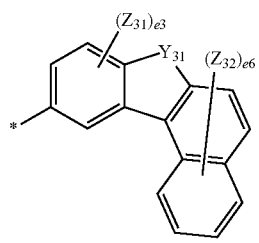
Formula 6-17
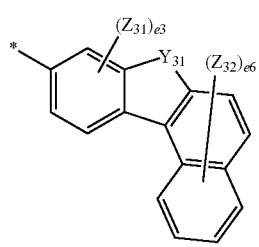
Formula 6-18
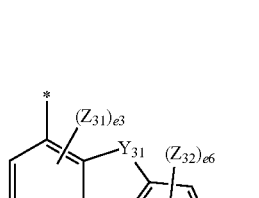
Formula 6-19
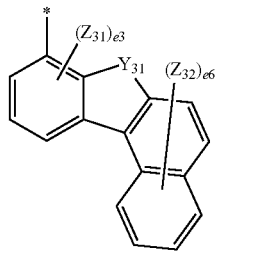
Formula 6-20
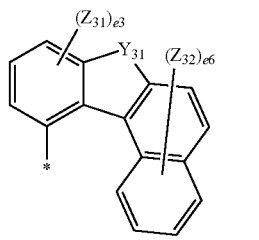
Formula 6-21
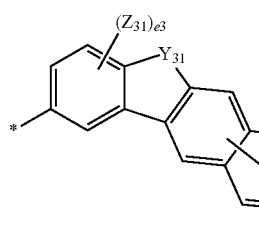
Formula 6-22
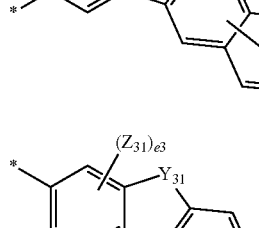
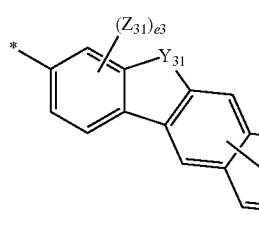

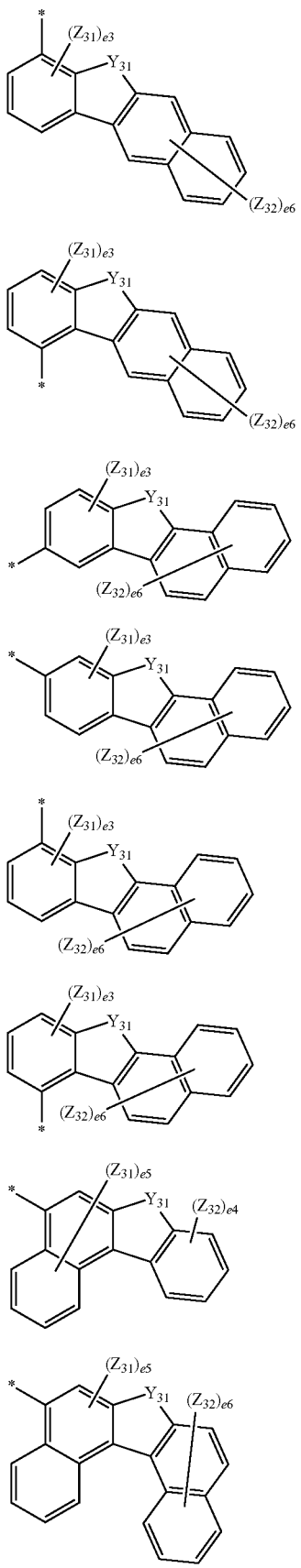
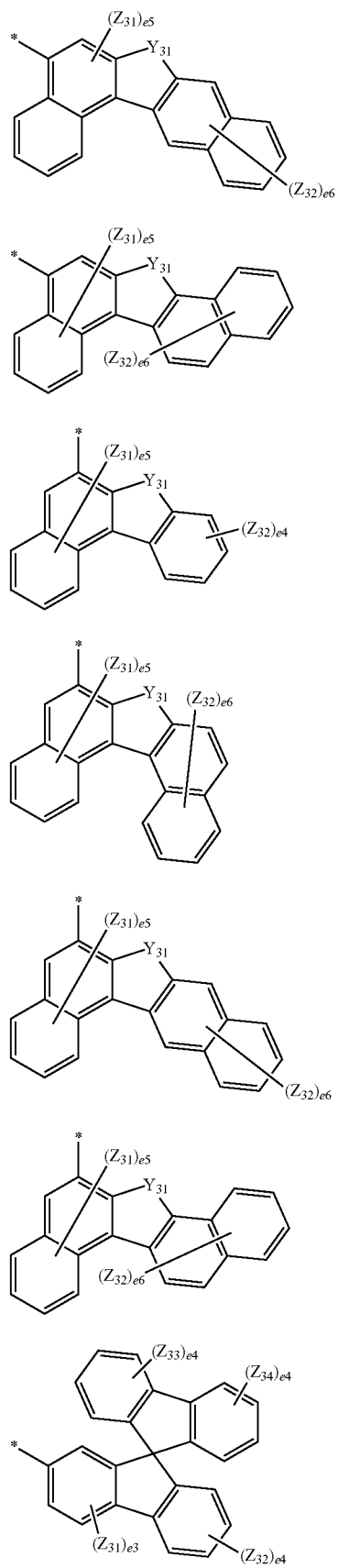

Formula 6-38
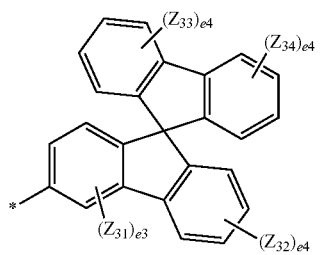
Formula 6-39
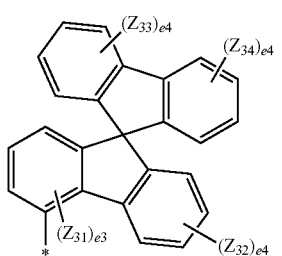
Formula 6-40
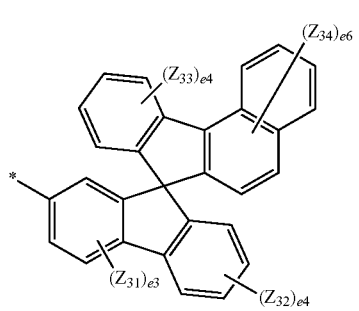
Formula 6-41
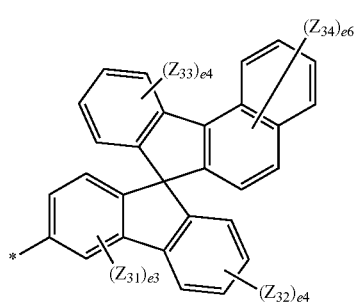
Formula 6-42
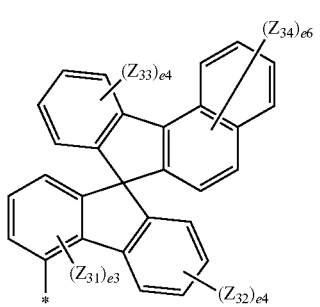
Formula 6-43
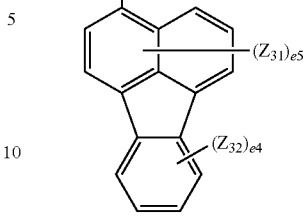
Formula 6-44
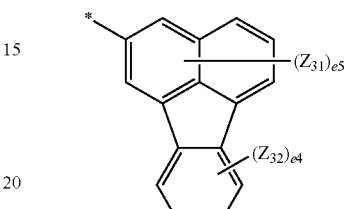
Formula 6-45
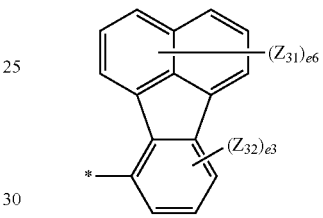
Formula 6-46
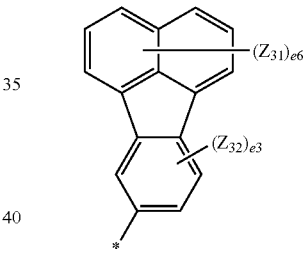
Formula 6-47
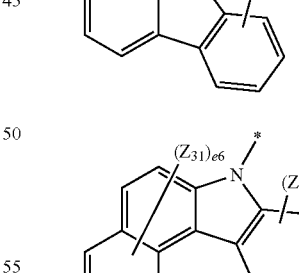
Formula 6-48
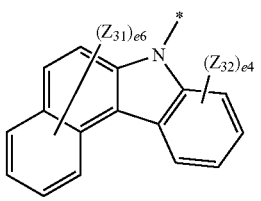
Formula 6-49
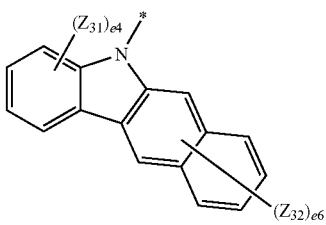

-continued

Formula 6-50
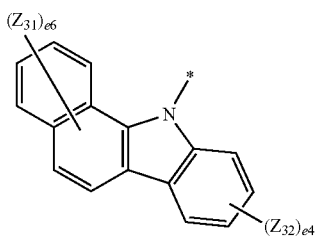

Formula 6-51
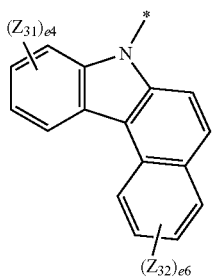

Formula 6-52
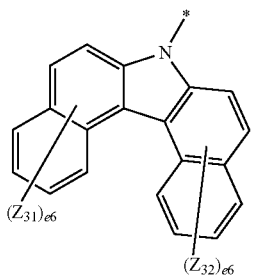

Formula 6-53
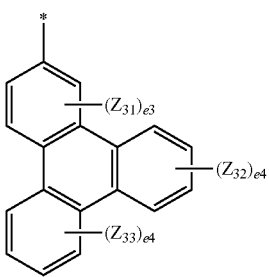

Formula 6-54
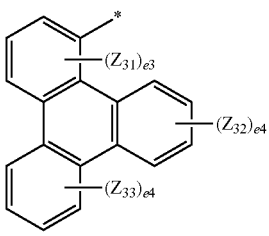

Formula 6-55
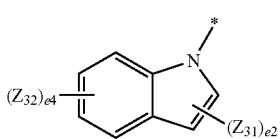

$Y_{21}$, $Y_{22}$, $Y_{23}$, and $Z_{21}$ to $Z_{24}$ in Formulae 5-1 to 5-8 may be the same as described above, and in Formulae 6-1 to 6-55, $Y_{31}$ may be O, S, C($Z_{35}$)($Z_{36}$), N($Z_{37}$), or Si($Z_{38}$)($Z_{39}$), $Z_{31}$ to $Z_{39}$ may each independently be selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, benzoacridinyl group, a benzophenanthrenyl group, a dibenzophenanthrenyl group, a benzophenanthridinyl group, a dibenzophenanthridinyl group, an indenophenanthrenyl group, an indolophenanthrenyl group, a benzofuranophenanthrenyl group, a benzothiophenanthrenyl group, a benzosilolphenanthrenyl group, an indenophenanthridinyl group, an indolophenanthridinyl group, benzofuranophenanthridinyl group, a benzothiophenanthridinyl group, a benzosilolphenanthridinyl group, a dinaphthopyrrolyl group, a benzoanthracenyl group, and —Si($Q_{31}$)($Q_{32}$)($Q_{33}$), wherein $Q_{31}$ to $Q_{33}$ may each independently be selected from a $C_1$-$C_{10}$ alkyl group, a $C_1$-$C_{10}$ alkoxy group, a phenyl group, and a naphthyl group, e2 may be an integer from 0 to 2,
e3 may be an integer from 0 to 3,
e4 may be an integer from 0 to 4,
e5 may be an integer from 0 to 5, and
e6 may be an integer from 0 to 6.

For example, Ar may be a group represented by one of Formulae 5-1 to 5-8, Formulae 6-1 to 6-3, 6-13 to 6-16, 6-37 to 6-39, 6-47, 6-48, and 6-50 to 6-55.

b may be an integer from 1 to 4. In one embodiment, b may be an integer from 1 to 3. For example, b may be an integer of 1 or 2. When b is two or more, Ar(s) may be identical to or different from each other.

In an implementation, the heterocyclic compound represented by Formula 1 may be one of Compounds 1 to 102
1
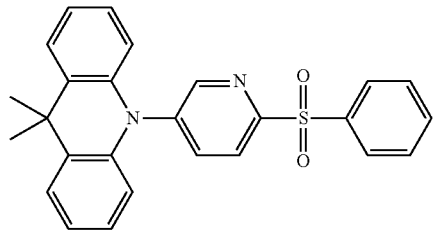
2
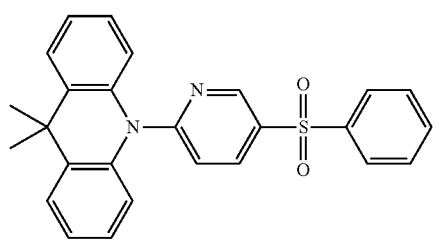
3
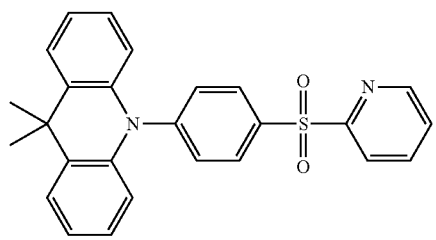
4
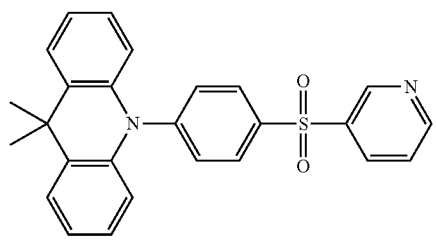
5
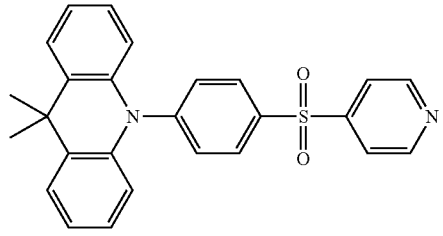
11
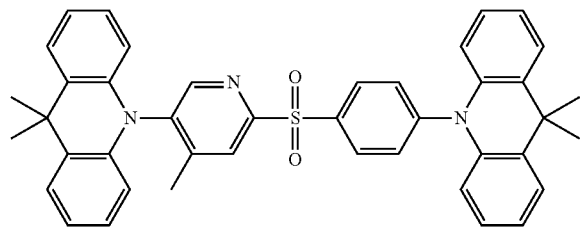
12
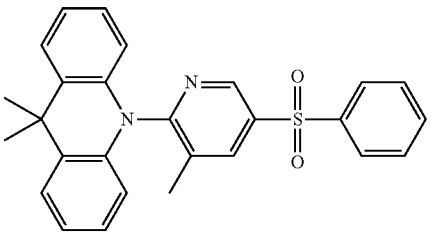
13
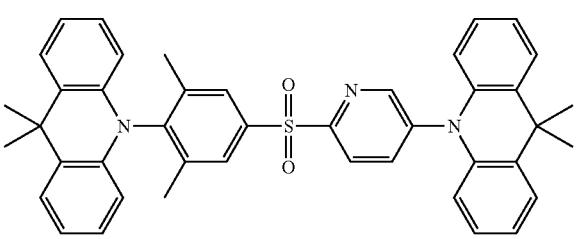
14
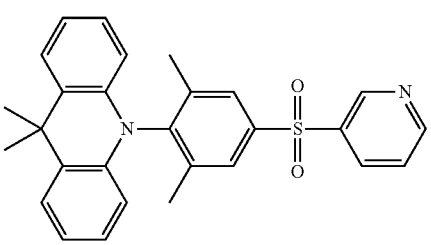
15
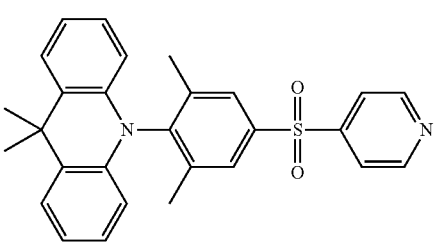
16
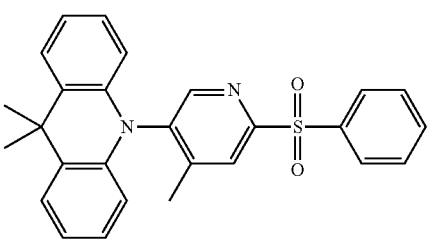
17
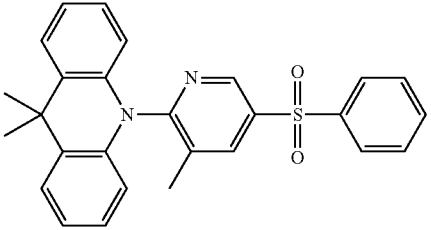

18
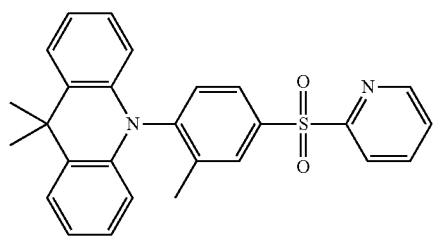
19
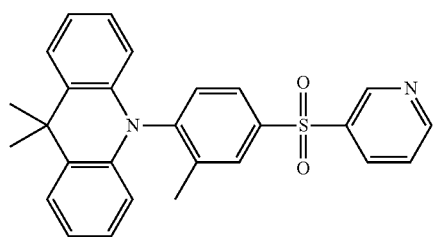
20
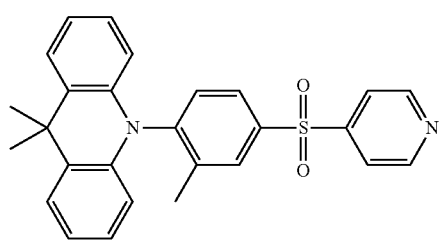
21
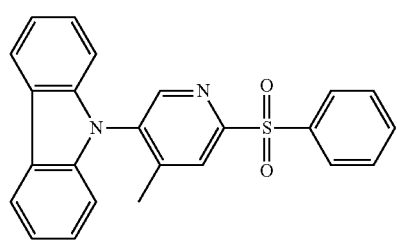
22
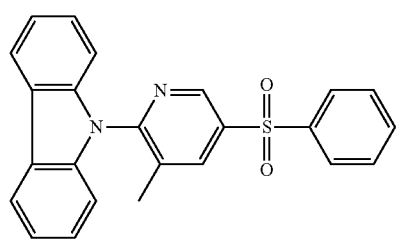
23
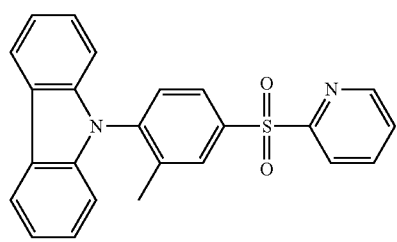
24
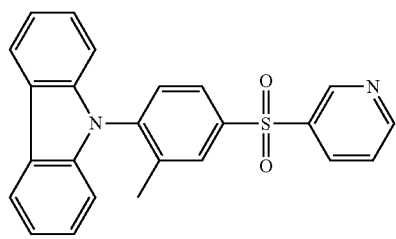
25
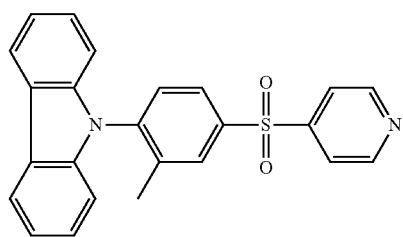
26
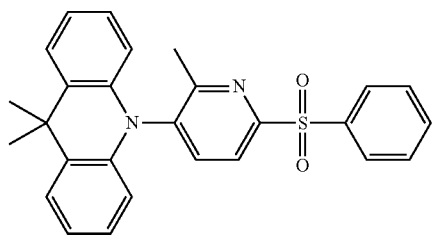
27
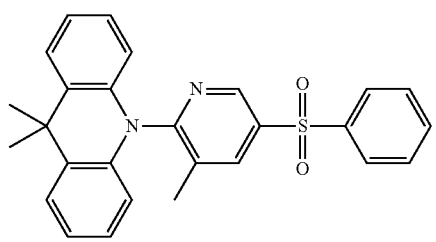
28
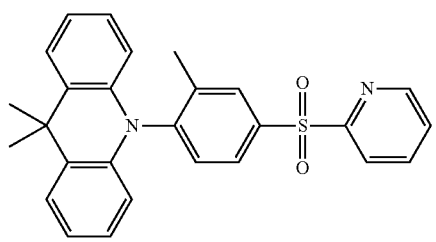
29
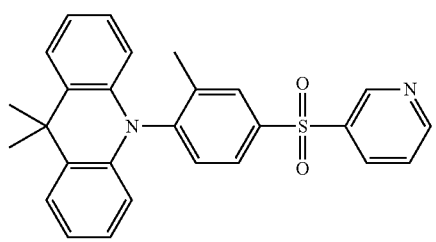

30
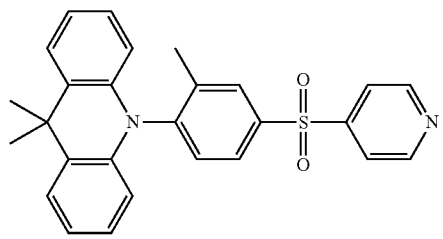
31
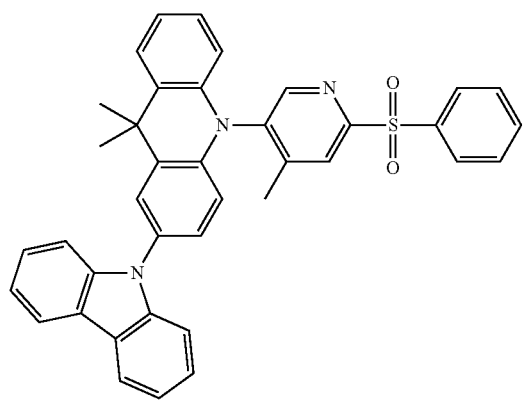
32
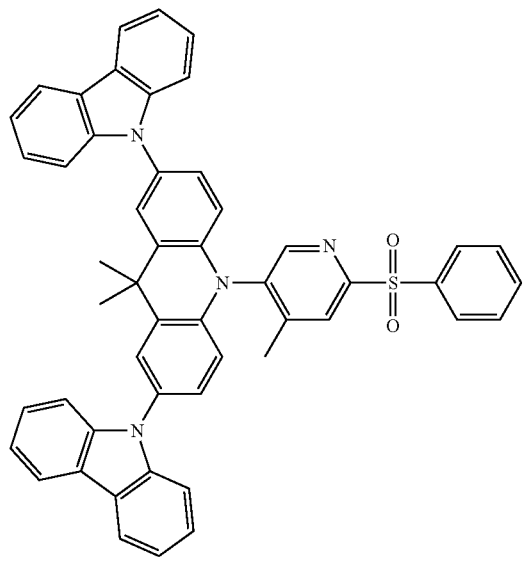
33
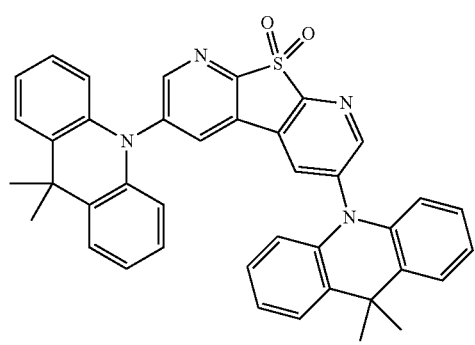
34
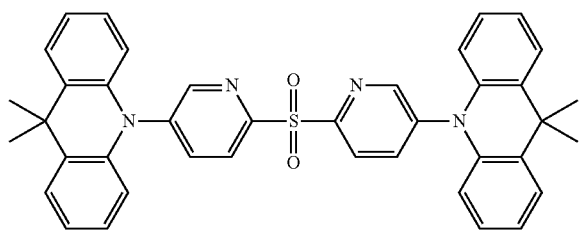
35
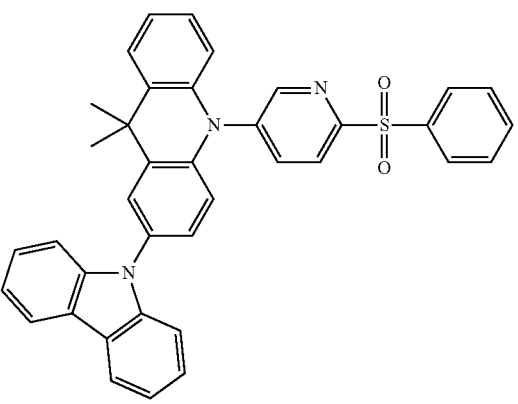
36
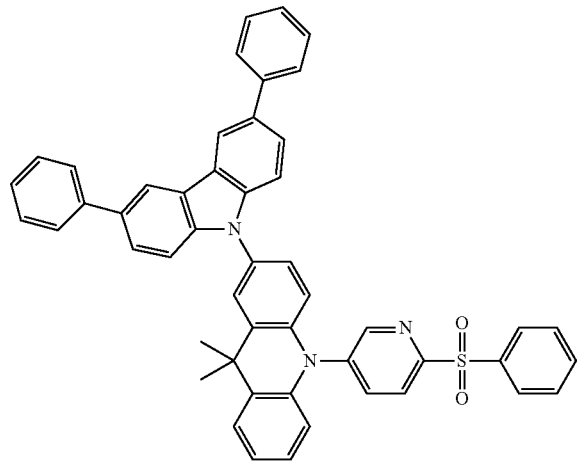
37
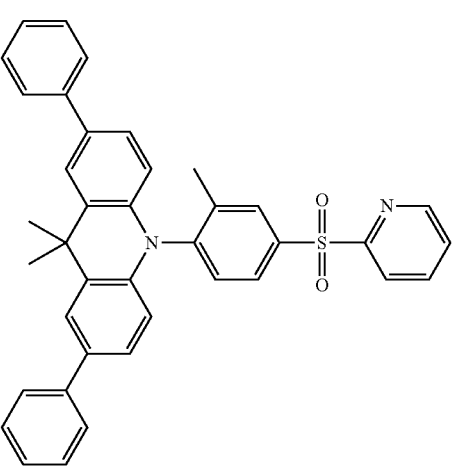

38
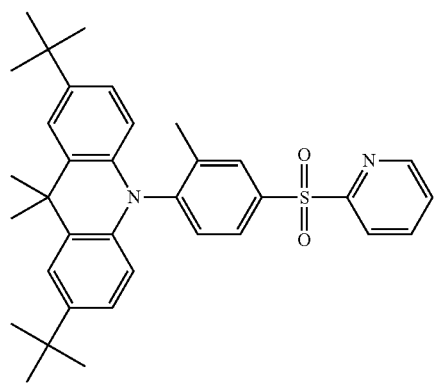
39
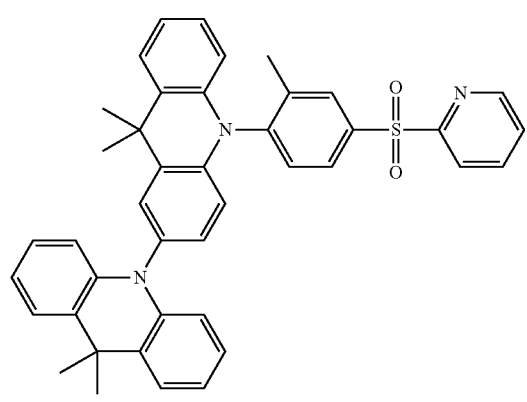
40
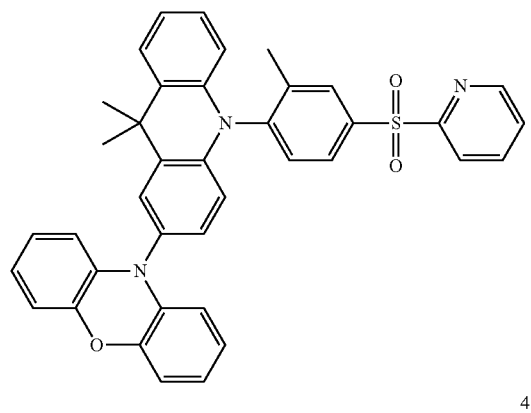
41
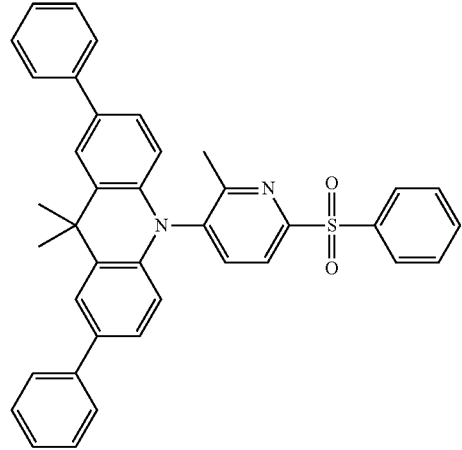
42
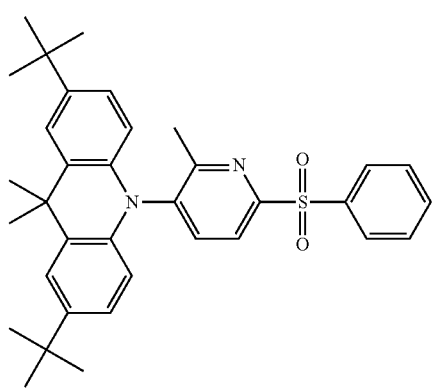
43
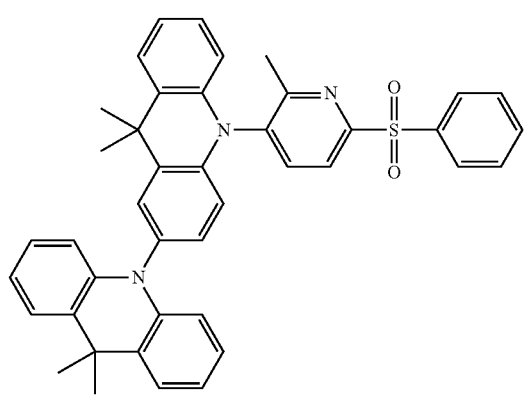
44
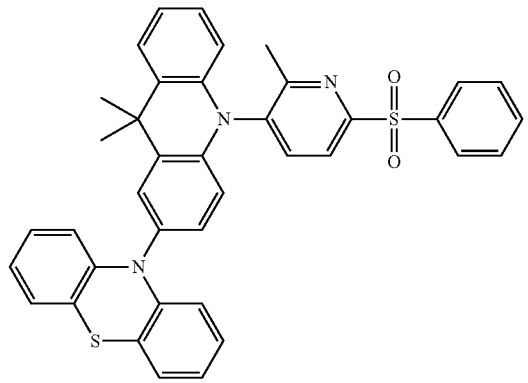
45
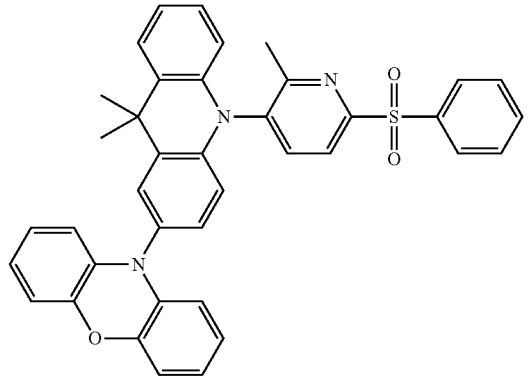

46
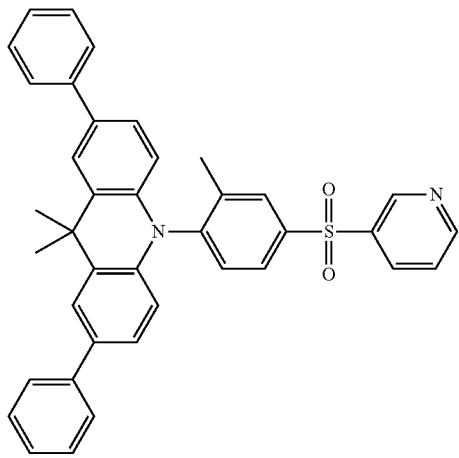
47
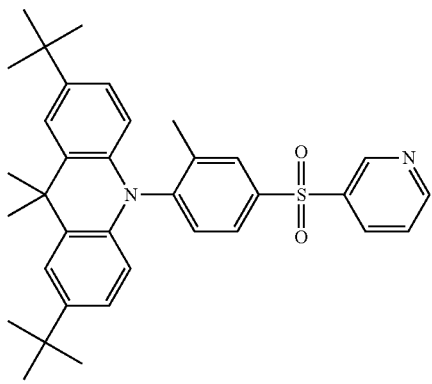
48
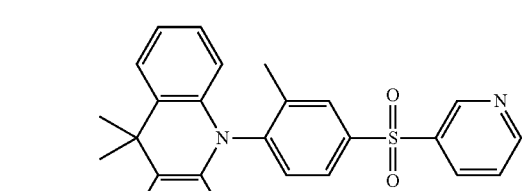
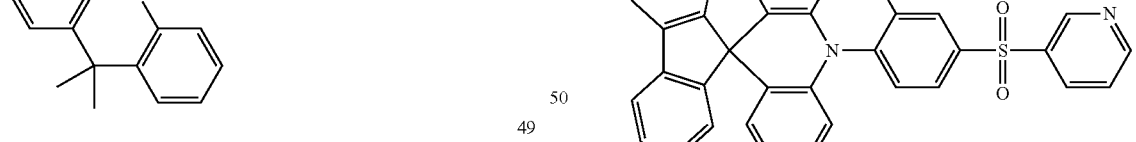
49
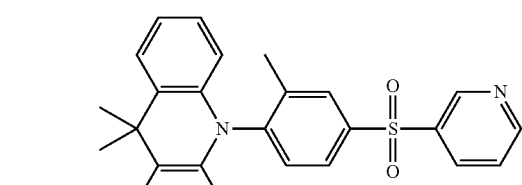
50
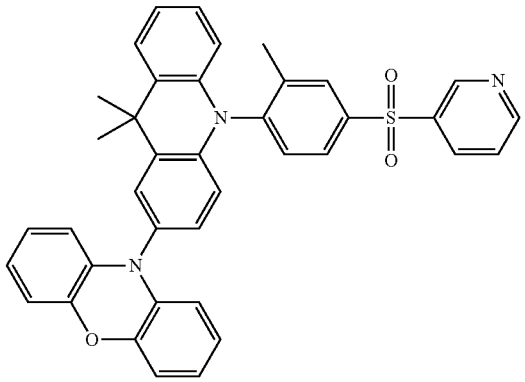
51
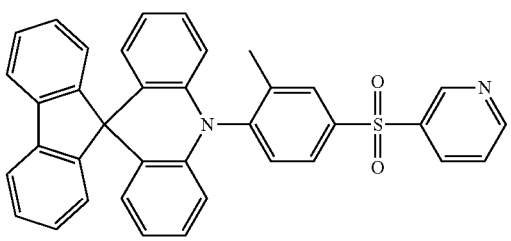
52
53
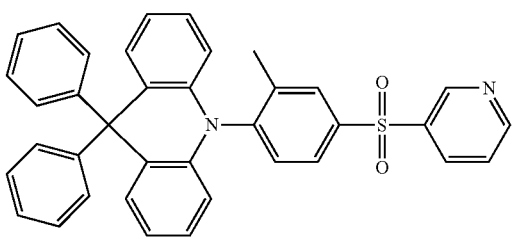

54
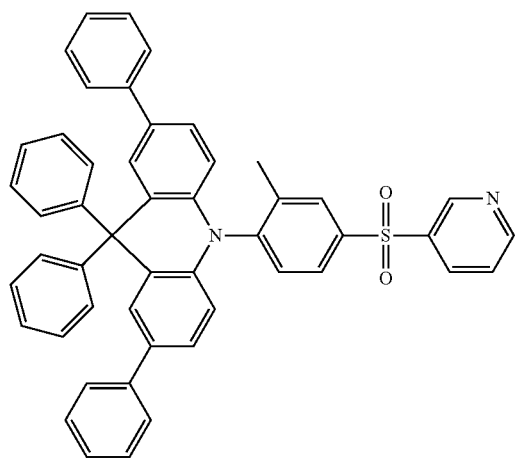
55
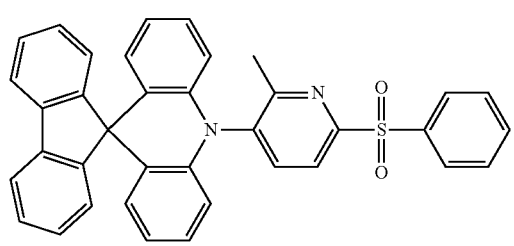
56
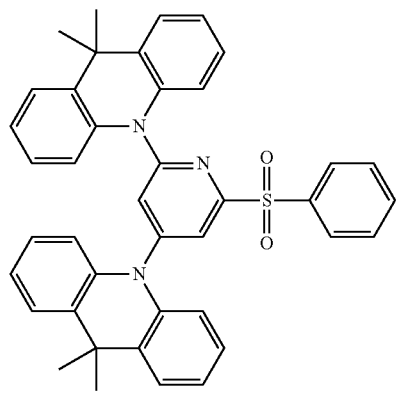
57
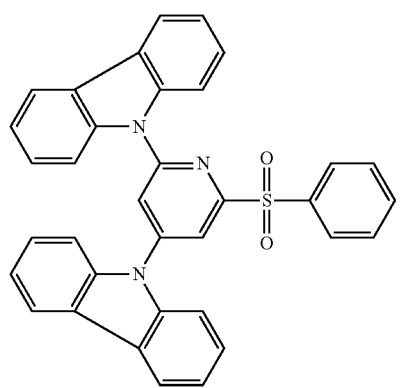
58
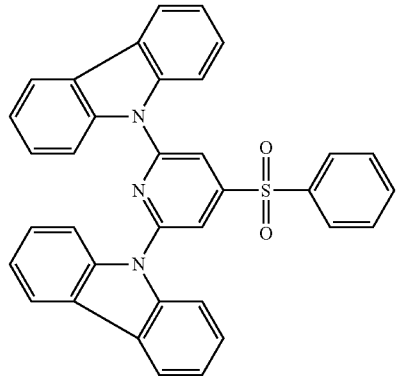
59
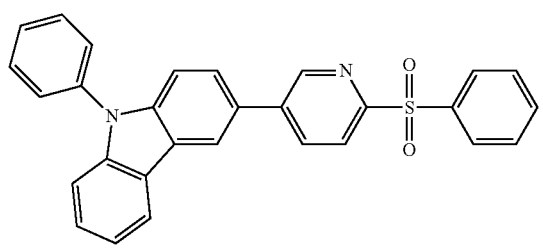
60
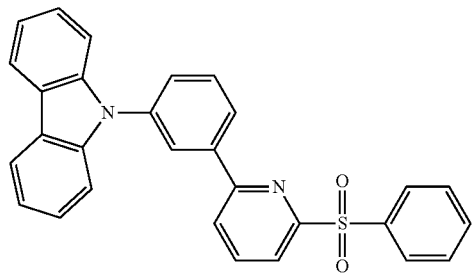
61
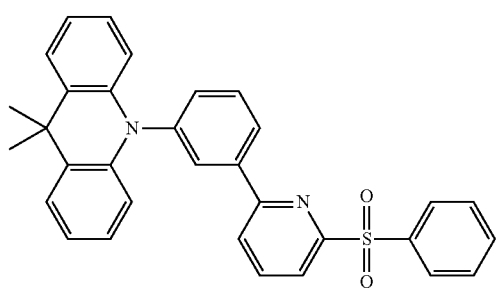
62
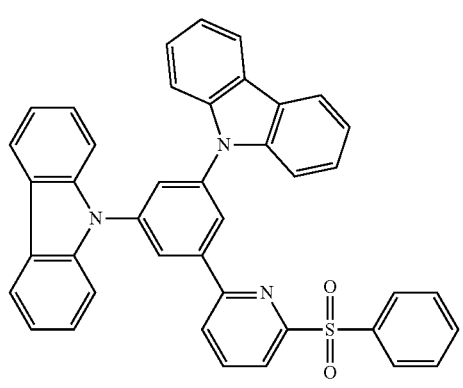

63
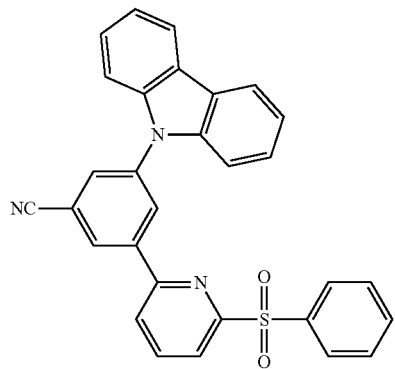
64
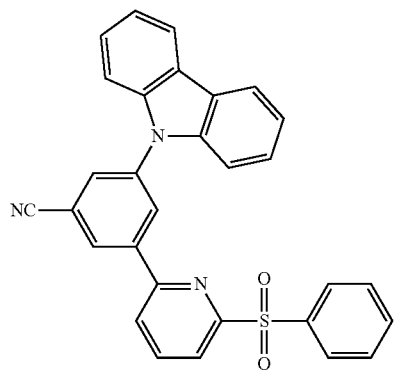
65
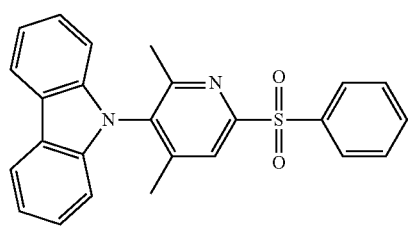
66
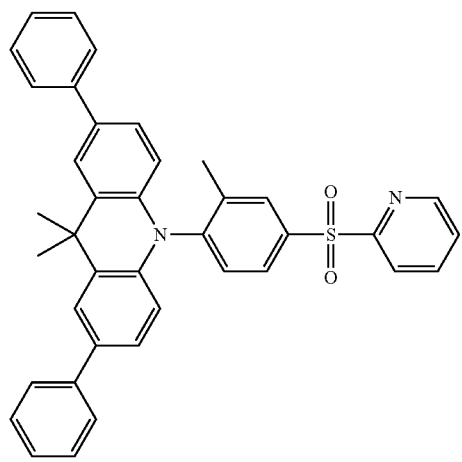
67
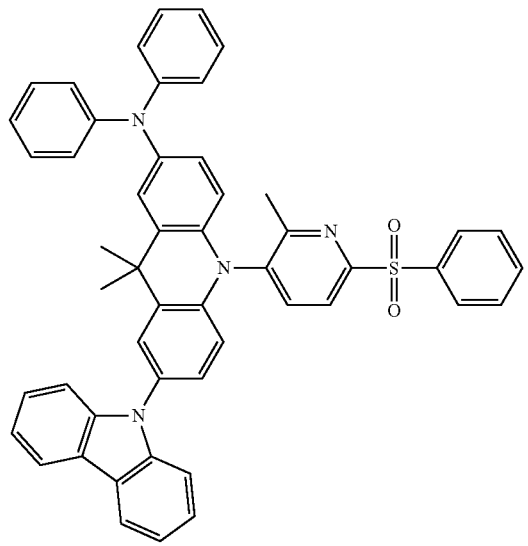
68
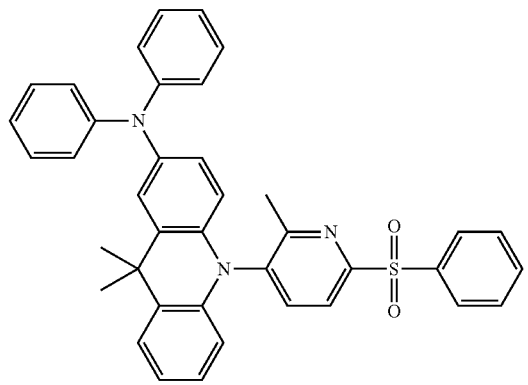
69
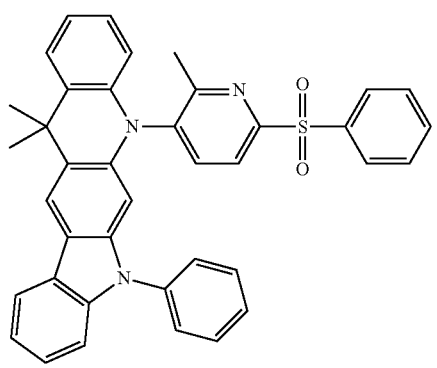

-continued
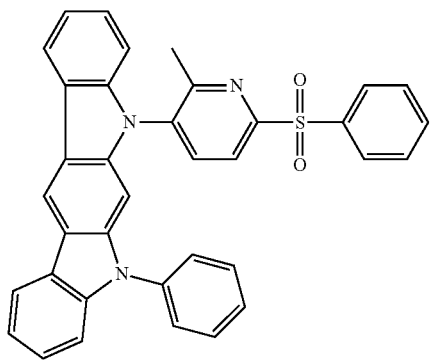
70
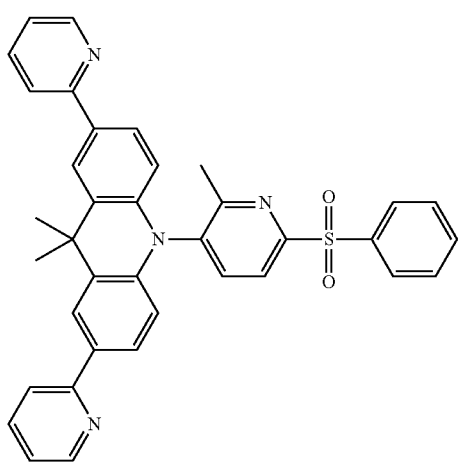
71
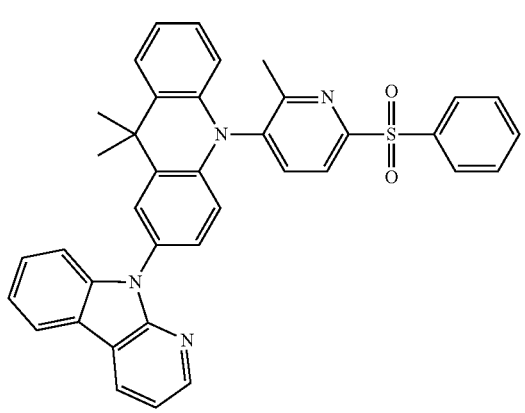
72
-continued
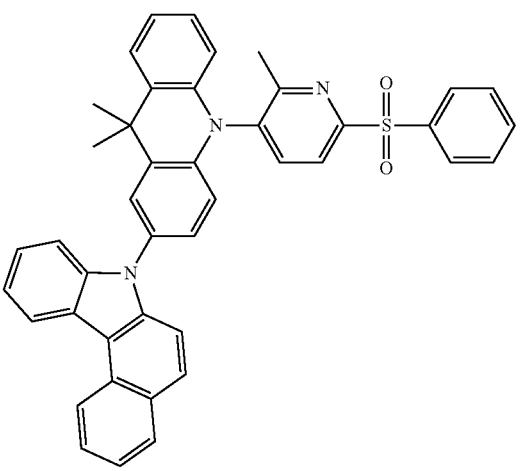
73
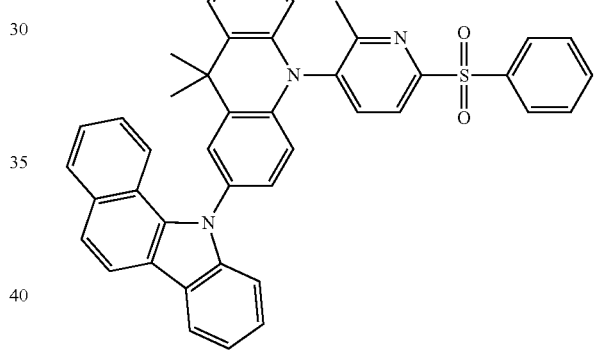
74
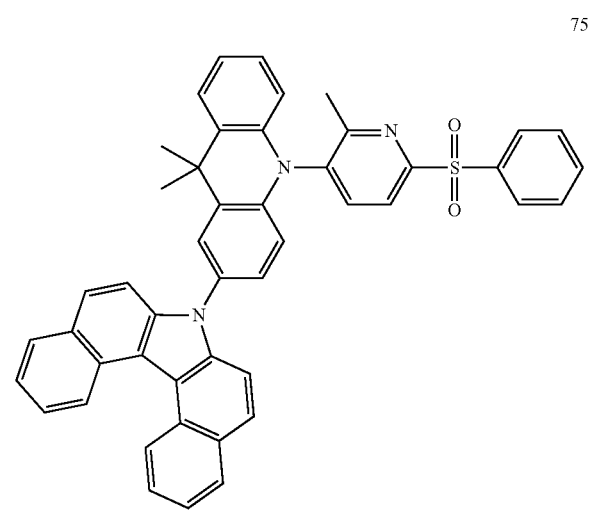
75

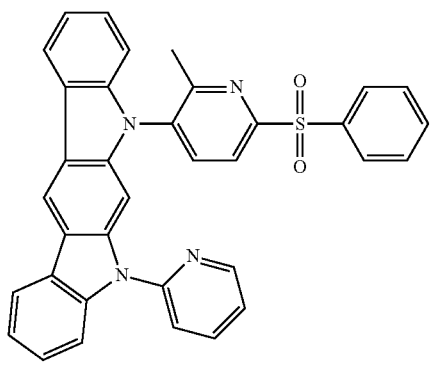
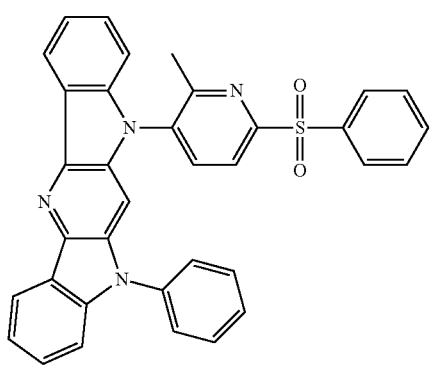
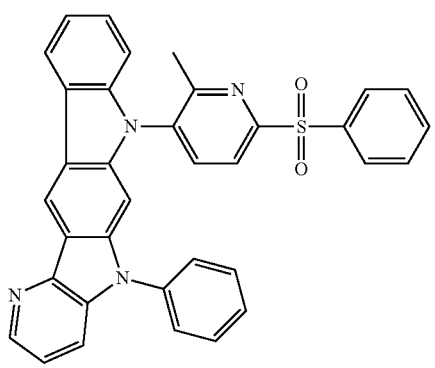
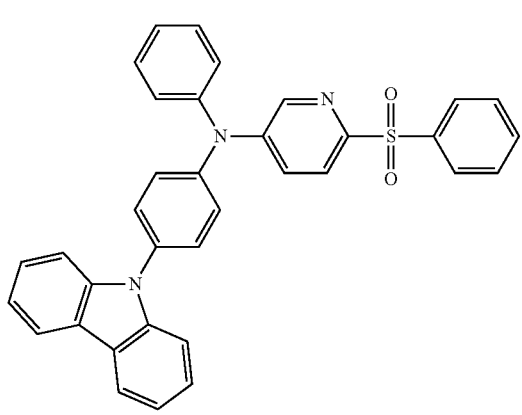
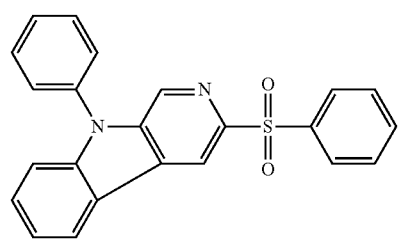
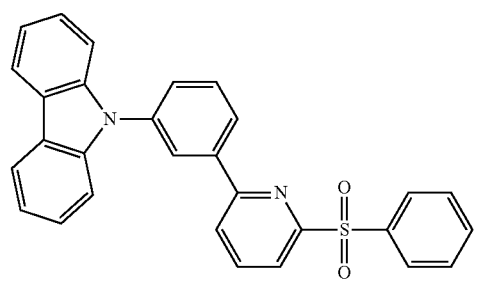
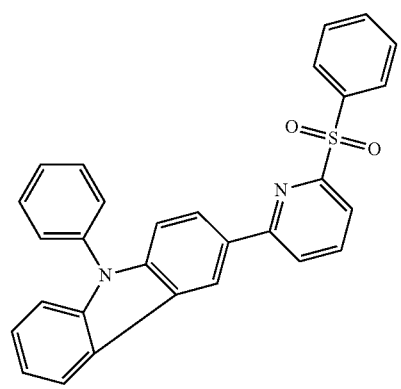
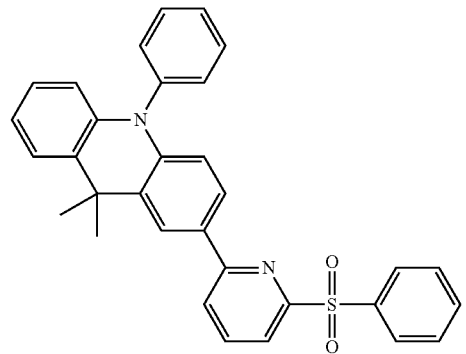
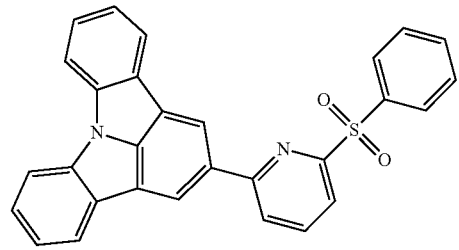

84
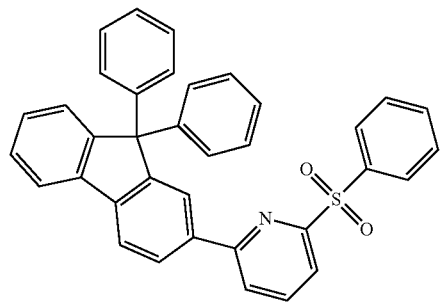
85
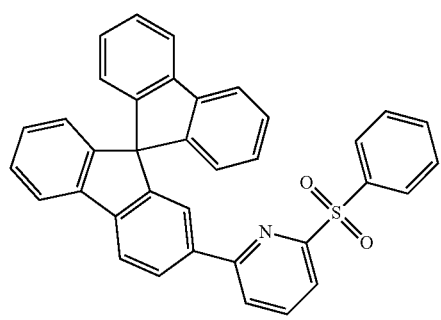
86
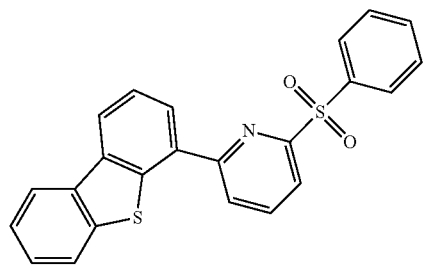
87
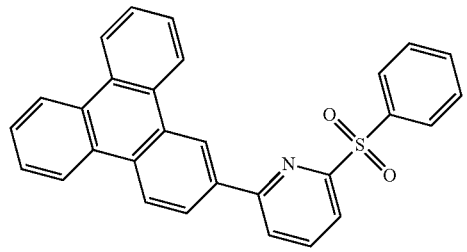
88
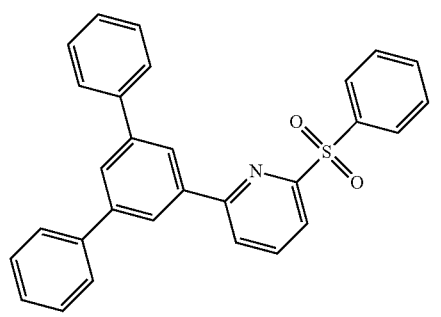
89
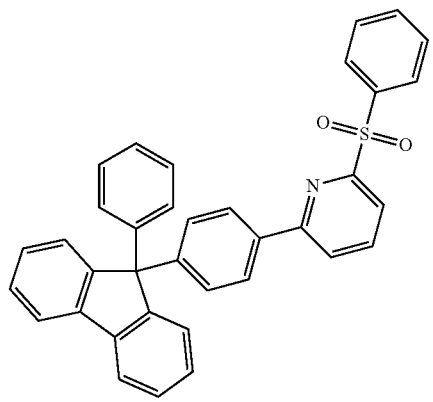
90
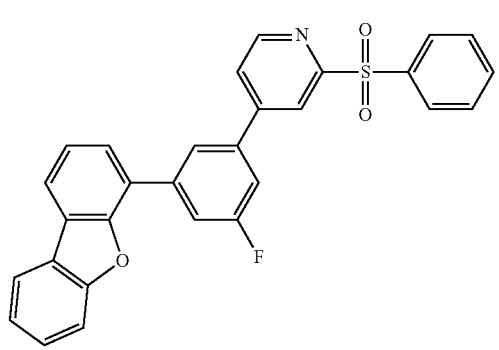
91
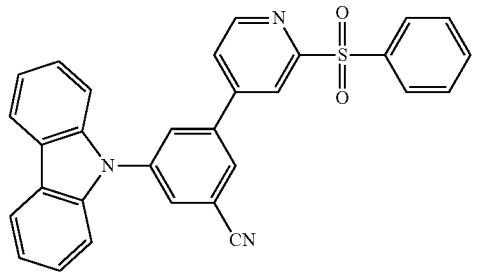
92
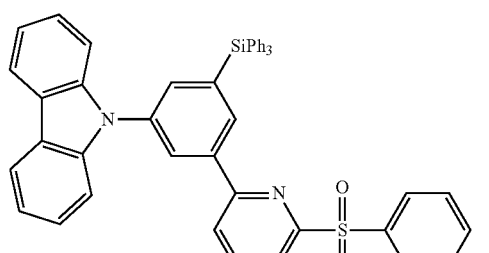
93
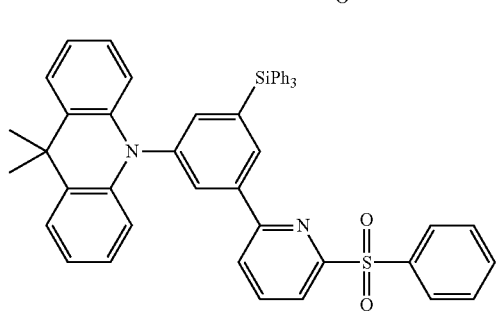

94
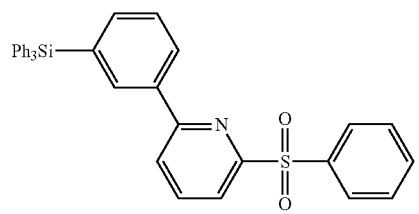
95
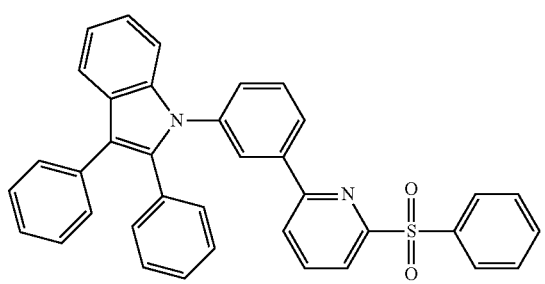
96
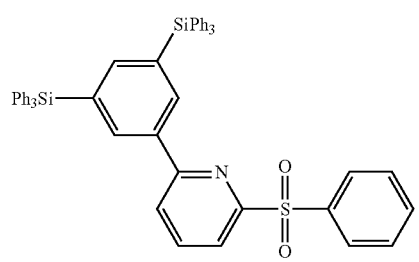
97
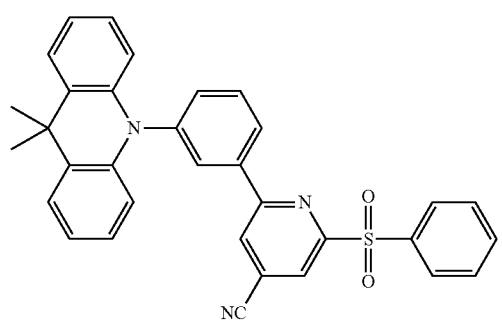
98
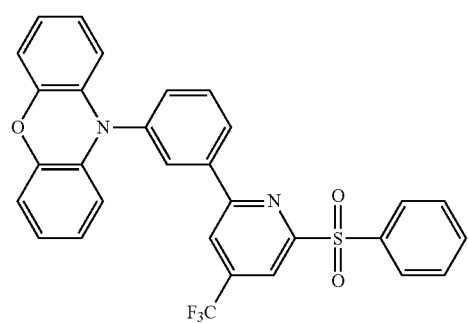
99
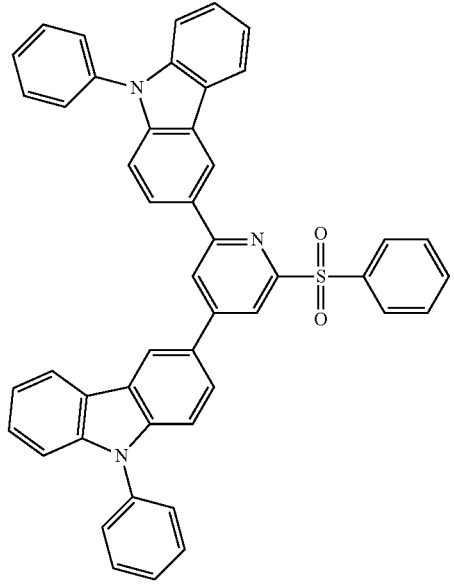
100
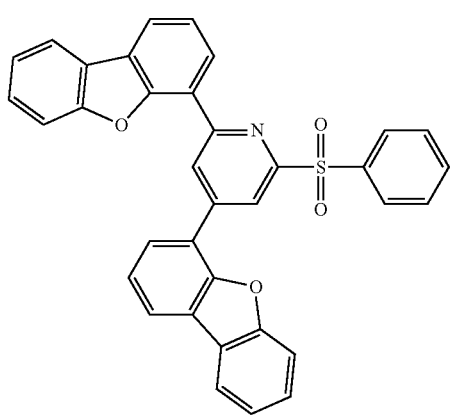
101
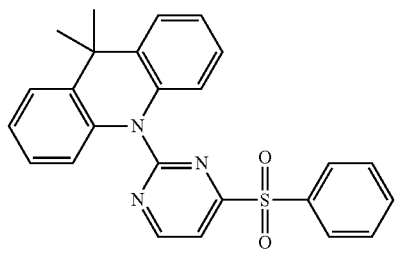
102
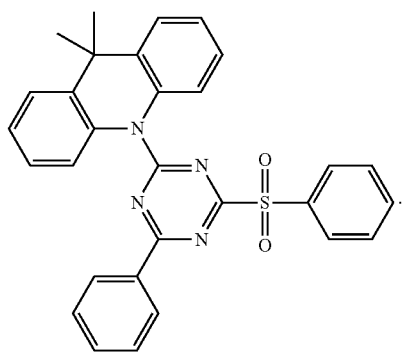

The heterocyclic compound represented by Formula 1 includes a sulfoxide structure having a strong electron-accepting capability. Accordingly, an electron-accepting sulfoxide substituent may function as a strong electron acceptor, and may be paired with an electron donor that is to be combined with sulfoxide to form a donor-acceptor type compound. Accordingly, strong emission characteristics based on intramolecular charge transfer-type transition may be obtained.

Also, at least one N-containing 6-membered aromatic ring may be combined with the sulfoxide structure to easily adjust an energy level and molecular polarity to be appropriate for an organic light-emitting device having a specific structure, leading to an improvement in characteristics of the organic light-emitting device.

A molecular polarity difference may affect an molecular energy level and an intermolecular interaction, resulting in a change in hole mobility and electron mobility of an organic light-emitting device. As a result, the controlling of molecular polarity may be closely related to characteristics of the organic light-emitting device.

A heterocyclic compound having a donor-acceptor structure based on the sulfoxide structure according to the present disclosure may be useful to develop a dopant that is to be optimally combined with a host. Also, according to a substituent or where the substituent is linked, the heterocyclic compound having the sulfoxide substituent may be used as, in addition to the dopant, a host, and a material for forming an electron transport layer.

A synthesis method for the heterocyclic compound represented by Formula 1 would be apparent by referring to the following examples.

At least one heterocyclic compound represented by Formula 1 may be included between a pair of electrodes of an organic light-emitting device. For example, the heterocyclic compound may be included in an electron transport region or an emission layer. In one or more embodiments, the heterocyclic compound of Formula 1 may be used as a material for a capping layer located outside a pair of electrodes of an organic light-emitting device.

According to another aspect of embodiments, an organic light-emitting device may include, e.g., a first electrode, a second electrode, and an organic layer between the first electrode and the second electrode, the organic layer including an emission layer. The organic layer may include at least one heterocyclic compound represented by Formula 1 described above.

The expression "(an organic layer) includes at least one heterocyclic compound" used herein may include a case in which "(an organic layer) includes identical heterocyclic compounds represented by Formula 1" and a case in which "(an organic layer) includes two or more different heterocyclic compounds represented by Formula 1."

For example, the organic layer may include, as the heterocyclic compound, only Compound 1. In this regard, Compound 1 may exist in an emission layer of the organic light-emitting device. In one or more embodiments, the organic layer may include, as the heterocyclic compound, Compound 1 and a Compound 2. In this regard, Compound 1 and a Compound 2 may exist in an identical layer (for example, Compound 1 and a Compound 2 may all exist in an emission layer), or different layers (for example, Compound 1 may exist in an emission layer and a Compound 2 may exist in an electron transport layer).

The organic layer may include i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. The electron transport region or the emission layer may include at least one heterocyclic compound represented by Formula 1. In one embodiment, the organic light-emitting device may include an emission layer, which includes the heterocyclic compound represented by Formula 1. The emission layer may include a host and a dopant, and one of the host or the dopant may include at least one heterocyclic compound represented by Formula 1. The heterocyclic compound represented by Formula 1 included in the emission layer may act as a host, and, in this case, the emission layer may further include a dopant to be described below. In one embodiment, the heterocyclic compound represented by Formula 1 included in the emission layer may act as a dopant, and, in this case, the emission layer may further include a host to be described later.

The organic light-emitting device may further include at least one selected from a first capping layer disposed in a pathway along which light generated in an emission layer proceeds toward outside through the first electrode and a second capping layer disposed in a pathway along which light generated in an emission layer proceeds toward outside through the second electrode, and the at least one selected from the first capping layer and the second capping layer may include at least one of the heterocyclic compounds.

For example, the organic light-emitting device may have i) a stack structure including a first electrode, an organic layer, a second electrode, and a second capping layer which are sequentially stacked in this stated order, ii) a stack structure including a first capping layer, a first electrode, an organic layer, and a second electrode which are sequentially stacked in this stated order, or iii) a stack structure including a first capping layer, a first electrode, an organic layer, a second electrode, and a second capping layer which are sequentially stacked in this stated order, and at least one selected from the first capping layer and the second capping layer may include the heterocyclic compound.

The term "organic layer" used herein refers to a single layer and/or a plurality of layers disposed between the first electrode and the second electrode of the organic light-emitting device. A material included in the "organic layer" is not limited to an organic material.

Figure 1:
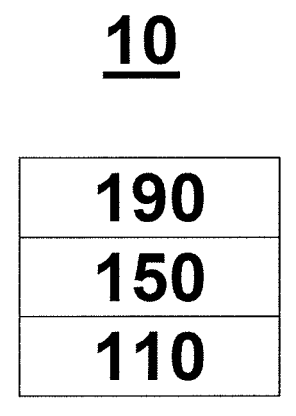

FIG. 1 illustrates a schematic view of an organic light-emitting device 10 according to an embodiment. The organic light-emitting device 10 may include a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

In an implementation, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water-resistance.

The first electrode 110 may be formed by depositing or sputtering a material for forming the first electrode 110 on the substrate. When the first electrode 110 is an anode, the material for a first electrode may be selected from materials with a high work function to facilitate hole injection.

The first electrode 110 may be a reflective electrode, a semi-transmissive electrode, or a transmissive electrode. When the first electrode 110 is a transmissible electrode, a material for forming a first electrode may be selected from indium tin oxide (ITO), indium zinc oxide (IZO), tin oxide (SnO$_2$), zinc oxide (ZnO), and any combinations thereof. In one or more embodiments, when the first electrode 110 is a semi-transmissible electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof.

The first electrode 110 may have a single-layered structure, or a multi-layered structure including two or more layers. For example, the first electrode 110 may have a three-layered structure of ITO/Ag/ITO.

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzenesulfonic acid (PANI/DBSA), poly(3,4-ethylenedi oxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

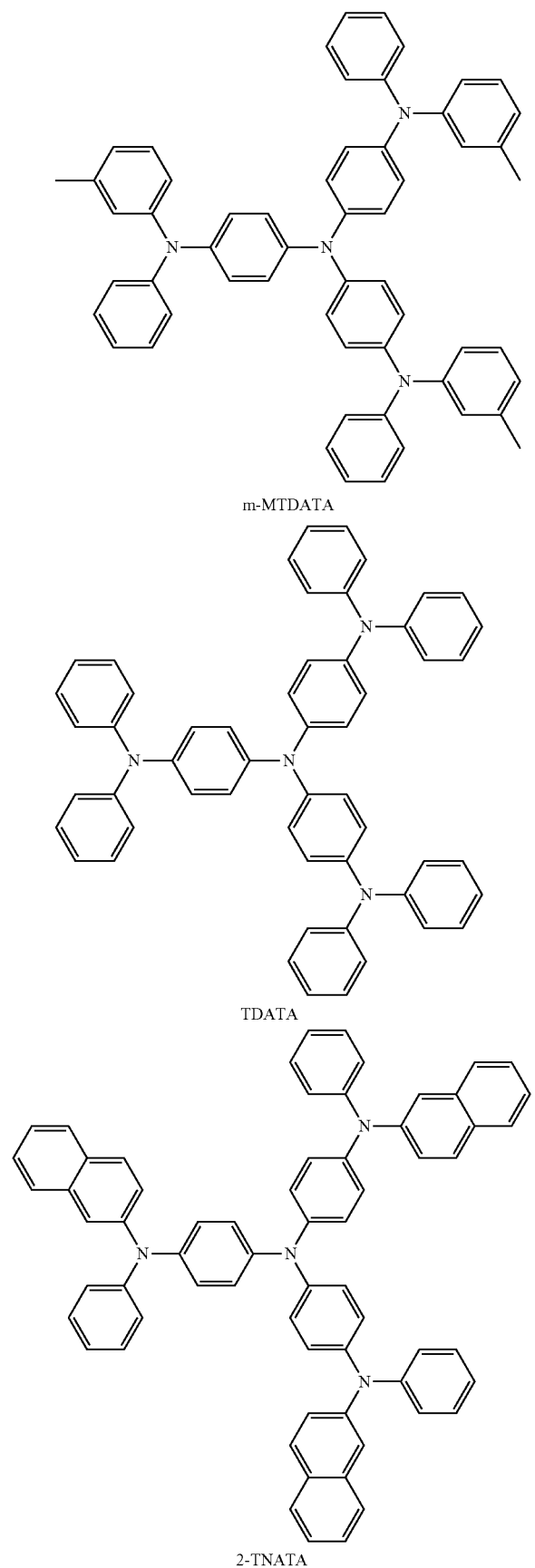

m-MTDATA

TDATA

2-TNATA

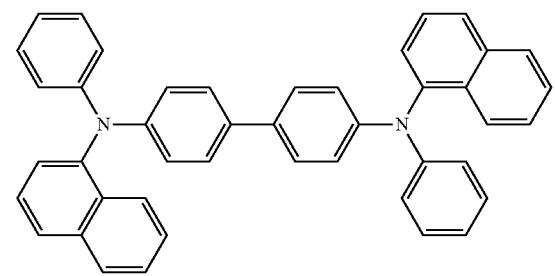

NPB

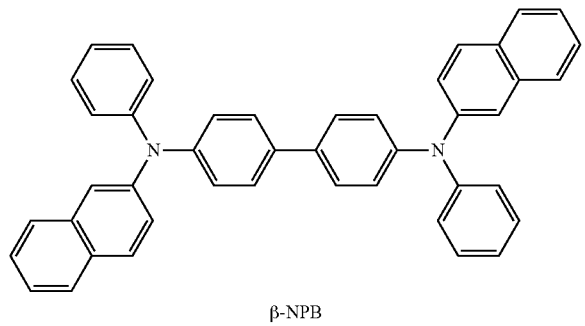

β-NPB

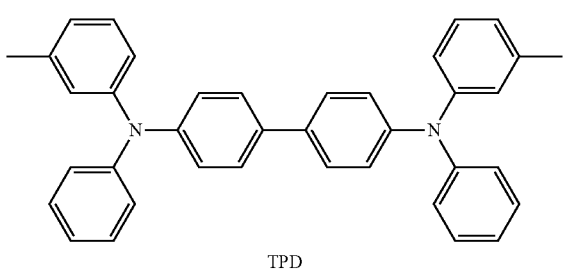

TPD

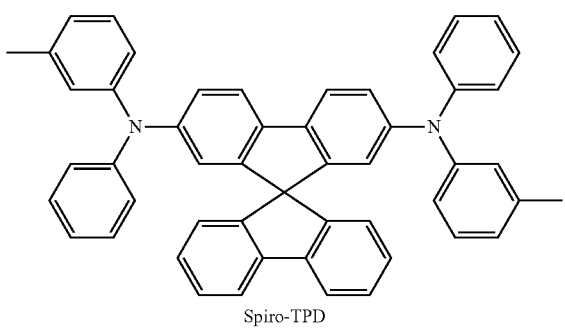

Spiro-TPD

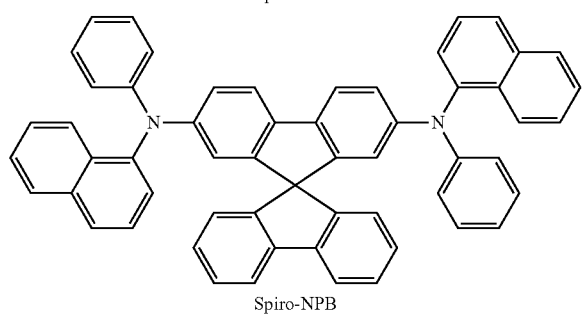

Spiro-NPB

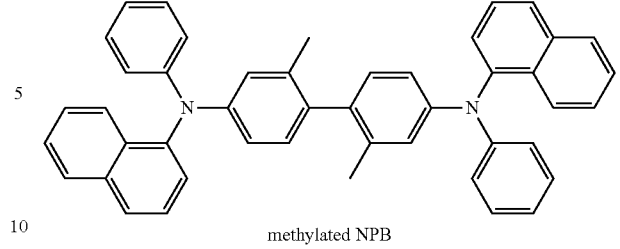

methylated NPB

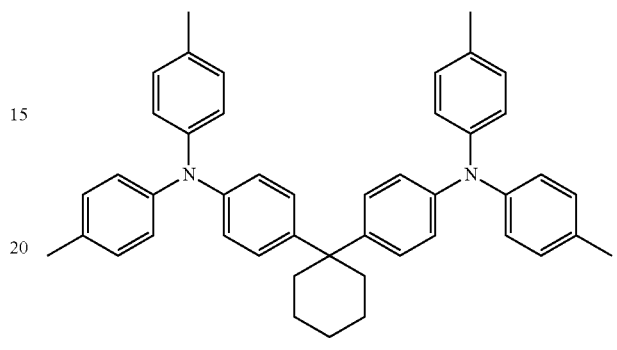

TAPC

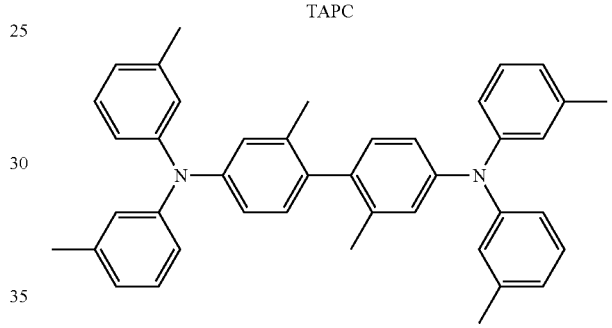

HMTPD

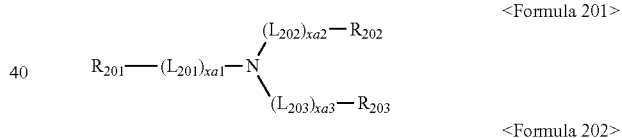

<Formula 201>

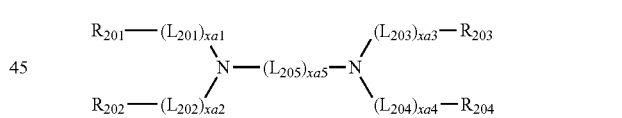

<Formula 202>

In Formulae 201 and 202, $L_{201}$ to $L_{204}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), wherein $Q_{31}$ to $Q_{33}$ are the same as described above.

In one or more embodiments, at least one from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with F, a naphthyl group, a fluorenyl group, a spiro-bifluorenyl group, a carbazolyl group, a dibenzofuranyl group, and a dibenzothiophenyl group.

In one or more embodiments, i) $R_{201}$ and $R_{202}$ in Formula 202 may be linked via a single bond, and/or ii) $R_{203}$ and $R_{204}$ may be linked via a single bond.

In one or more embodiments, at least one from $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with F, a naphthyl group, a fluorenyl group, a spiro-bifluorenyl group, a carbazolyl group, a dibenzofuranyl group, and a dibenzothiophenyl group.

The compound represented by Formula 201 may be represented by Formula 201A:

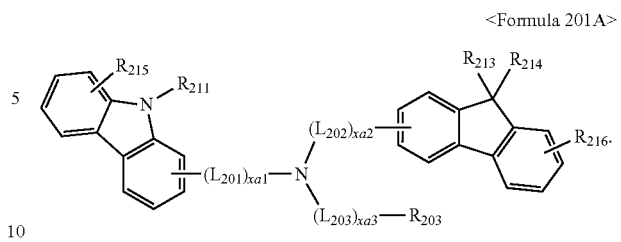

<Formula 201A>

In one embodiment, the compound represented by Formula 201 may be represented by Formula 201A(1) below:

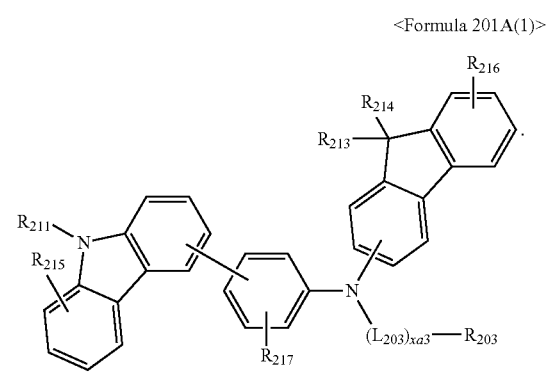

<Formula 201A(1)>

In one embodiment, the compound represented by Formula 201 may be represented by Formula 201A-1 below:

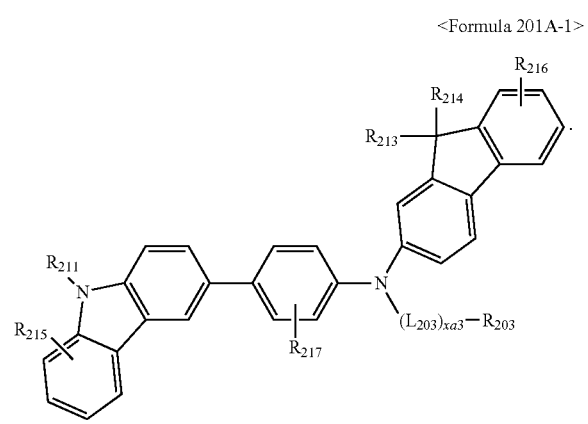

<Formula 201A-1>

In one embodiment, the compound represented by Formula 202 may be represented by Formula 202A:

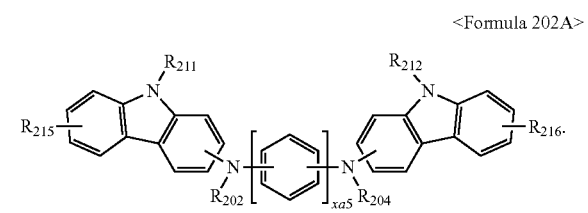

<Formula 202A>

In one embodiment, the compound represented by Formula 202 may be represented by Formula 202A-1:

<Formula 202A-1>

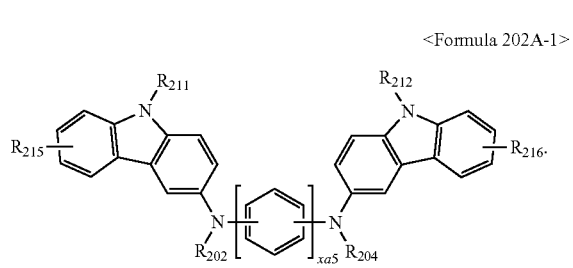

In Formulae 201A, 201A(1), 201A-1, 202A, and 202A-1, $L_{201}$ to $L_{203}$, xa1 to xa3, xa5, and $R_{202}$ to $R_{204}$ are the same as described above, $R_{211}$ and $R_{212}$ may be the same as described in connection with $R_{203}$.

$R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39:

HT1

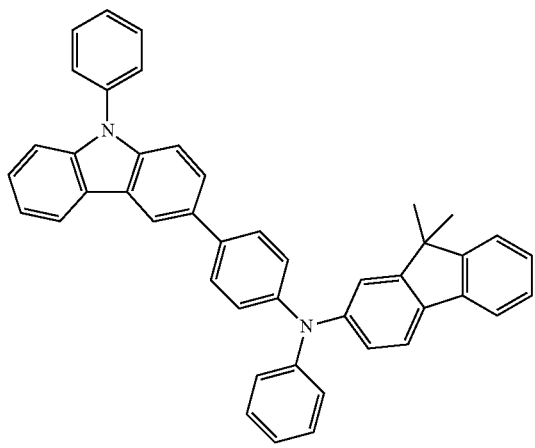

HT2

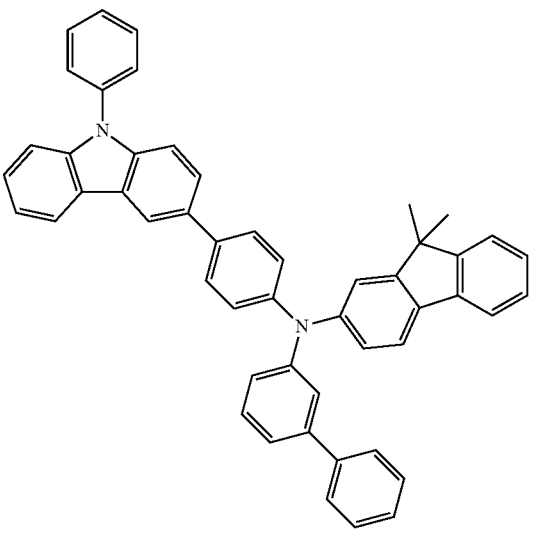

HT3

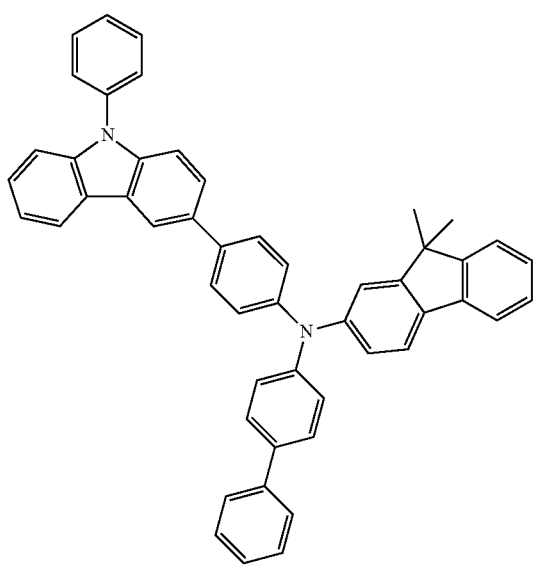

HT4

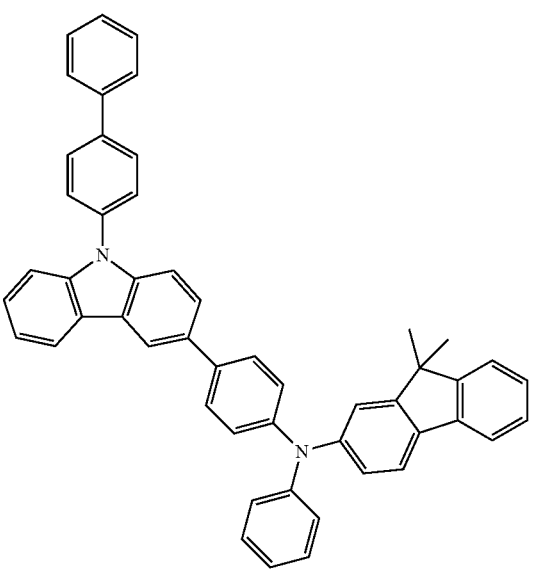

-continued
HT5
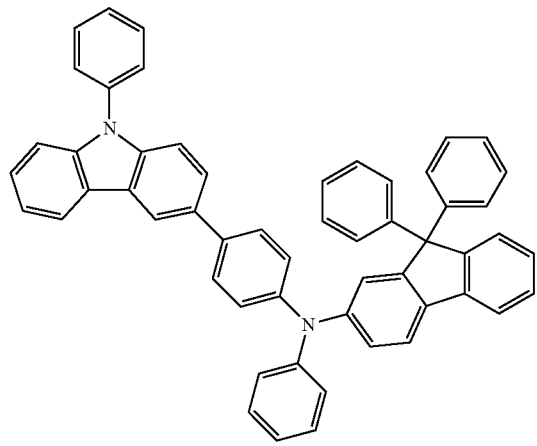
HT6
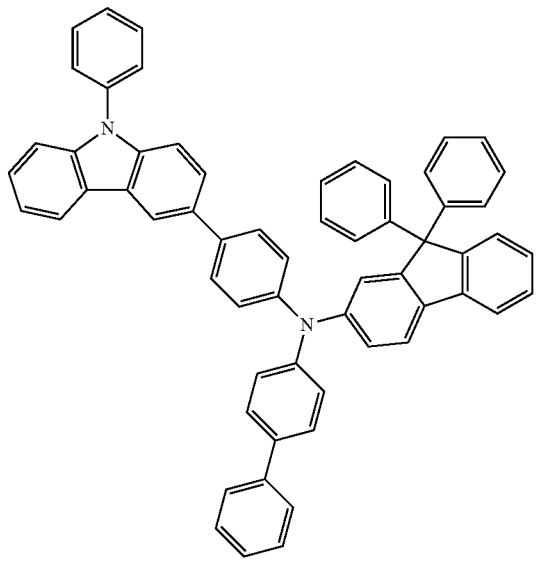
HT7
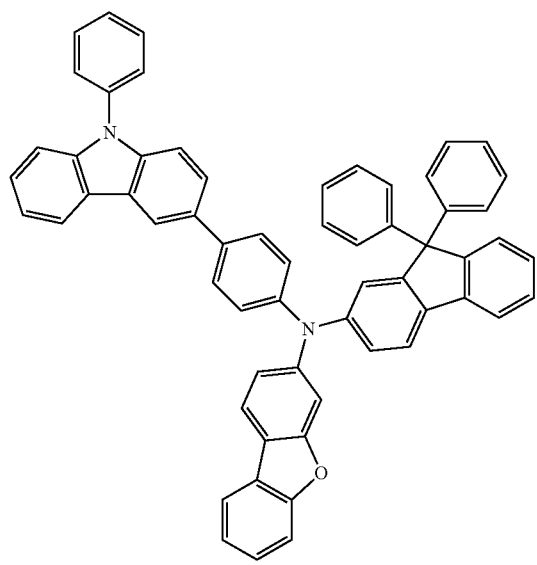
HT8
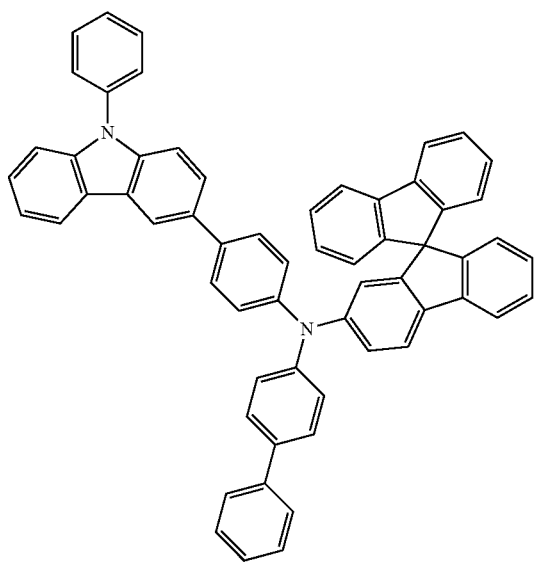

-continued
HT9
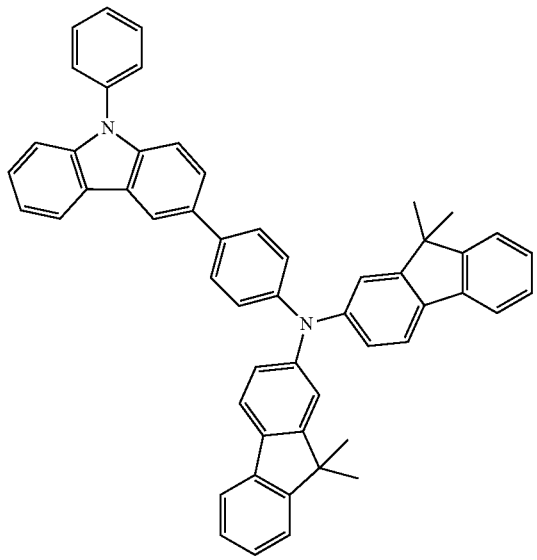
HT10
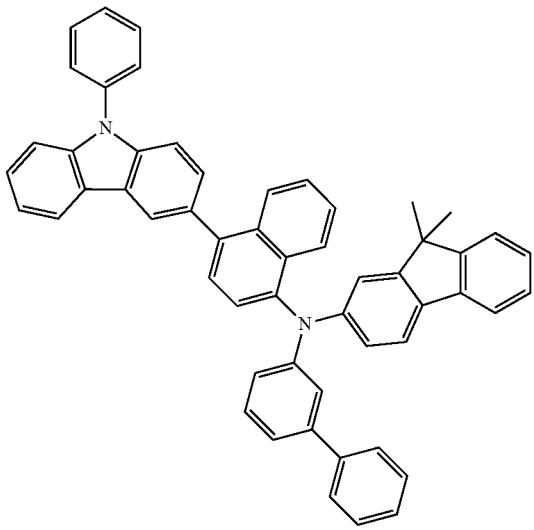
HT11
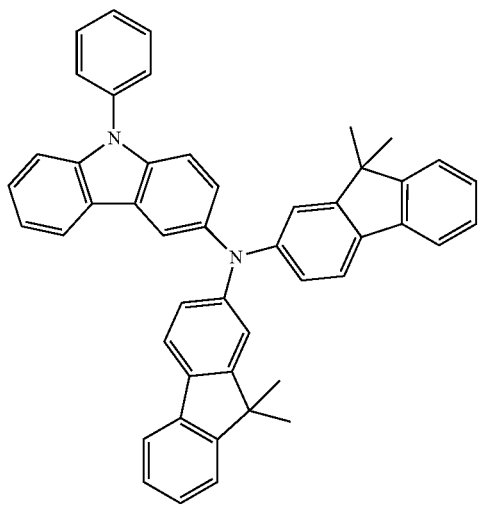
HT12
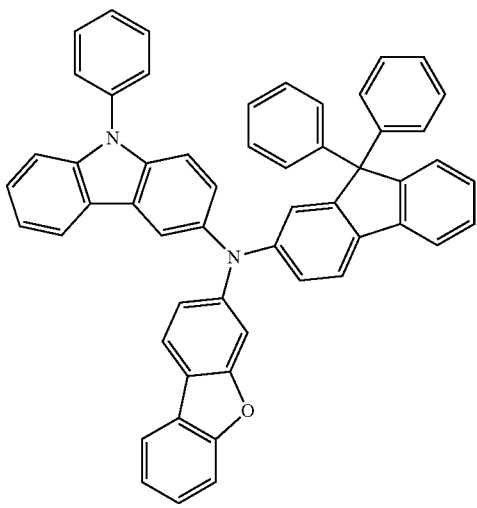
HT13
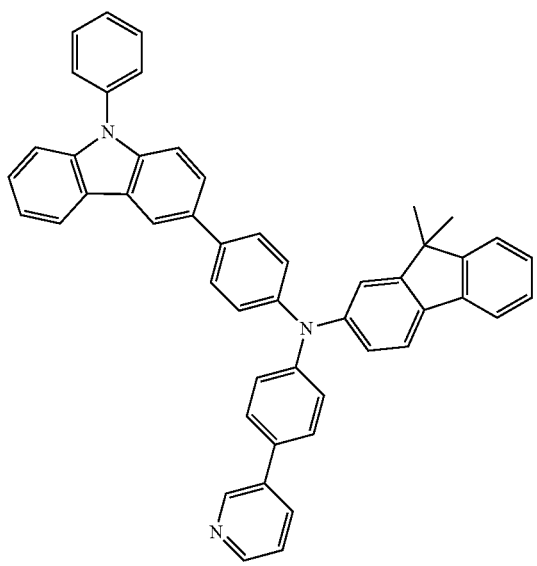
HT14
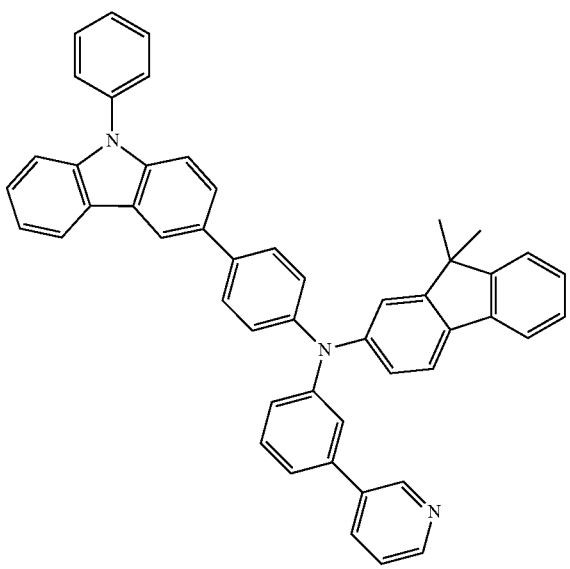

-continued
HT15
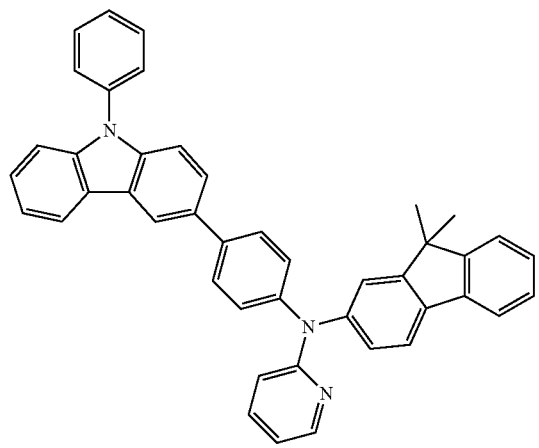
HT16
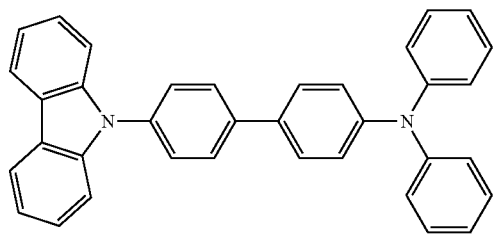
HT17
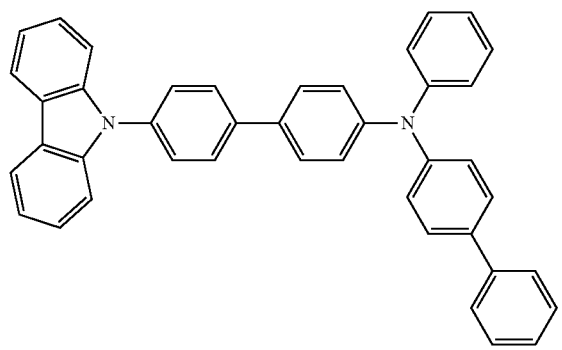
HT18
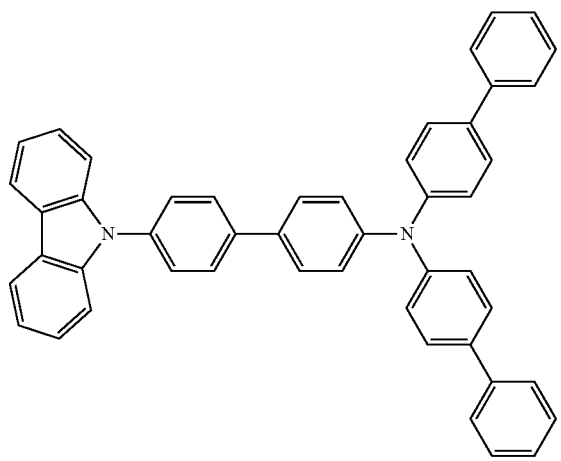
HT19
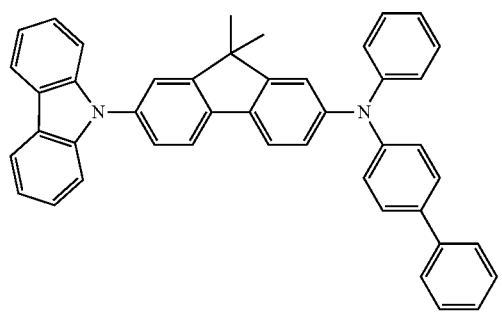
HT20
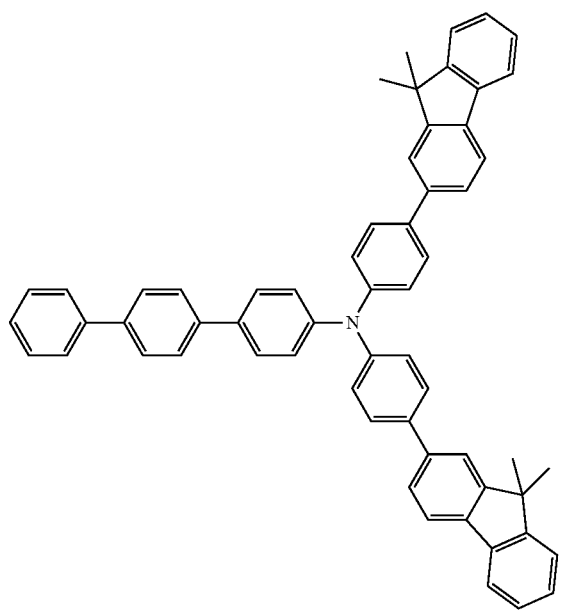

-continued
HT21
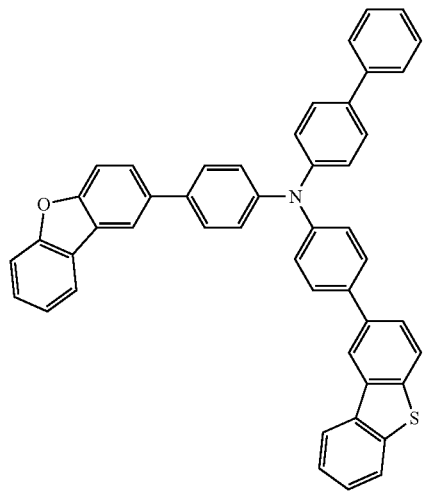
HT22
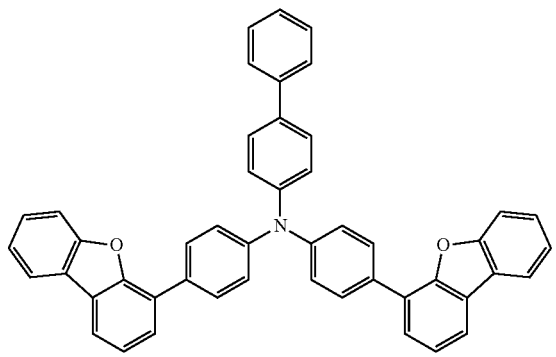
HT23
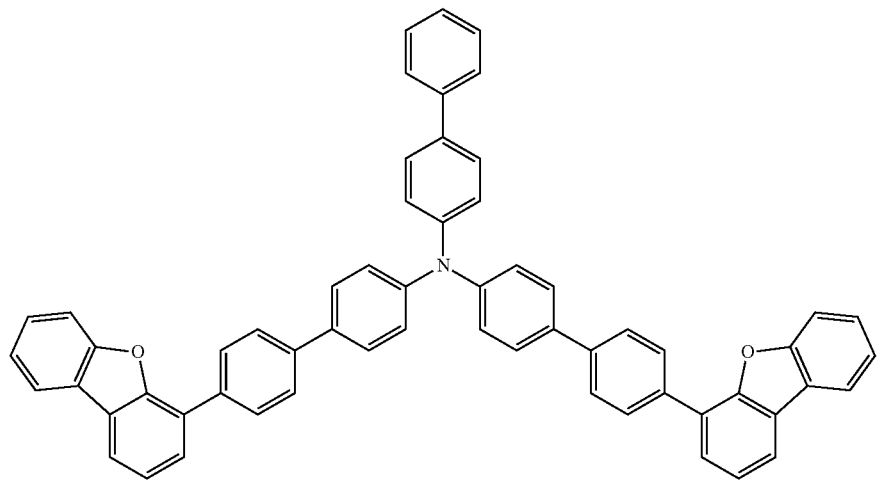
HT24
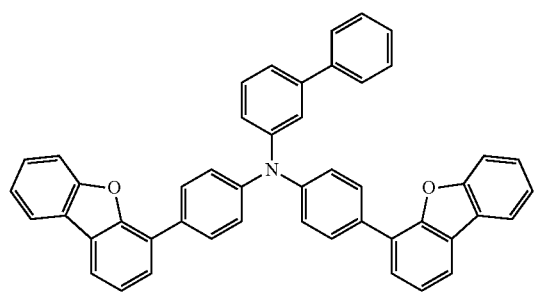
HT25
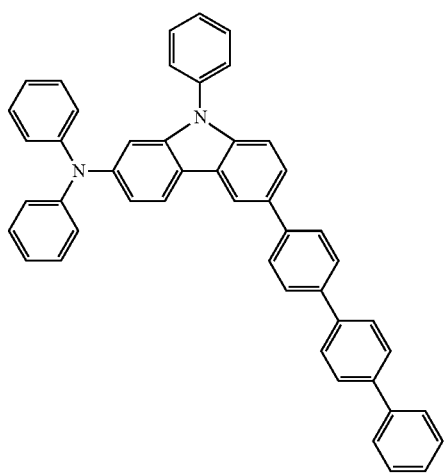

-continued
HT26
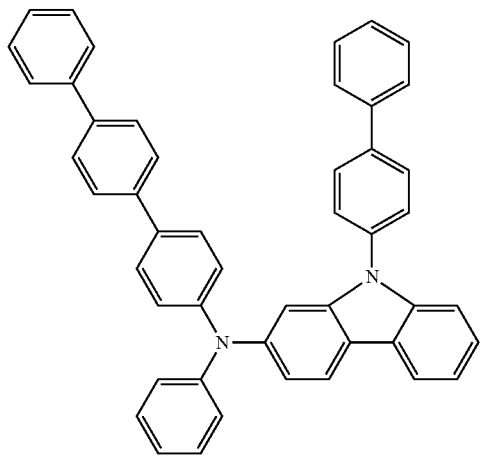
HT27
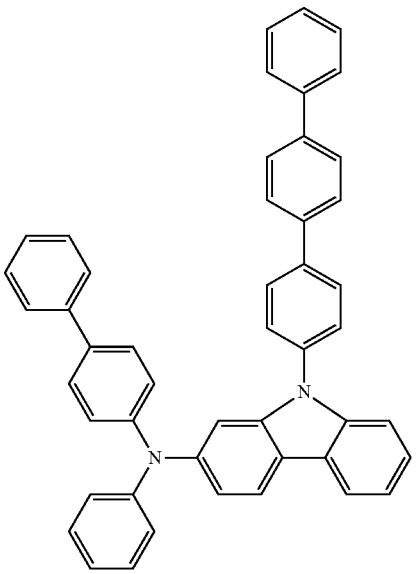
HT28
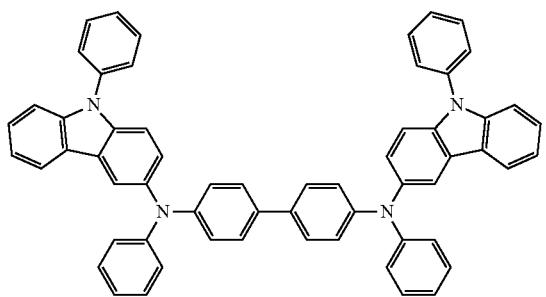
HT29
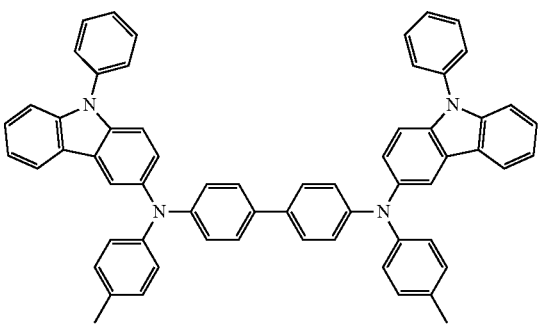
HT30
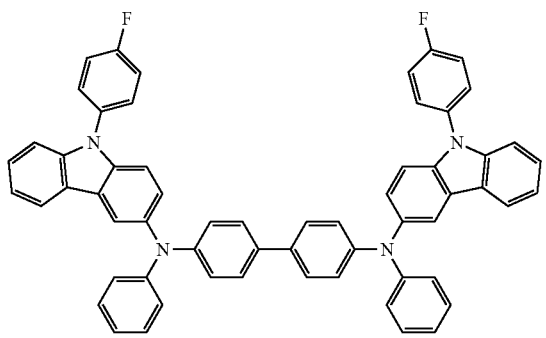
HT31
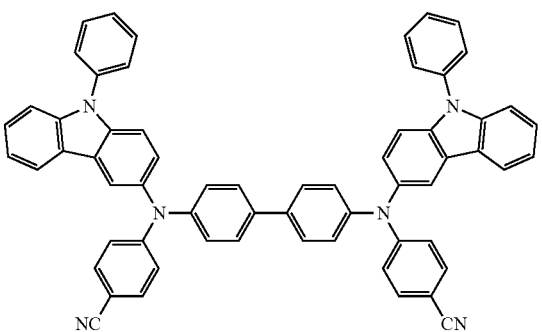

-continued
HT32
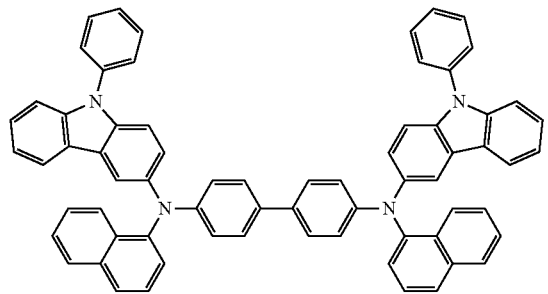
HT33
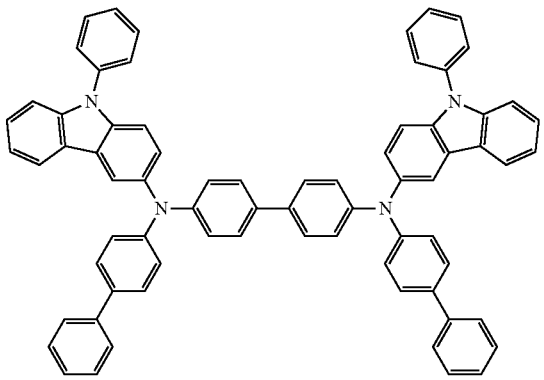
HT34
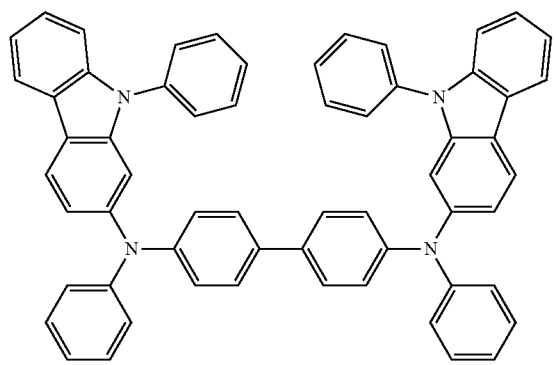
HT35
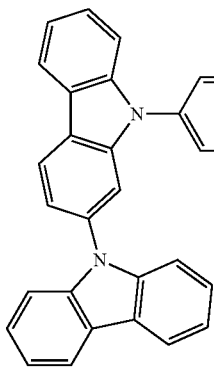
HT36
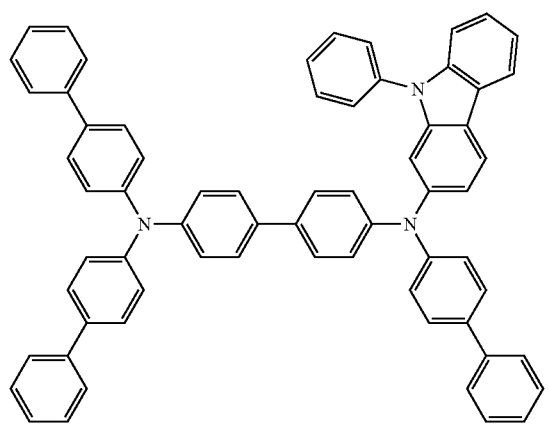
HT37
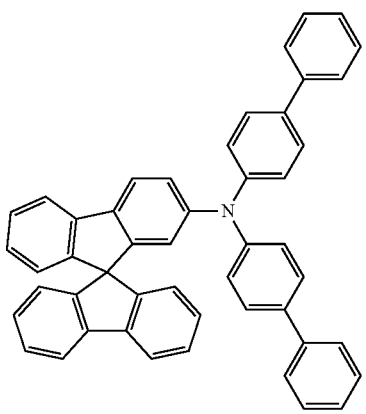

HT38

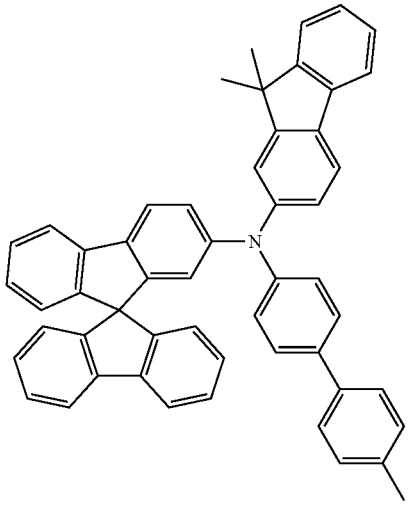

HT39

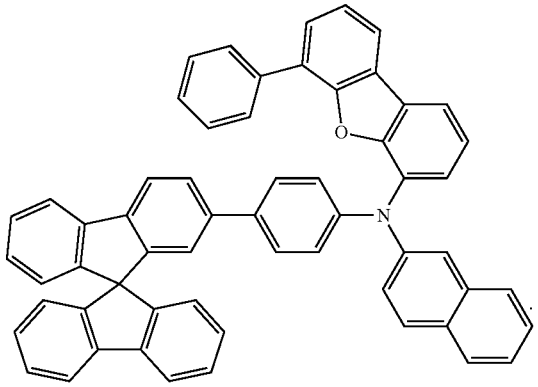

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, a lowest unoccupied molecular orbital (LUMO) of the p-dopant may be −3.5 eV or less.

The p-dopant may include at least one selected from a quinone derivative, a metal oxide, and a cyano group-containing compound.

For example, the p-dopant may include at least one selected from:

a quinone derivative, such as tetracyanoquinodimethane (TCNQ) and 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221 below:

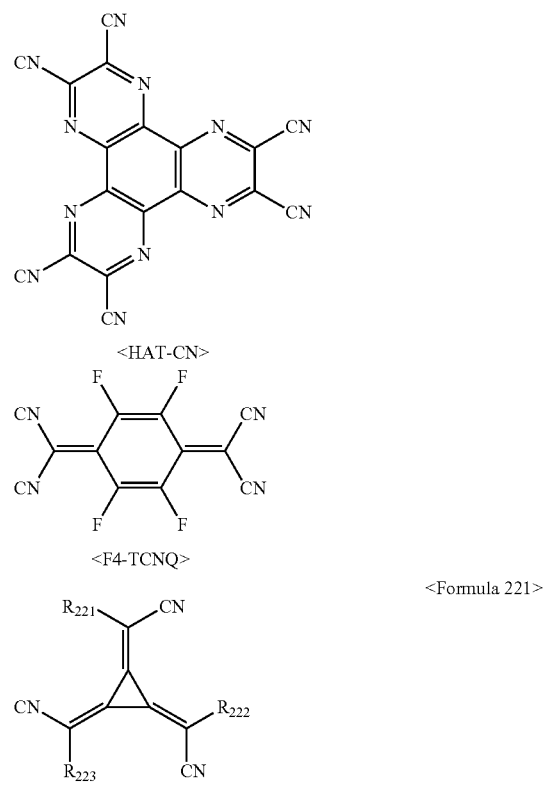

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that at least one selected from $R_{221}$ to $R_{223}$ has at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

When the organic light-emitting device 10 is a full color organic light-emitting device, the emission layer may be patterned into a red emission layer, a green emission layer, or a blue emission layer, according to a sub pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red-light emission material, a green-light emission material, and a blue-light emission material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be, e.g., in a range of about 0.01 to about 15 parts by weight based on 100 parts by weight of the host.

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

In one or more embodiments, the host may further include, the condensed cyclic compound represented by Formula 1, a compound represented by Formula 301 below:

$$[Ar_{301}]_{xb11}\text{-}[(L_{301})_{xb1}\text{-}R_{301}]_{xb21}. \qquad \text{<Formula 301>}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xb1 may be an integer selected from 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$), and xb21 may be an integer selected from 1 to 5, wherein $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group.

In one embodiment, $Ar_{301}$ in Formula 301 may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xb11 in Formula 301 is two or more, two or more $Ar_{301}$(s) may be linked via a single bond.

In one or more embodiments, the organometallic compound represented by Formulae 301 may be represented by Formulae 301-1 or 301-2:

<Formula 301-1>

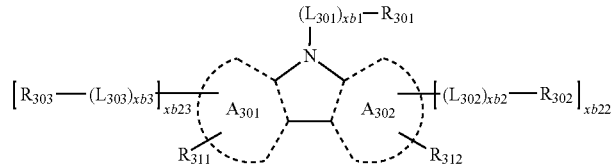

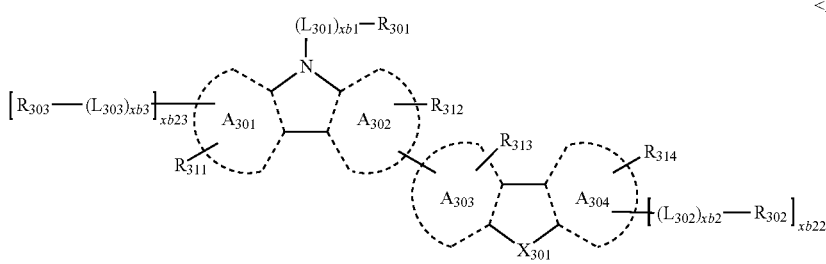

<Formula 301-2>

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[$(L_{304})_{xb4}$-$R_{304}$], $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2, $L_{301}$, xb1, $R_{301}$ and $Q_{31}$ to $Q_{33}$ may be the same as described above, $L_{302}$ to $L_{304}$ may each independently be the same as described in connection with $L_{301}$, Xb2 to xb4 may each independently be the same as described in connection with xb1, $R_{302}$ to $R_{304}$ may each independently be the same as described in connection with $R_{301}$.

For example, $L_{301}$ to $L_{30z}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ are the same as described above.

In one embodiment, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{31}$ to $Q_{33}$ may be the same as described above.

In one or more embodiments, the host may include an alkaline-earth metal complex. For example, the host may be selected from a Be complex (for example, Compound H55), an Mg complex, and a Zn complex.

The host may include, in addition to the heterocyclic compound, at least one selected from 9,10-di(2-naphthyl) anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and a Compounds H1 to H55:

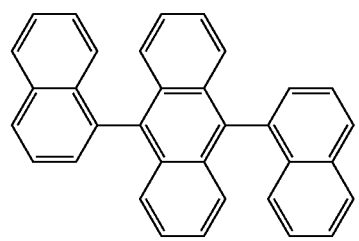

H1

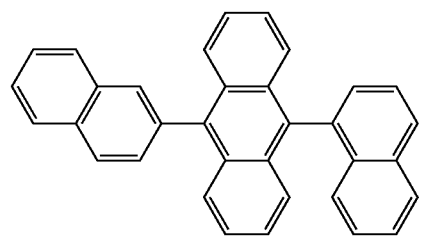

H2

H3
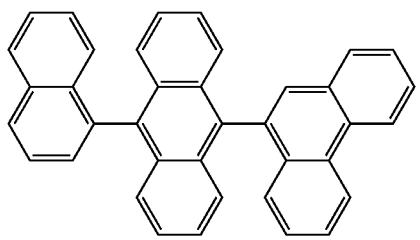
H4
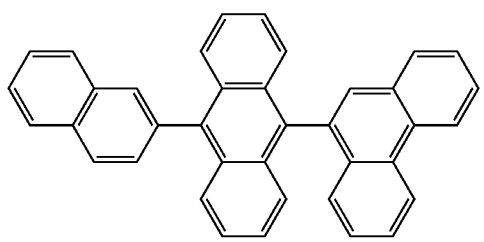
H5
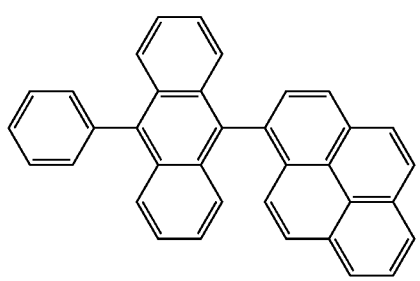
H9
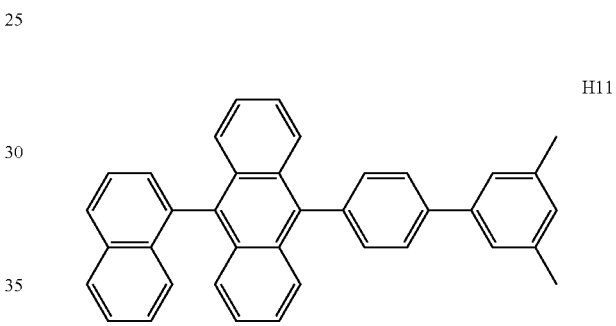
H6
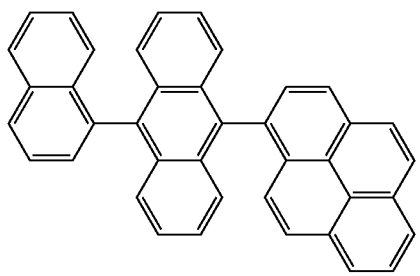
H10
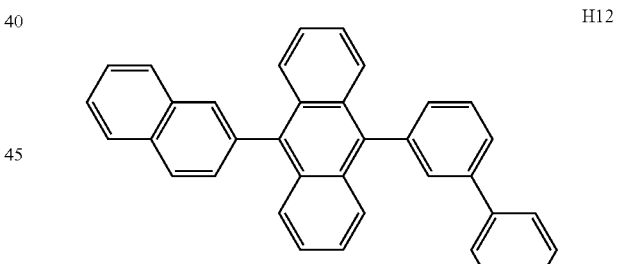
H7
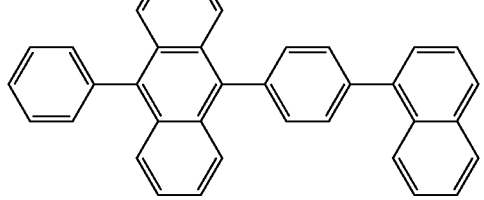
H11
H8
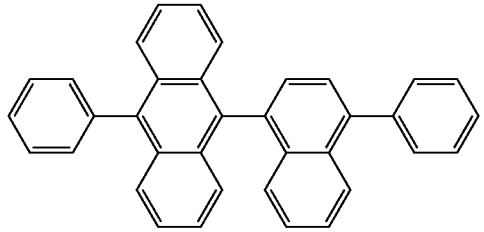
H12
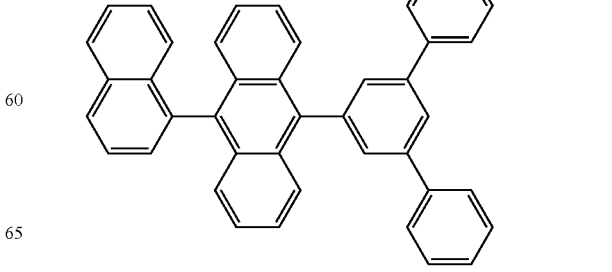
H13
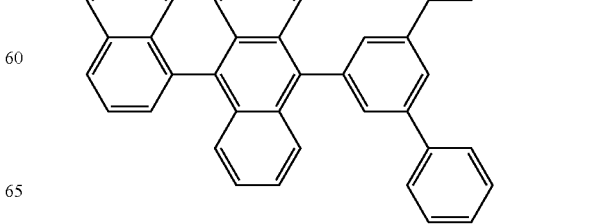

H14
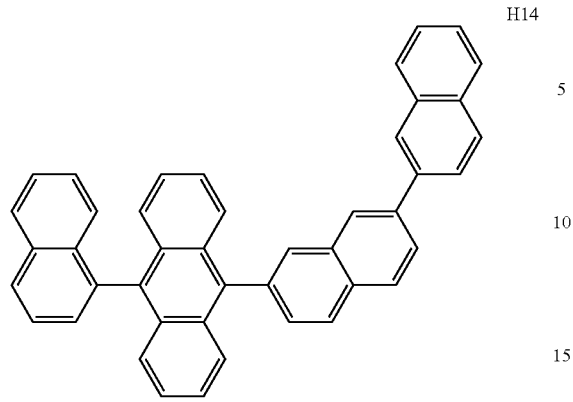
H15
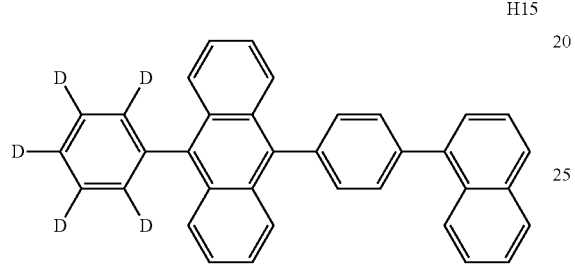
H16
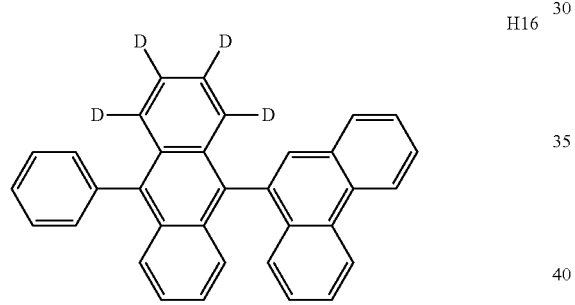
H17
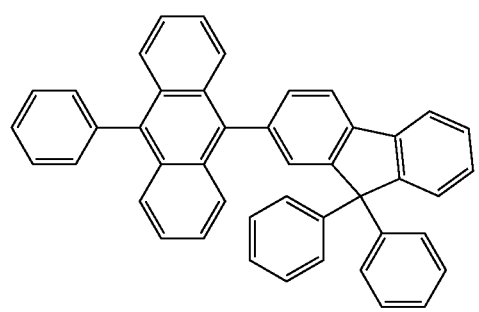
H18
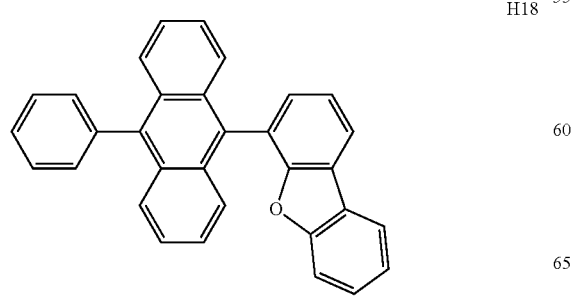
H19
H20
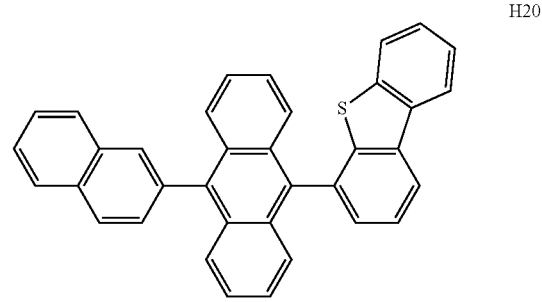
H21
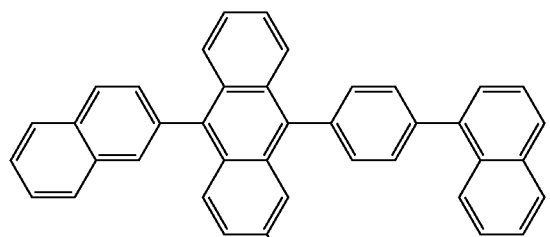
H22
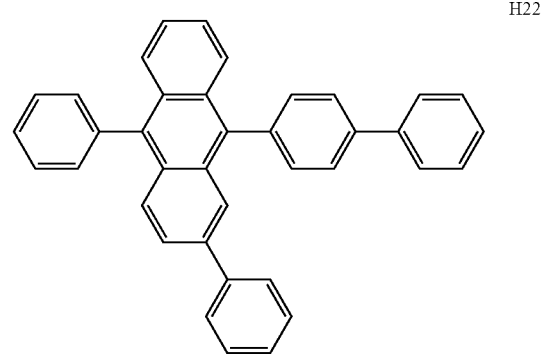

H23
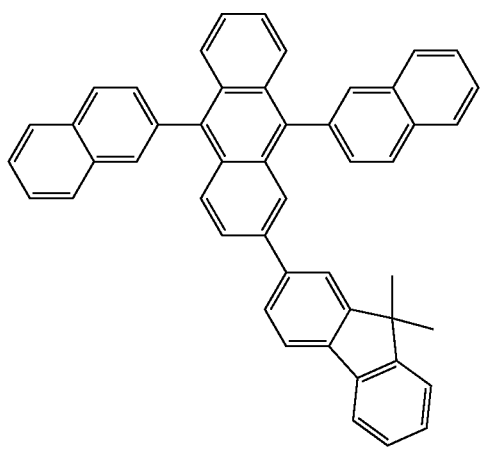
H24
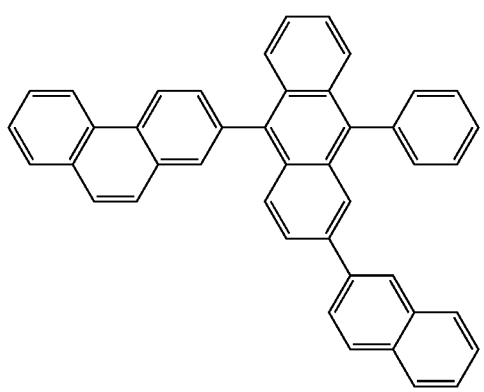
H25
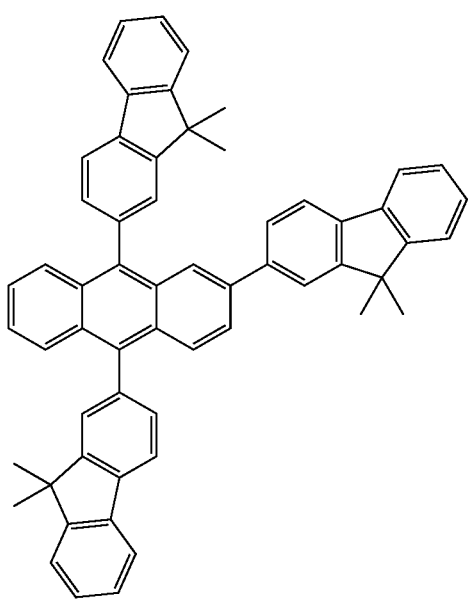
H26
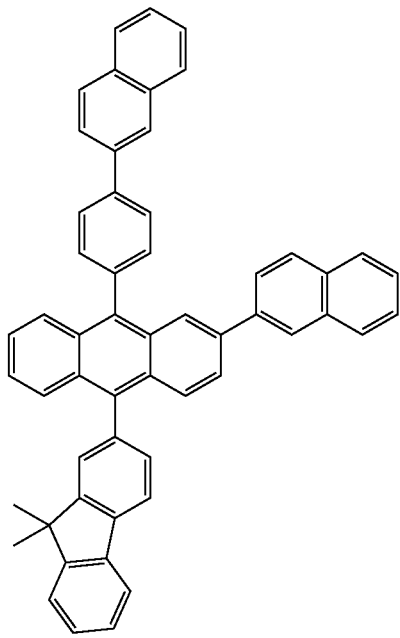
H27
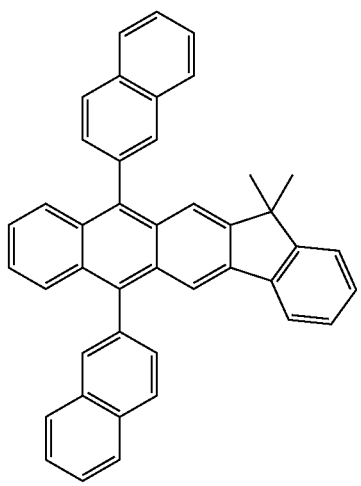
H28
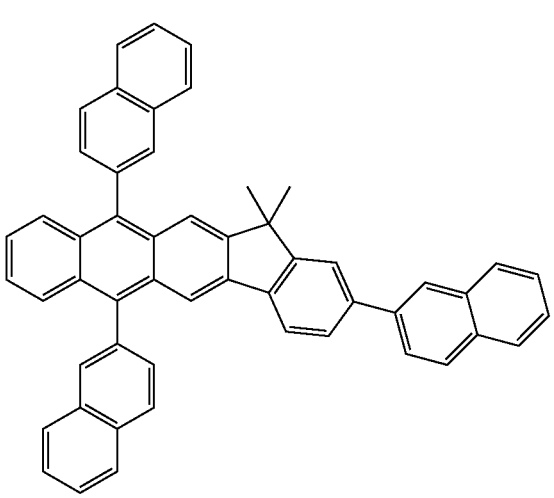

H29
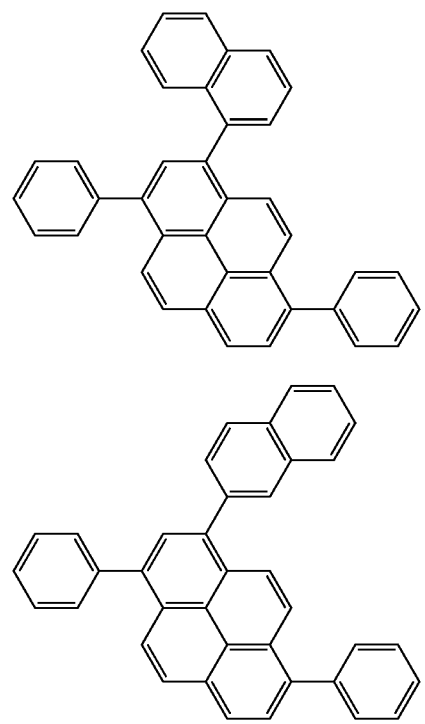
H30
H31
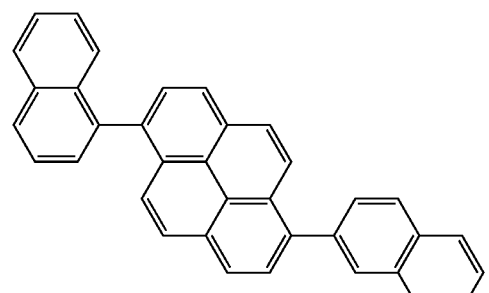
H32
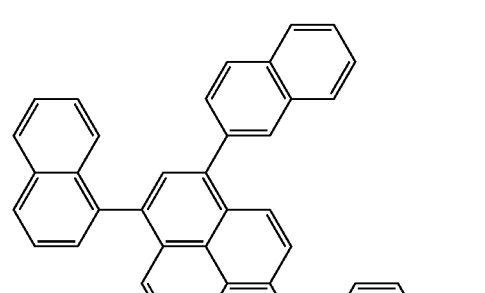
H33
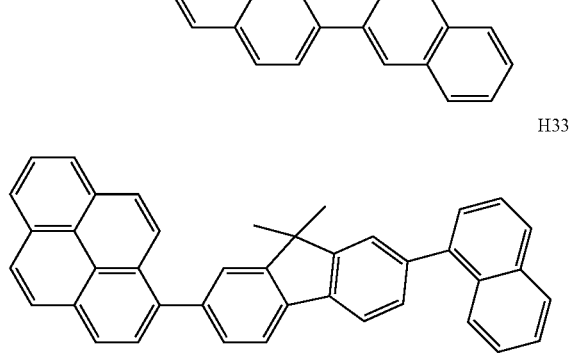
H34
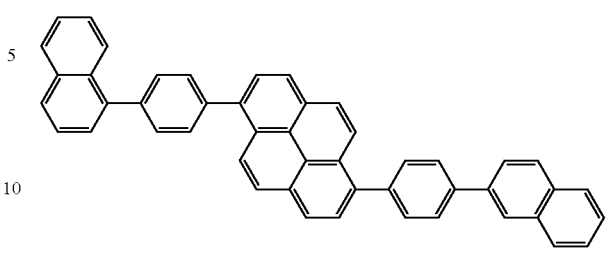
H35
H36
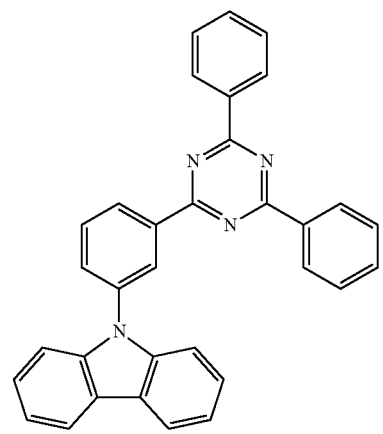
H37
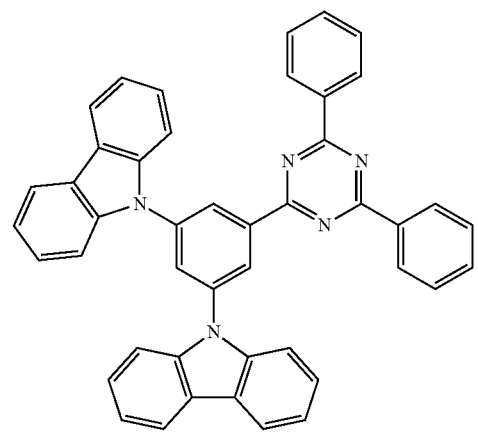

87
-continued
H38
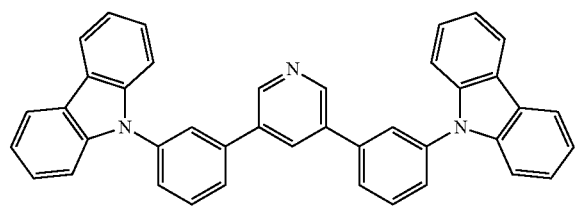
H39
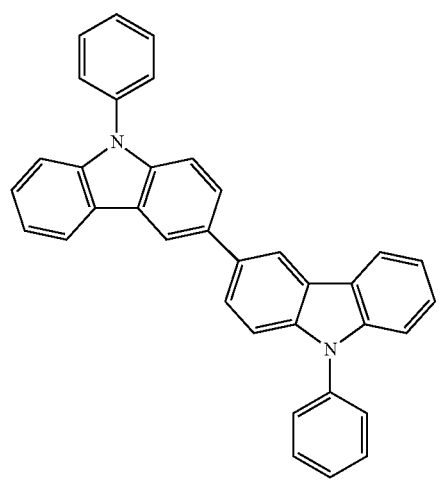
H40
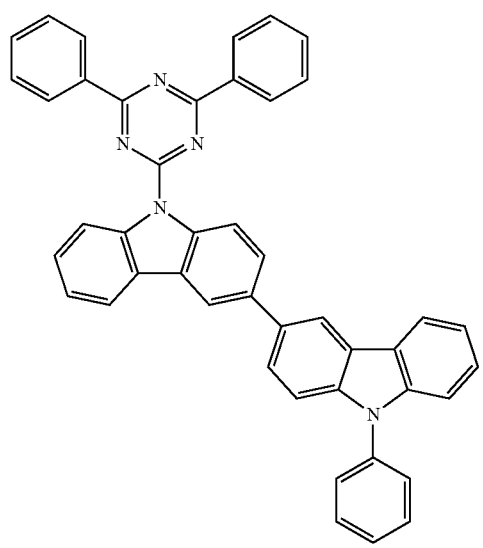
88
-continued
H41
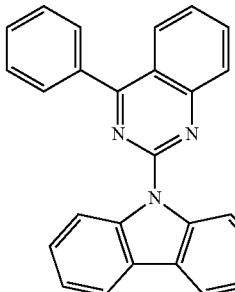
H42
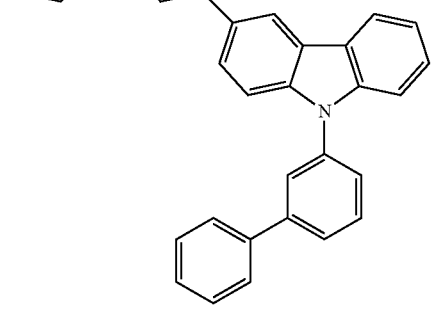
H43
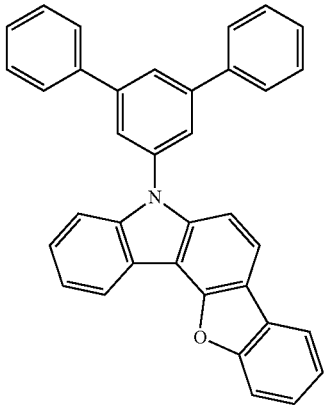
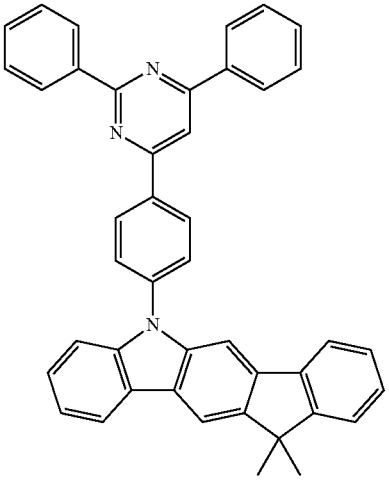

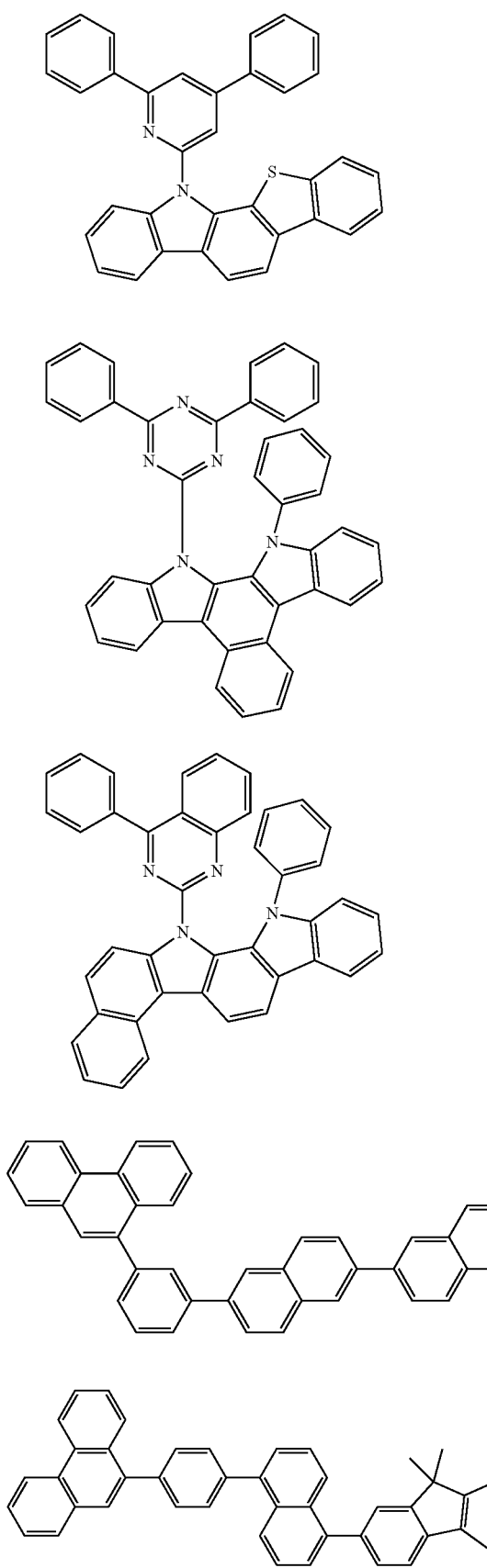
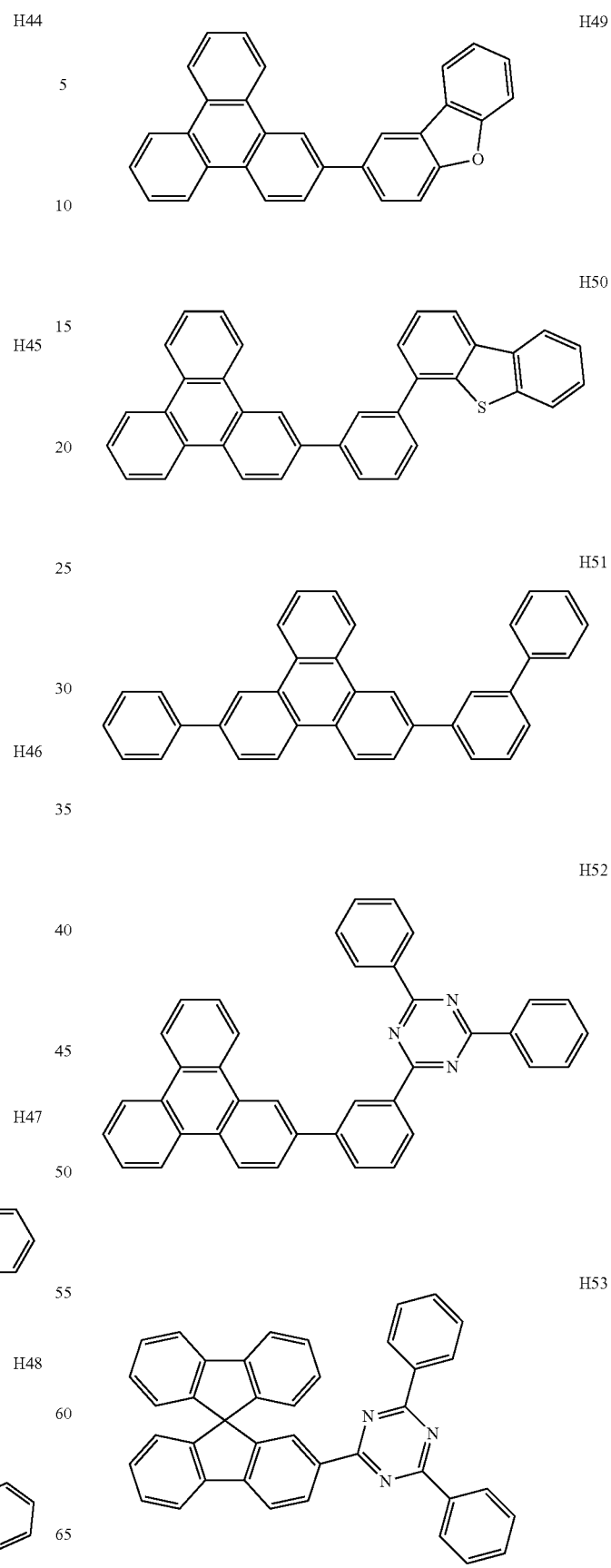

-continued

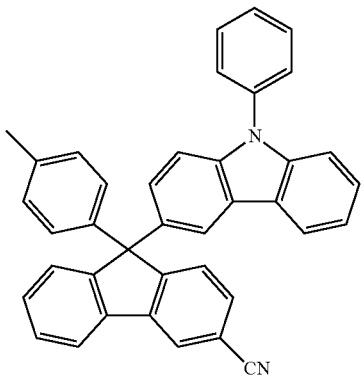
H54

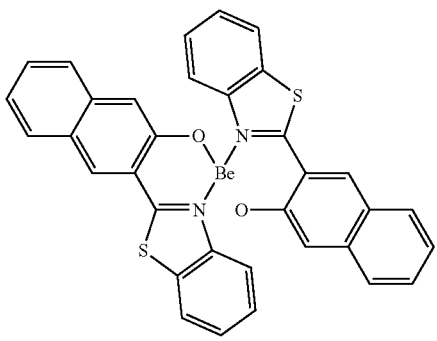
H55

The dopant may further include, in addition to the heterocyclic compound, a phosphorescent dopant or a fluorescent dopant which are to be described below.

The phosphorescent dopant may include an organometallic complex represented by Formula 401:

$$M(L_{401})_{xc1}(L_{402})_{xc2} \quad \text{<Formula 401>}$$

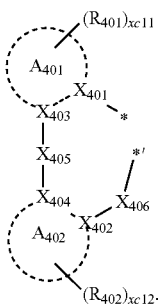

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein, when xc1 is two or more, two or more $L_{401}(s)$ may be identical to or different from each other, $L_{402}$ may be an organic ligand, and xc2 may be an integer selected from 0 to 4, wherein when xc2 is two or more, two or more $L_{402}(s)$ may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be selected from a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)—*', *—C($Q_{411}$)($Q_{412}$)-', *—C($Q_{411}$)=C($Q_{412}$)-*', *—C($Q_{411}$)=*', or *—C($Q_{411}$)=*', wherein $Q_{411}$ and $Q_{412}$ may be hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer selected from 0 to 10, and

* and *' in Formula 402 each indicate a binding site to M in Formula 401.

In one embodiment, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiments, in Formula 402, i) $X_{401}$ may be nitrogen, and $X_{402}$ may be carbon, or ii) $X_{401}$ and $X_{402}$ may each be nitrogen at the same time.

In one or more embodiments, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group. and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group.

In one or more embodiments, when xc1 in Formula 401 is two or more, two $A_{401}$(s) in two or more $L_{401}$(s) may be optionally linked via $X_{407}$, which is a linking group, or two $A_{402}$(s) in two or more $L_{401}$(s) may be optionally linked via $X_{408}$, which is a linking group (see Compounds PD1 to PD4 and PD7). $X_{407}$ and $X_{408}$ may each independently be a single bond, *—O—*', *—S—*', *—C(=O)—*', *—N($Q_{413}$)-*', *—C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group).

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O) isonitrile, —CN, and phosphorus (for example, phosphine, or phosphite).

In one or more embodiments, the phosphorescent dopant may be selected from, for example, Compounds PD1 to PD25:

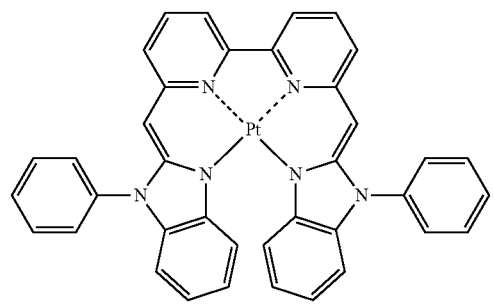

PD1

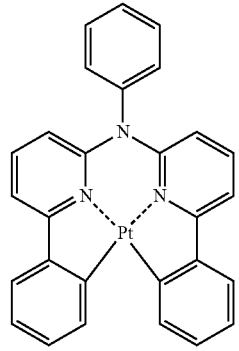

PD2

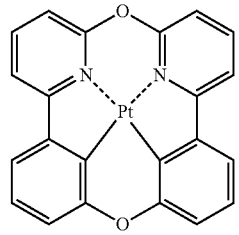

PD3

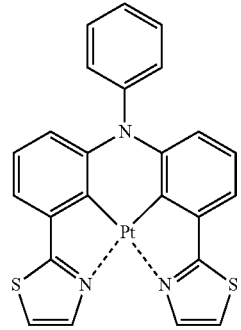

PD4

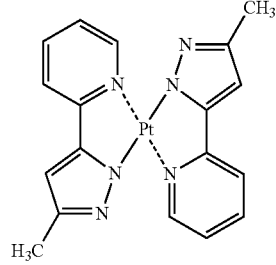

PD5

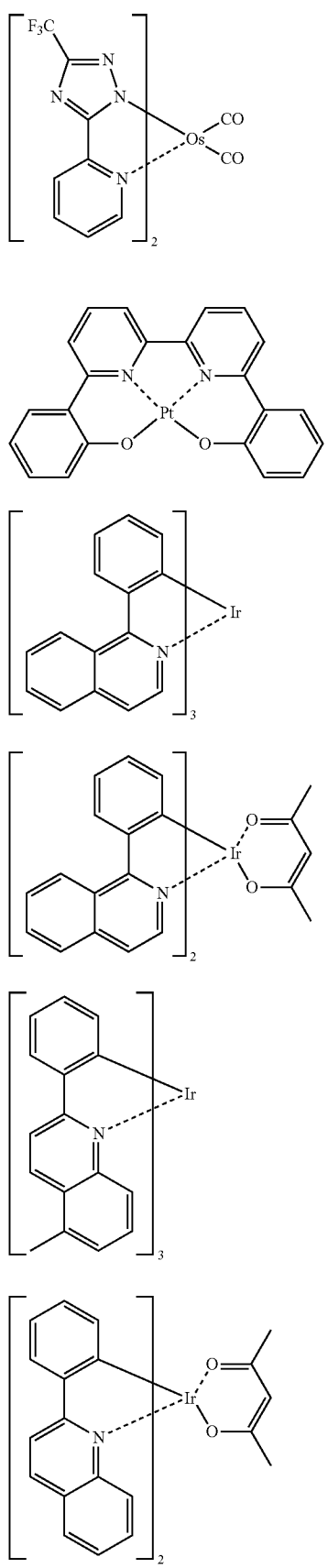

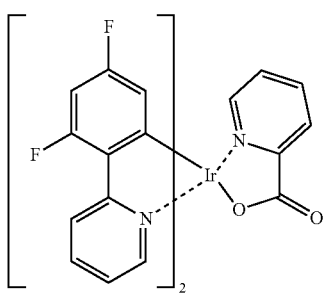 PD17
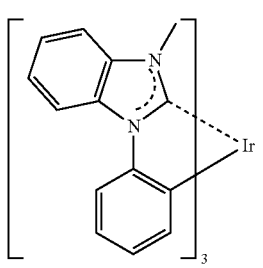 PD18
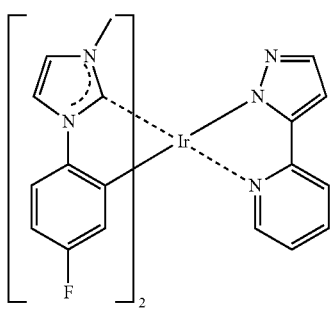 PD19
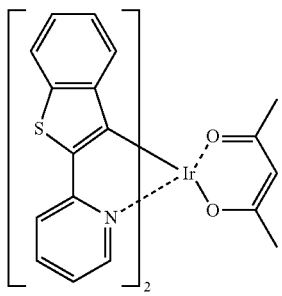 PD20
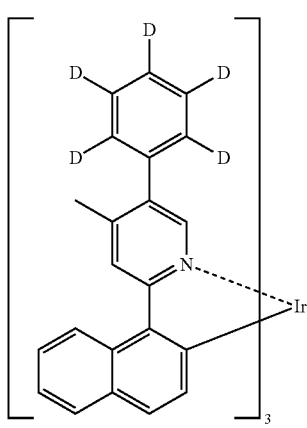 PD21
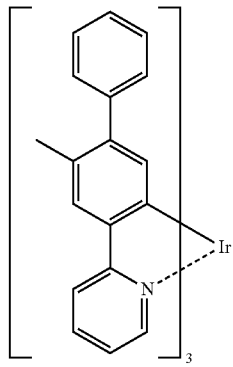 PD22
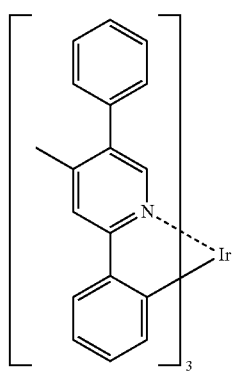 PD23
PD24
PD25
The fluorescent dopant may include an arylamine compound or a styrylamine compound.
The fluorescent dopant may include a compound represented by Formula 501 below:

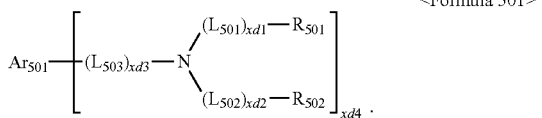
<Formula 501>

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3;

$R_{501}$ and $R_{502}$ may each independently be selected from a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, $Ar_{501}$ in Formula 501 may be selected from a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, $R_{501}$ and $R_{501}$ in Formula 502 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), wherein $Q_{31}$ to $Q_{33}$ may each be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2.

For example, the fluorescent dopant may be selected from Compounds FD1 to FD22:

FD1

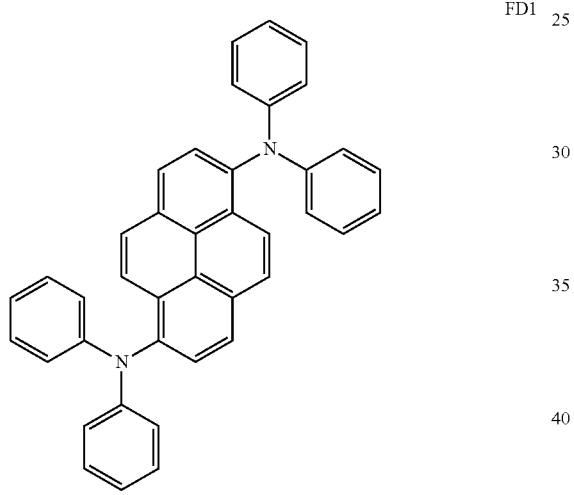

FD2

FD3

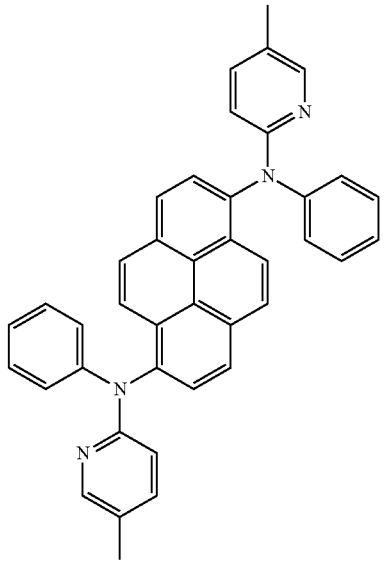

FD4

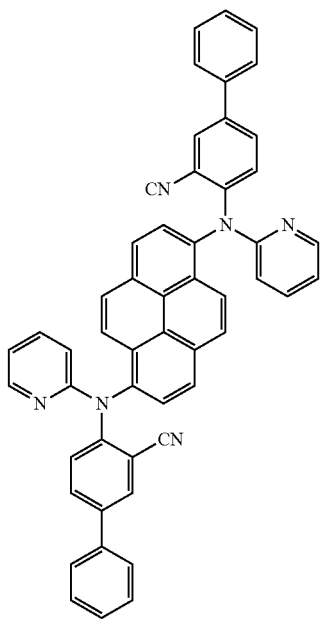

FD5
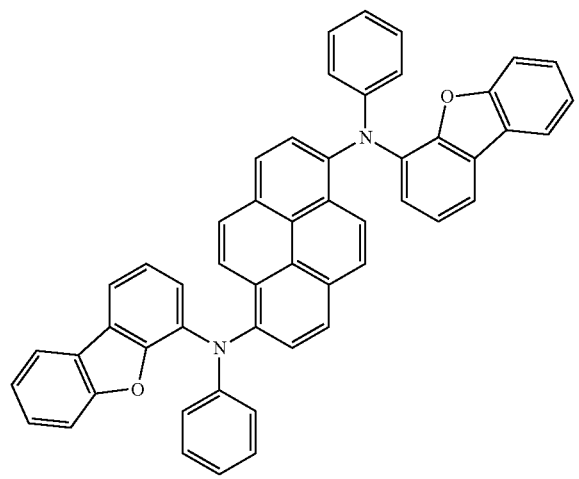
FD6
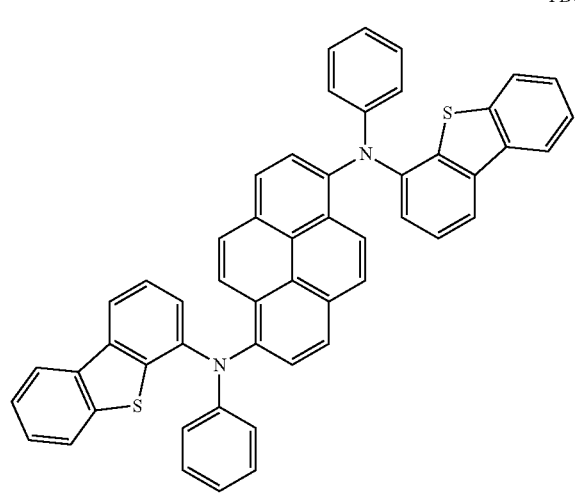
FD7
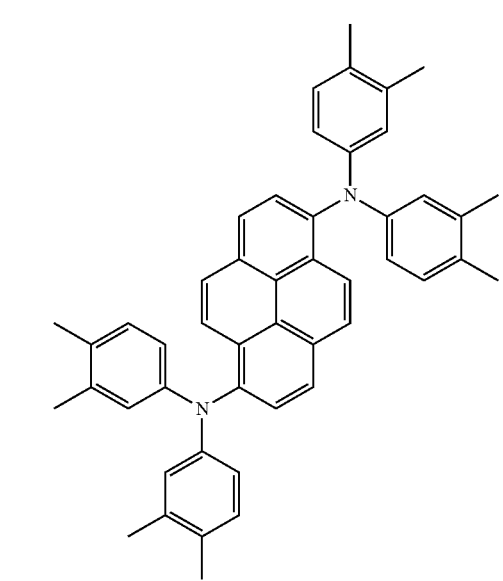
FD8
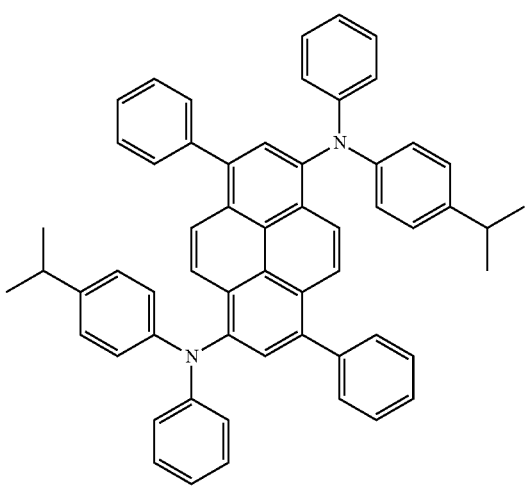
FD9
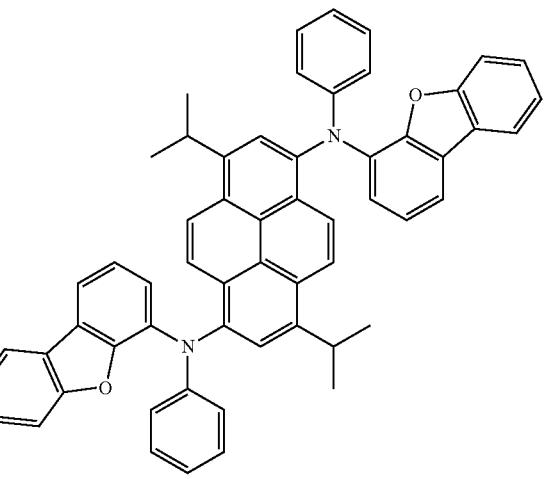
FD10
FD11
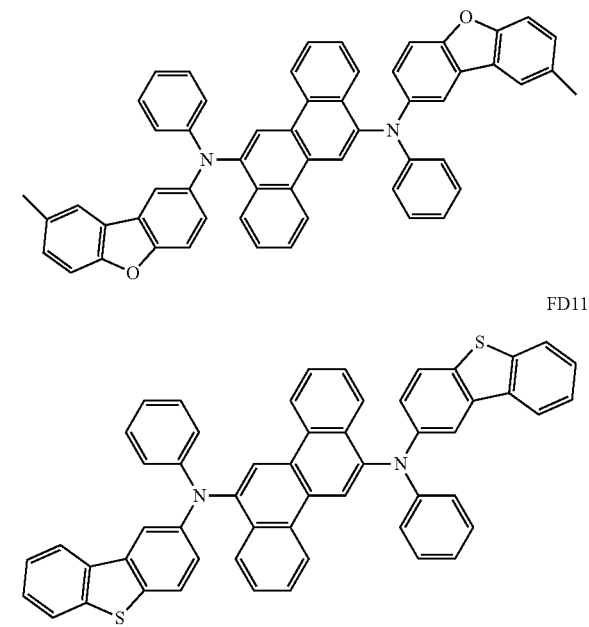

FD12
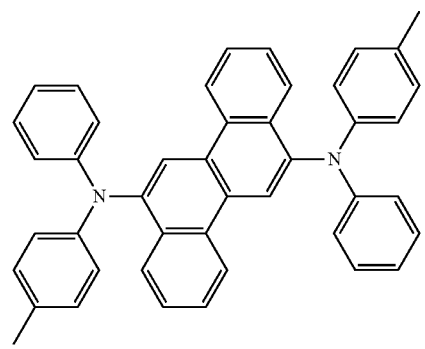
FD13
FD14
FD15
FD16
FD17
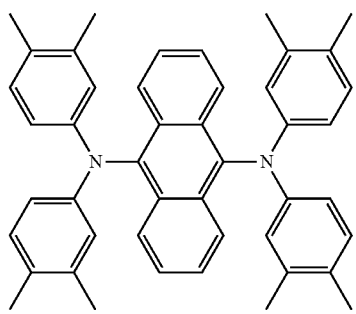
FD18
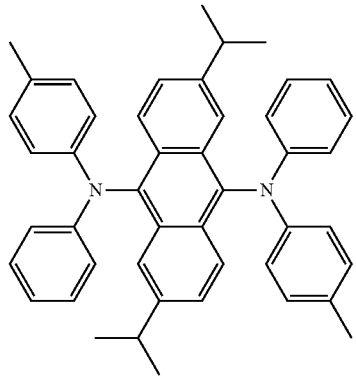
FD19
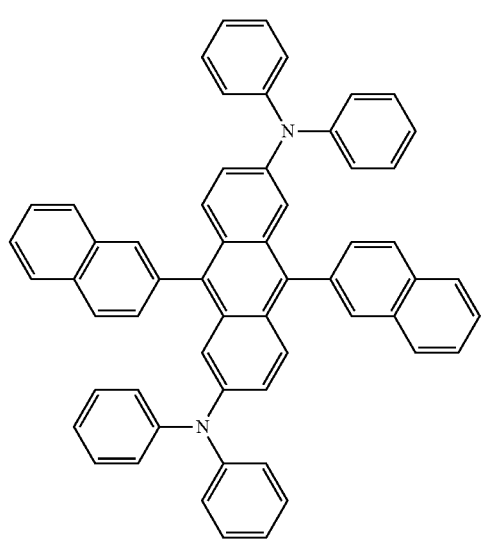
FD20
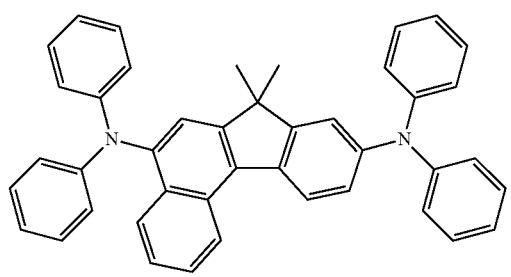

-continued
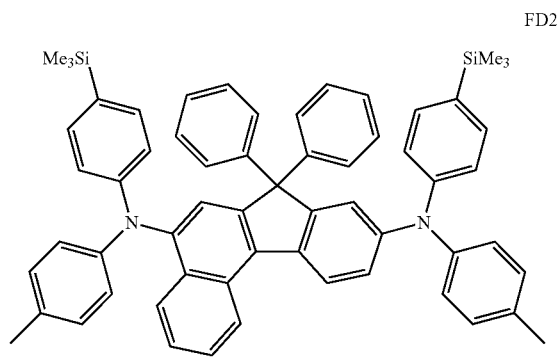
FD21
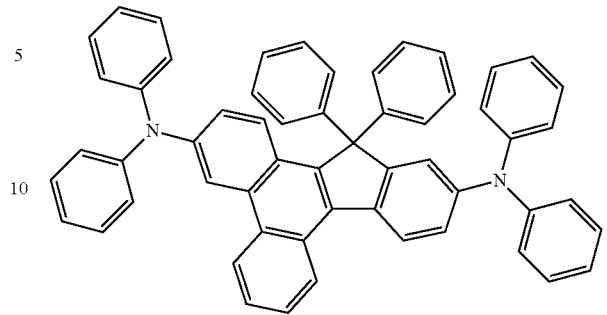
FD22
In one or more embodiments, the fluorescent dopant may be selected from the following compounds.
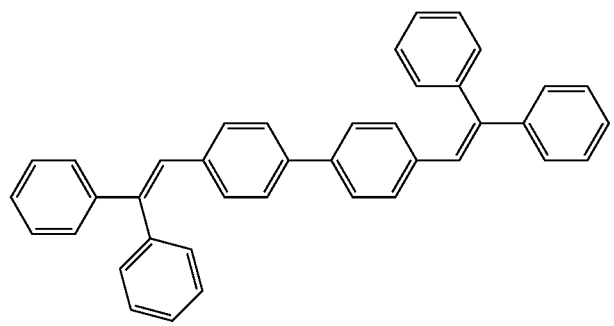
DPVBi
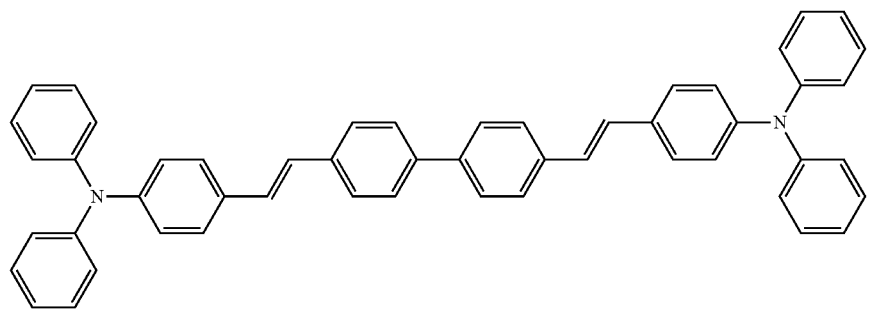
DPAVBi
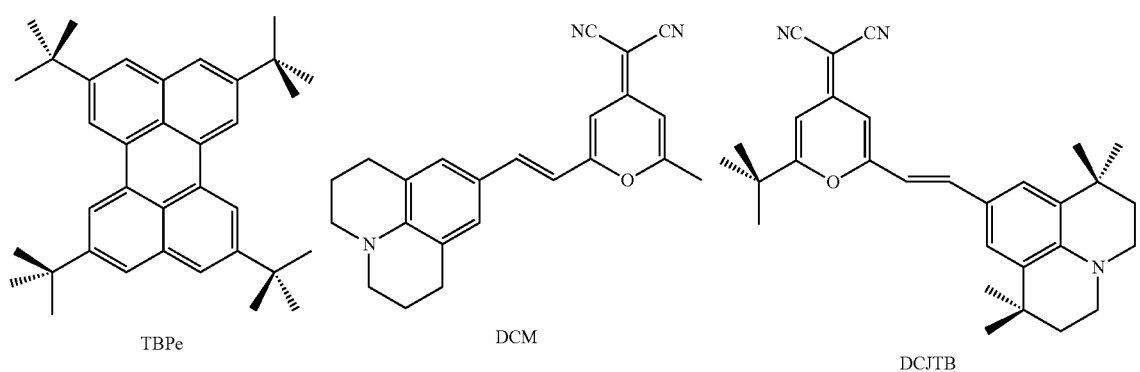
TBPe  DCM  DCJTB

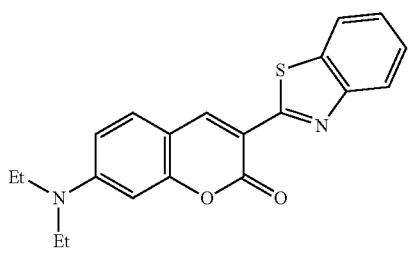

Coumarin 6

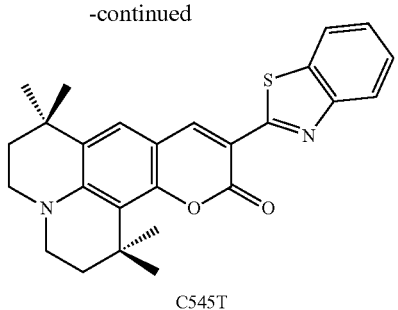

C545T

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer.

The electron transport region (for example, a buffer layer, a hole blocking layer, an electron control layer, or an electron transport layer in the electron transport region) may include a metal-free compound containing at least one π electron-depleted nitrogen-containing ring.

The "at electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 60-membered to 7-membered hetero monocyclic group having at least one *—N=*' moiety, ii) a heteropoly cyclic group in which two or more 5-membered to 7-membered hetero monocyclic groups each having at least one *—N=*' moiety are condensed with each other, or iii) a heteropoly cyclic group in which at least one of 5-membered to 7-membered hetero monocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole.

In one embodiment, the electron transport region may further include, in addition to the heterocyclic compound represented by Formula 1, a compound represented by Formula 601.

$[Ar_{601}]_{xe11}$-$[(L_{601})_{xe1}$-$R_{601}]_{xe21}$.   <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xe1 may be an integer selected from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$) and —P(=O)($Q_{601}$)($Q_{602}$), wherein $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer selected from 1 to 5.

In one embodiment, at least one of $Ar_{601}$(s) in the number of xe11 and/or at least one of $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a Spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, phenanthroline group, phenazine group, a benzimidazole group, an isobenzothiazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, naphthyridine group, a quinoxaline group, a quinazoline group, a cinnoline group, a phenanthridine group, an acridine group, phenanthroline group, phenazine group, a benzimidazole group, an isobenzothiazole group, a benzoxazole group, an isobenzoxazole group, a triazole group, a tetrazole group, an oxadiazole group, a triazine group, thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar$_{601}$(s) may be linked via a single bond.

In one or more embodiments, Ar$_{601}$ in Formula 601 may be an anthracene group.

In one or more embodiments, a compound represented by Formula 601 may be represented by Formula 601-1:

<Formula 601-1>

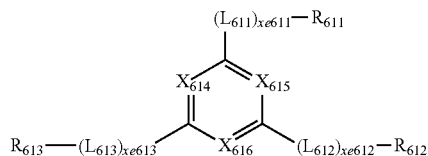

In Formula 601-1, $X_{614}$ may be N or C($R_{614}$), $X_{615}$ may be N or C($R_{615}$), $X_{616}$ may be N or C($R_{616}$), and at least one selected from $X_{614}$ to $X_{616}$ may be N, $L_{611}$ to $L_{613}$ may be each independently substantially the same as described in connection with $L_{601}$, xe611 to xe613 may be each independently substantially the same as described in connection with xe1, $R_{611}$ to $R_{613}$ may be each independently substantially the same as described in connection with $R_{601}$, $R_{614}$ to $R_{616}$ may each independently be selected from hydrogen, deuterium, —F, —Cl, —Br, —I, a hydroxyl-group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formula 601 and 601-1 may each independently be selected from a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$), and —P(=O)(Q$_{601}$)(Q$_{602}$), wherein $Q_{601}$ and $Q_{602}$ are substantially the same as described above.

The electron transport region may include at least one compound selected from Compounds ET1 to ET36:

ET1
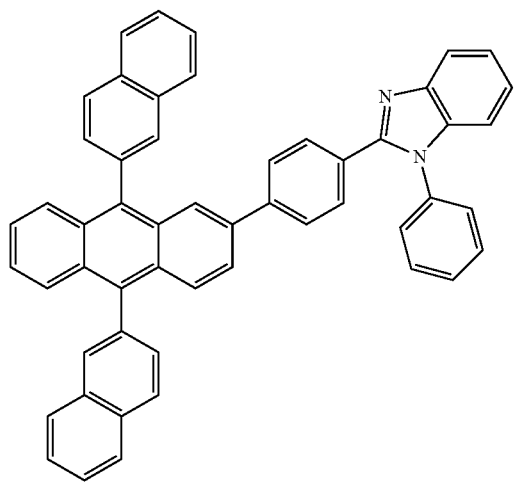
ET2
ET3
ET4
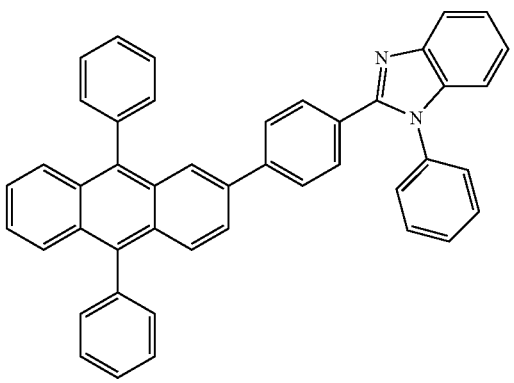
ET5
ET6
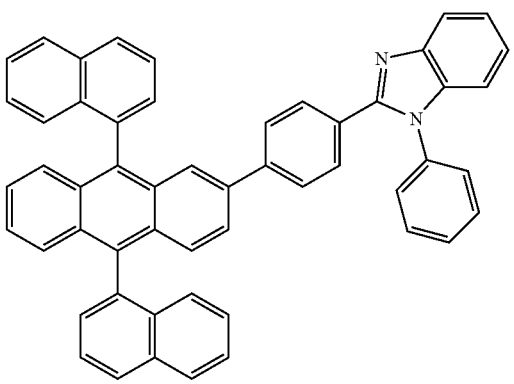

ET7
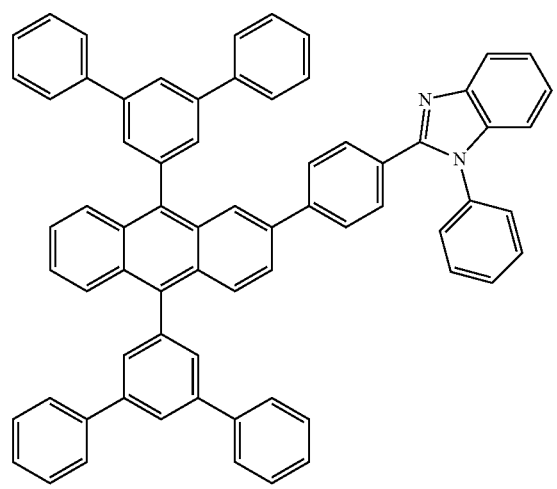
ET8
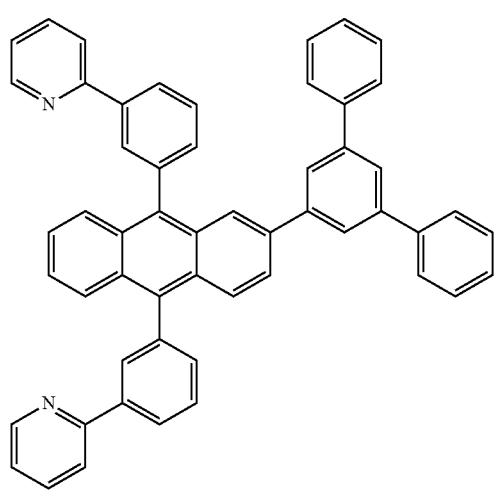
ET9
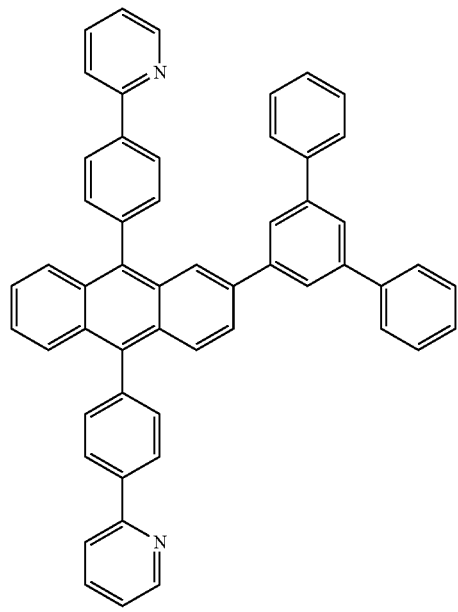
ET10
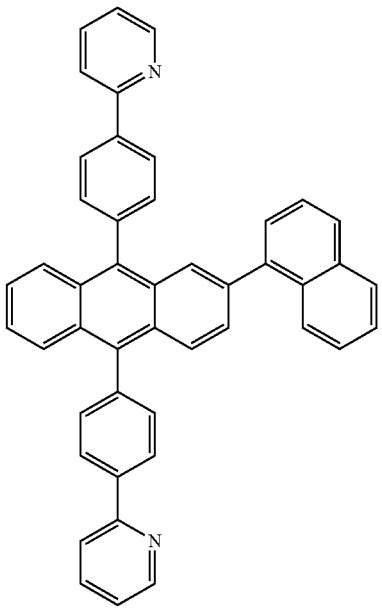
ET11
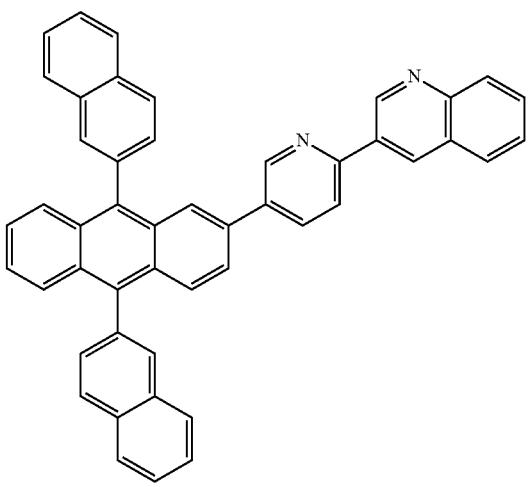
ET12
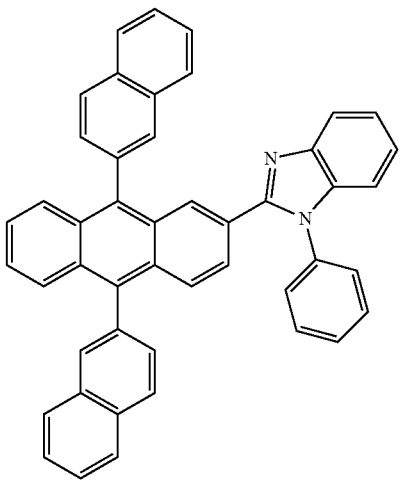

ET13
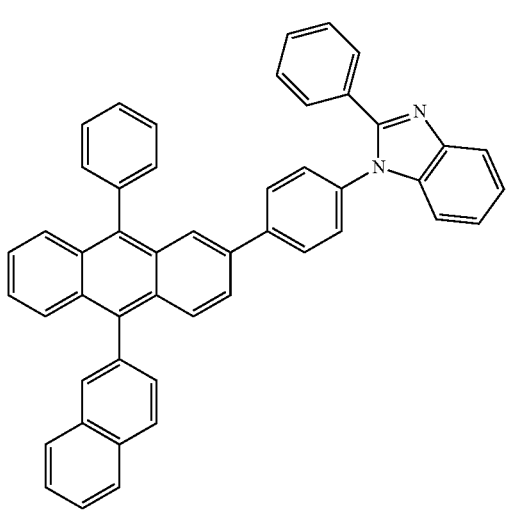
ET14
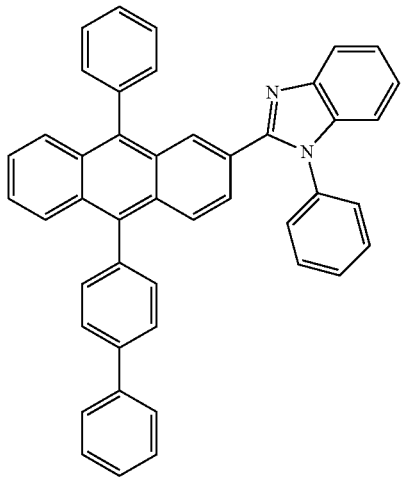
ET15
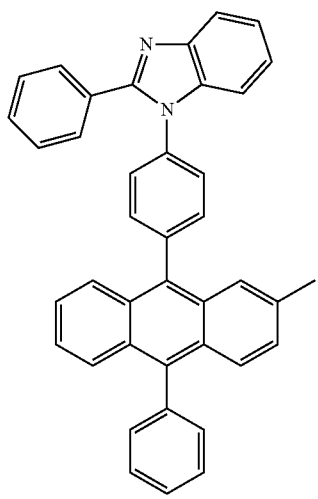
ET16
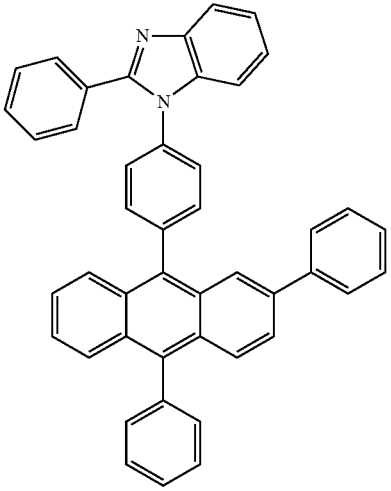
ET17
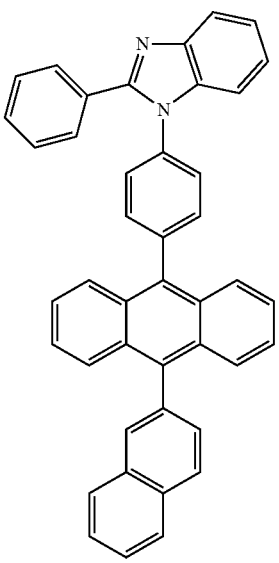
ET18
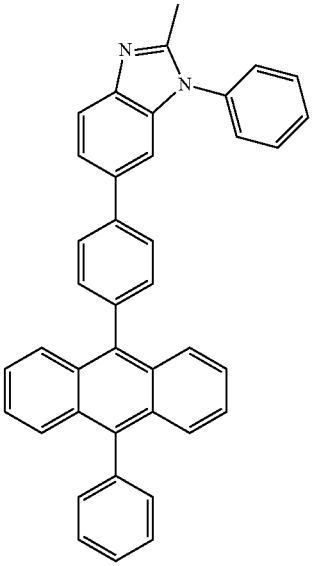

ET19
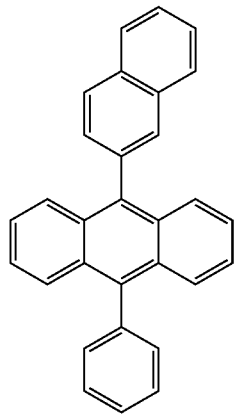
ET20
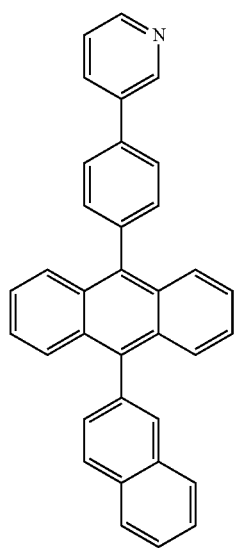
ET21
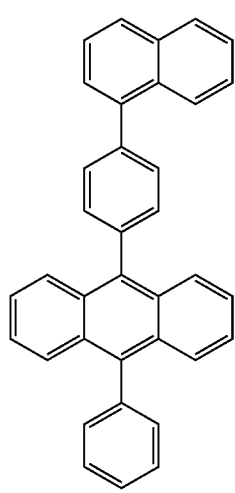
ET22
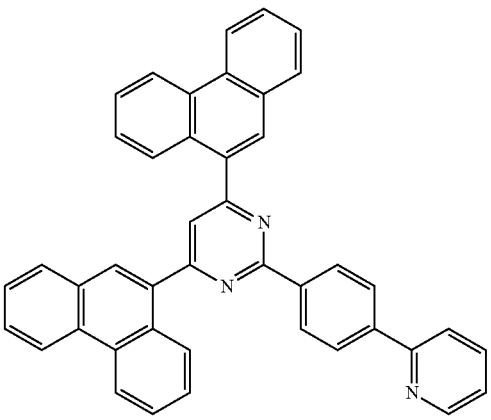
ET23
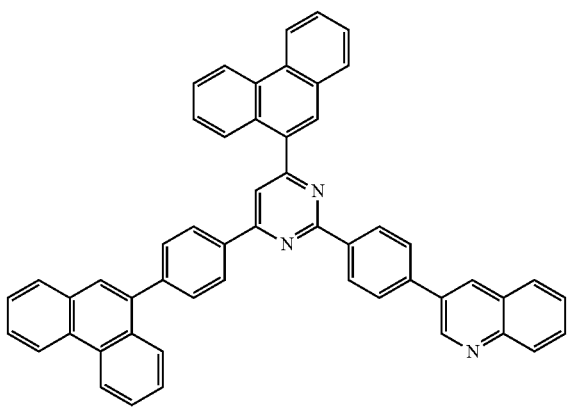
ET24
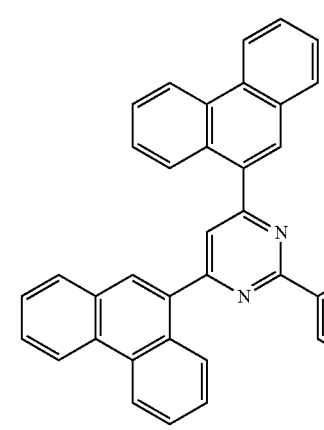

ET25
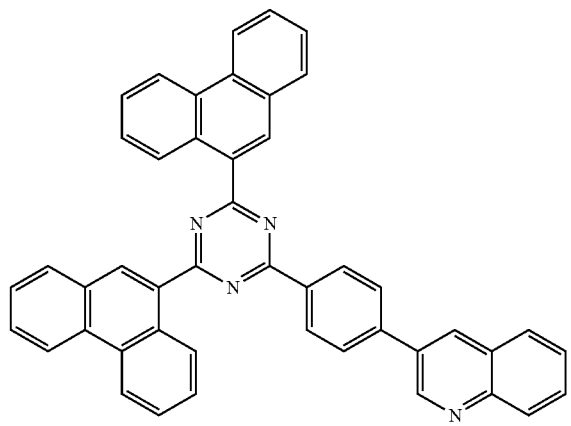
ET28
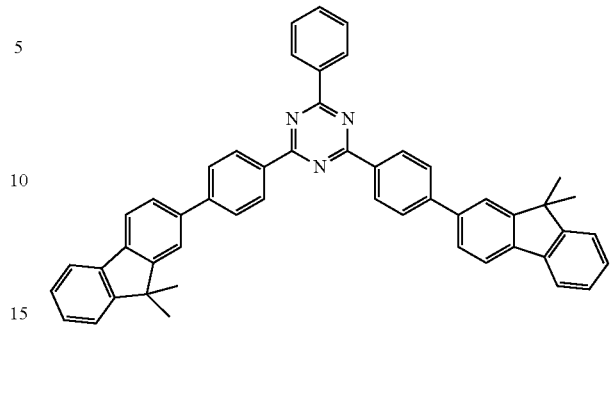
ET26
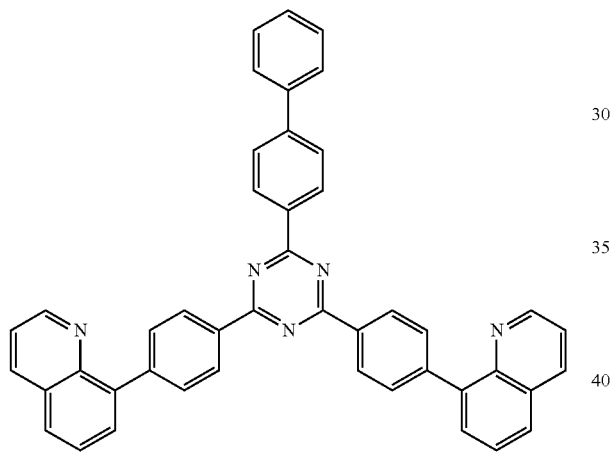
ET29
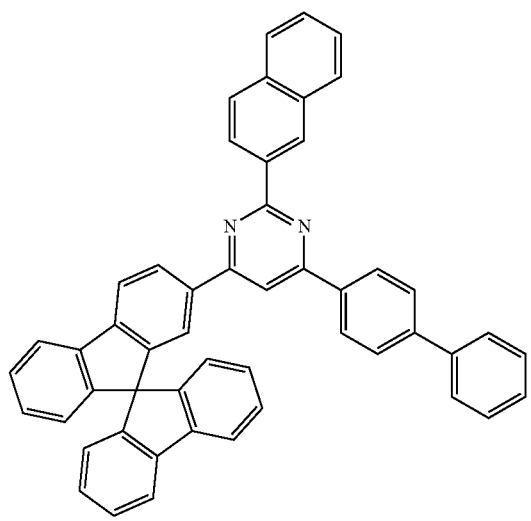
ET27
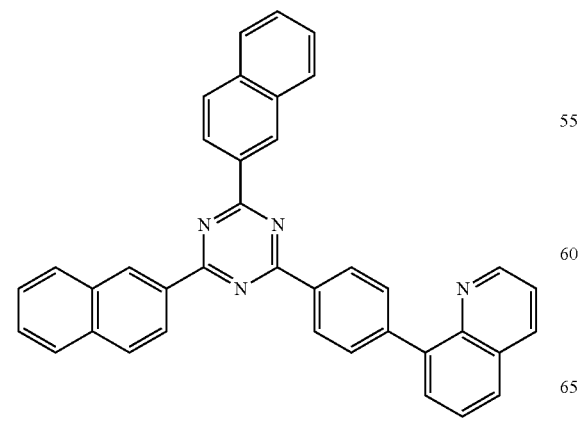
ET30
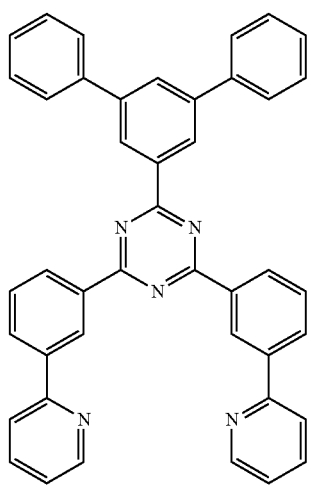

ET31
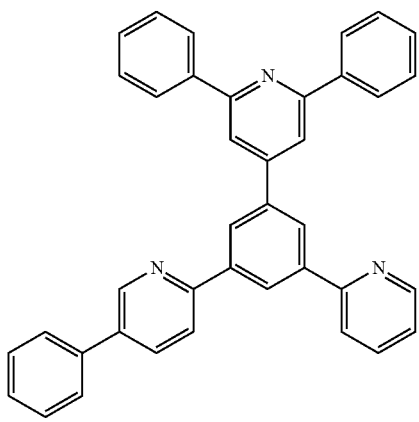
ET34
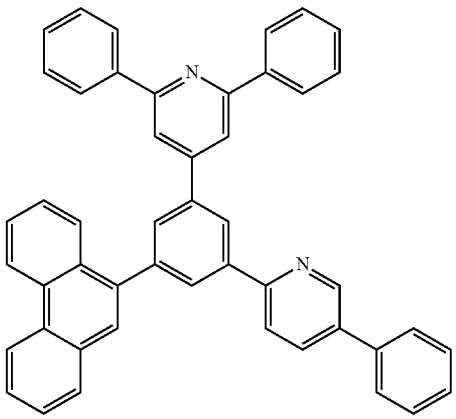
ET32
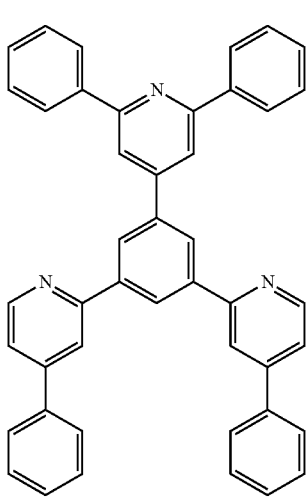
ET35
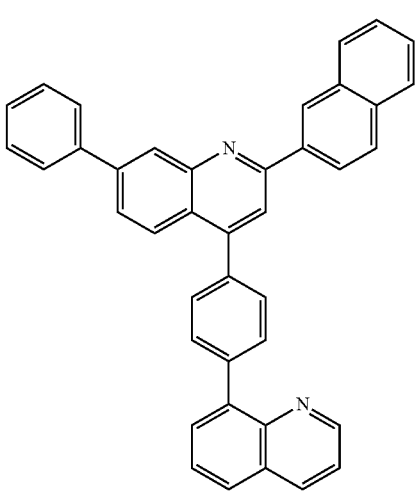
ET33
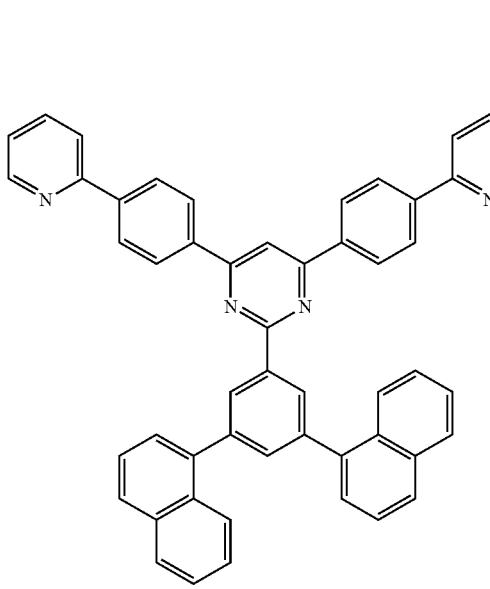
ET36
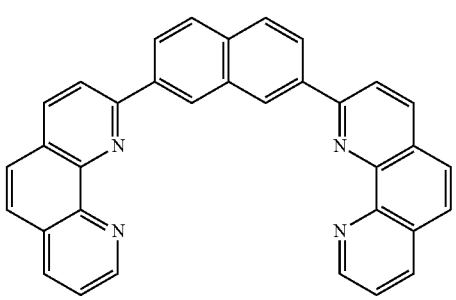
In one or more embodiments, the electron transport region may include at least one selected from 2,9-dimethyl-4,7-diphenyl-1,10-phenanthroline (BCP), 4,7-dphenyl-1,10-phenanthroline (Bphen), Alq₃, BAlq, 3-(biphenyl-4-yl)-5-(4-tert-butylphenyl)-4-phenyl-4H-1,2,4-triazole (TAZ), and NTAZ.

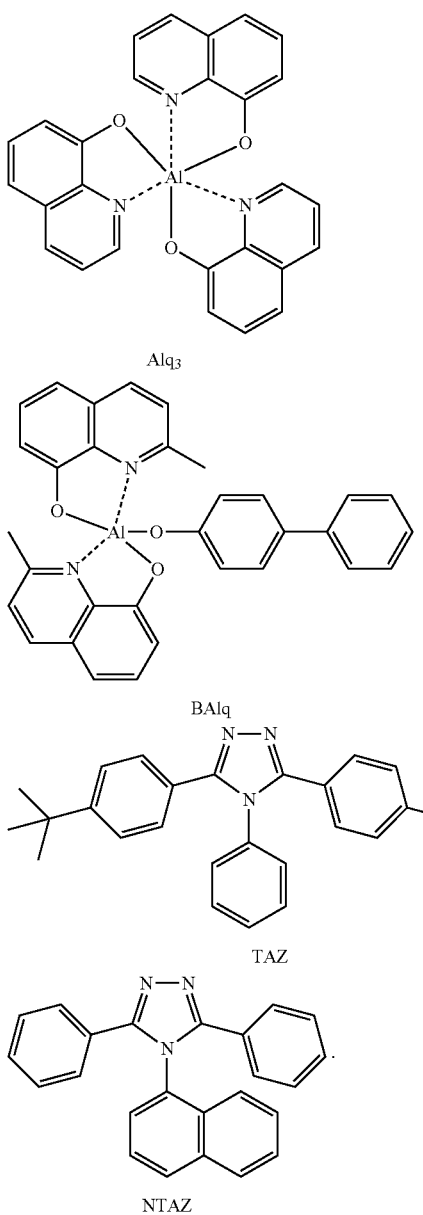

Alq₃

BAlq

TAZ

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, e.g., about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from an Li ion, a Na ion, a K ion, a Rb ion, and a Cs ion, and the alkaline earth-metal complex may include a metal ion selected from a Be ion, a Mg ion, a Ca ion, an Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene.

For example, the metal-containing material may include a Li complex. The Li complex may include, e.g., Compound ET-D1 (lithium quinolate, LiQ) or ET-D2.

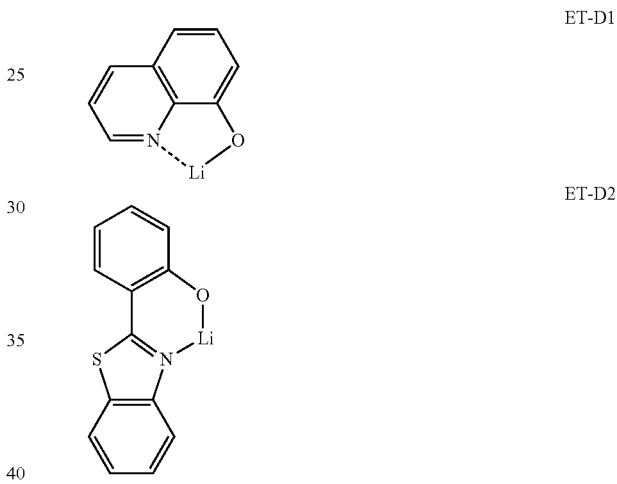

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include alkali metal, alkaline earth metal, rare-earth metal, alkali metal compound, alkaline earth-metal compound, rare-earth metal compound, alkali metal complex, alkaline earth-metal complex, rare-earth metal complex, or any combinations thereof.

The alkali metal may be selected from Li, Na, K, Rb, and a Cs. In one embodiment, the alkali metal may be Li, Na, or Cs. In one or more embodiments, the alkali metal may be Li or Cs.

The alkaline earth metal may be selected from Mg, Ca, Sr, and Ba.

The rare-earth metal may be selected from Sc, Y, Ce, Yb, Gd, and Tb.

The alkali metal compound, the alkaline earth-metal compound, and the rare-earth metal compound may be selected from oxides and halides (for example, fluorides, chlorides, bromides, or iodides) of the alkali metal, the alkaline earth-metal and rare-earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one embodiment, the alkali metal compound may be selected from LiF, $Li_2O$, NaF, LiI, NaI, CsI, and KI.

The alkaline earth-metal compound may be selected from alkaline earth-metal compounds, such as BaO, SrO, CaO, $Ba_xSr_{1-x}O$ (0<x<1), or $Ba_xCa_{1-x}O$ (0<x<1). In one embodiment, the alkaline earth-metal compound may be selected from BaO, SrO, and a CaO.

The rare-earth metal compound may be selected from $YbF_3$, $ScF_3$, $ScO_3$, $Y_2O_3$, $Ce_2O_3$, $GdF_3$, and $TbF_3$. In one embodiment, the rare-earth metal compound may be selected from $YbF_3$, $ScF_3$, $TbF_3$, $YbI_3$, $ScI_3$, and $TbI_3$.

The alkali metal complex, the alkaline earth-metal complex, and the rare-earth metal complex may include an ion of alkali metal, alkaline earth-metal, and rare-earth metal as described above, and a ligand coordinated with a metal ion of the alkali metal complex, the alkaline earth-metal complex, and the rare-earth metal complex may each independently be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene.

The electron injection layer may consist of alkali metal, alkaline earth metal, rare-earth metal, an alkali metal compound, an alkaline earth-metal compound, a rare-earth metal compound, an alkali metal complex, an alkaline earth-metal complex, a rare-earth metal complex, or any combinations thereof, as described above. In one or more embodiments, the electron injection layer may further include an organic material. When the electron injection layer further includes an organic material, alkali metal, alkaline earth metal, rare-earth metal, alkali metal compound, alkaline earth-metal compound, rare-earth metal compound, alkali metal complex, alkaline earth-metal complex, rare-earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode which is an electron injection electrode, and in this regard, a material for forming the second electrode 190 may be selected from metal, an alloy, an electrically conductive compound, and a mixture thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO. The second electrode 190 may be a transmissive electrode, a semi-transmissive electrode, or a reflective electrode.

The second electrode 190 may have a single-layered structure, or a multi-layered structure including two or more layers.

Figure 2:
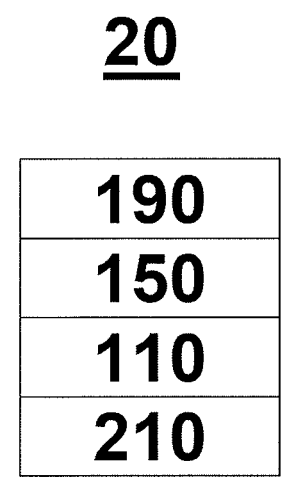
Figure 3:
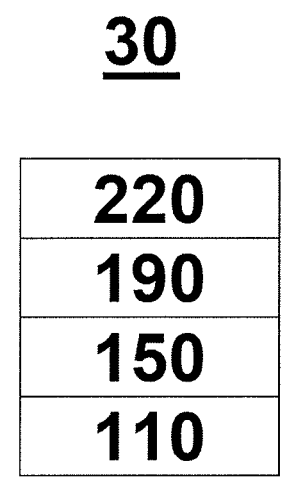
Figure 4:
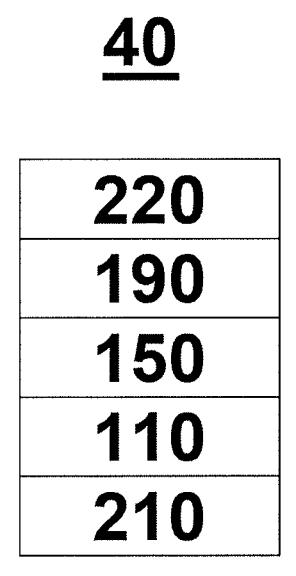

An organic light-emitting device 20 of FIG. 2 includes a first capping layer 210, a first electrode 110, an organic layer 150, and a second electrode 190 which are sequentially stacked in this stated order, an organic light-emitting device 30 of FIG. 3 includes a first electrode 110, an organic layer 150, a second electrode 190, and a second capping layer 220 which are sequentially stacked in this stated order, and an organic light-emitting device 40 of FIG. 4 includes a first capping layer 210, a first electrode 110, an organic layer 150, a second electrode 190, and a second capping layer 220.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and a Compounds CP1 to CP5.

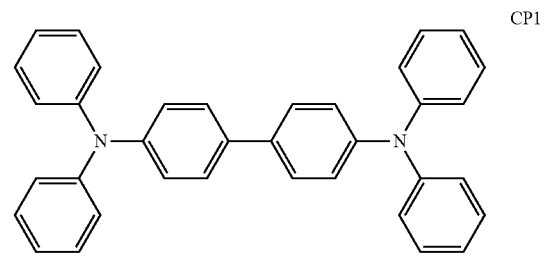

CP1

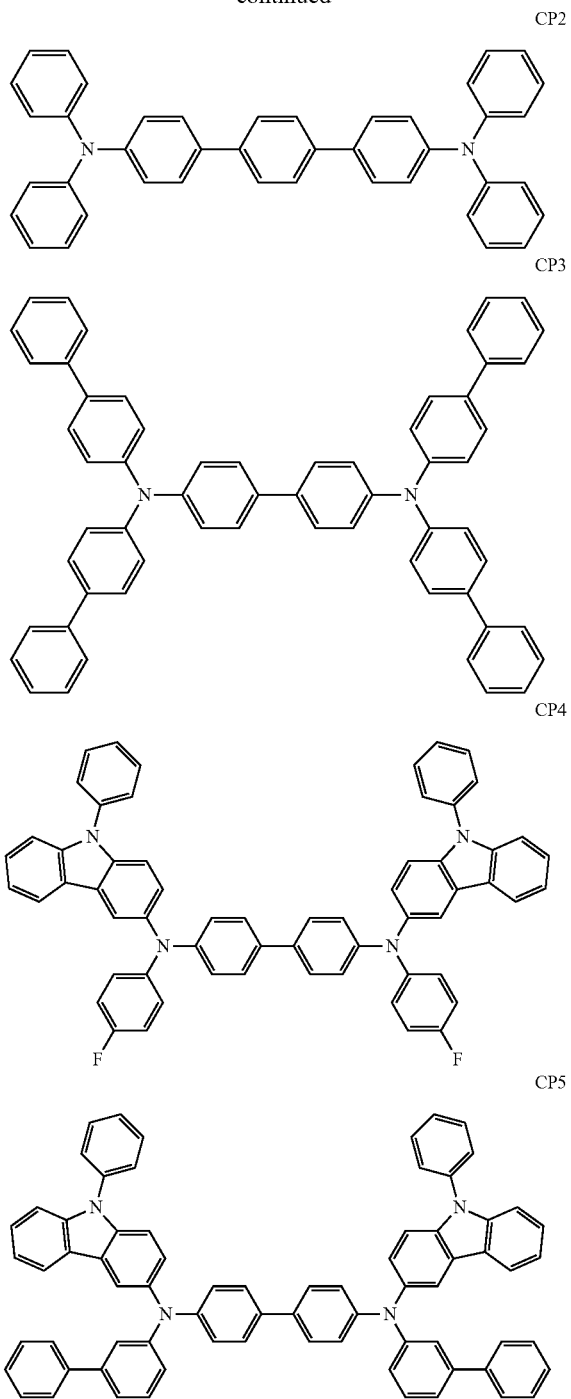

Hereinbefore, the organic light-emitting device according to an embodiment has been described in connection with FIGS. 1-4.

Layers constituting the hole transport region, an emission layer, and layers constituting the electron transport region may be formed in a certain region by using one or more suitable methods selected from vacuum deposition, spin coating, casting, langmuir-blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec by taking into account a compound to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a compound to be included in a layer to be formed, and the structure of a layer to be formed.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" used herein refers to a divalent group having the same structure as the $C_1$-$C_{60}$ alkyl group.

The term "$C_2$-$C_{60}$ alkenyl group" as used herein refers to a hydrocarbon group formed by substituting at least one carbon-carbon double bond in the middle or at the terminus of the $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by substituting at least one carbon-carbon triple bond in the middle or at the terminus of the $C_2$-$C_{60}$ alkyl group, and non-limiting examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group: The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, Si, P, and S as a ring-forming atom and 1 to 10 carbon atoms, and non-limiting examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and does not have aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group are a 4,5-dihydro-1,2,3,4-oxatriazolyl group, a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, and S as a ring-forming atom, and 1 to 60 carbon atoms. The term "$C_1$-$C_{60}$ heteroarylene group" as used herein refers to a divalent group having a heterocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) that has two or more rings condensed with each other, only carbon atoms as a ring-forming atom, and non-aromaticity in the entire molecular structure. A detailed example of the monovalent non-aromatic condensed polycyclic group is a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) that has two or more rings condensed to each other, has at least one heteroatom selected from N, O, Si, P, and S, other than carbon atoms, as a ring-forming atom, and has non-aromaticity in the entire molecular structure. An example of the monovalent non-aromatic condensed heteropolycyclic group is a carbazolyl group. The term "divalent non-aromatic condensed heteropolycyclic group," used herein, refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as a benzene group; a monovalent group, such as a phenyl group; or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one of substituents of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{oo}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_6$, $Q_{11}$ to $Q_{13}$, $Q_{21}$ to $Q_{23}$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph" used herein refers to a phenyl group, the term "Me" used herein refers to a methyl group, the term "Et" used herein refers to an ethyl group, the term "ter-Bu" or "Bu$^t$" used herein refers to a tert-butyl, and the term "OMe" used herein refers to a methoxy group.

The term "biphenyl group" as used therein refers to "a phenyl group substituted with a phenyl group." In other words, a "biphenyl group" is a substituted phenyl group having a C6-C60 aryl group as a substituent.

The term "terphenyl group" as used herein refers to "a phenyl group substituted with a biphenyl group." In other words, the "terphenyl group" is a substituted phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in detail with reference to Synthesis Examples and Examples. The wording "B was used instead of A" used in describing Synthesis Examples refers to that an identical molar equivalent of B was used in place of A.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1: Synthesis of Compound 1

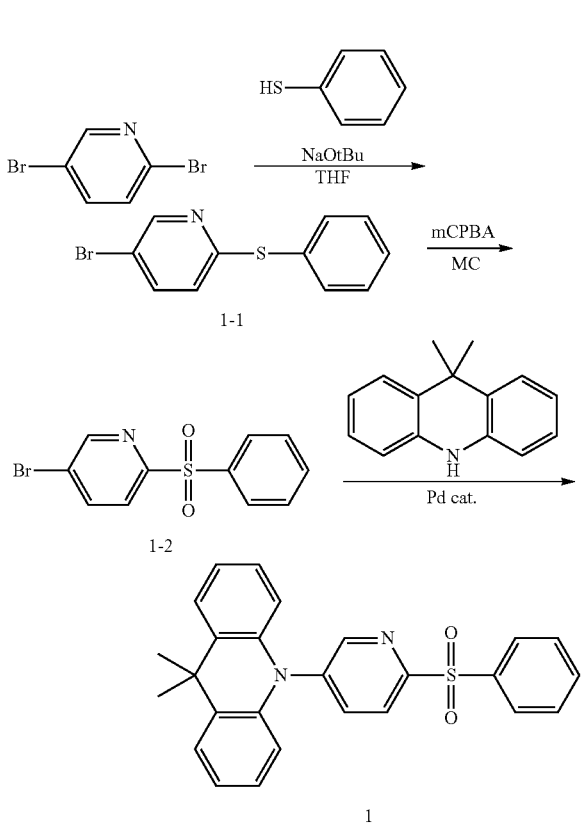

Synthesis of Intermediate 1-1

2,5-dibromopyridine and thiophenol were reacted with NaOtBu in tetrahydrofuran (THF) to obtain Intermediate 1-1. Intermediate 1-1 was confirmed by LC-MS.

$C_{11}H_8BrNS$: M+1 265.9

Synthesis of Intermediate 1-2

Intermediate 1-1 was oxidized in methylene chloride (MC) by using m-chloroperoxybenzoic acid (mCPBA) to obtain Intermediate 1-2. Intermediate 1-2 was confirmed by LC-MS.

$C_{11}H_8BrNO_2S$: M+1 297.9

Synthesis of Compound 1

3.4 g of Intermediate 1-2, 2.4 g of 9,9-dimethyl-9,10-dihydroacridine, 0.077 g of palladium (II) acetate, 0.18 g of triphenylphosphine, and 1.6 g of NaOtBu were dissolved in 60 mL of toluene, and then, the mixture was refluxed for 3 hours. The obtained reaction solution was cooled to ambient temperature, and then, an organic layer was extracted therefrom by using ethyl acetate (EA), and washed with water. Then, the collected organic layer was dried by using magnesium sulfate, and the residue obtained by evaporating a solvent therefrom was separation-purified by silica gel column chromatography, thereby completing the preparation of 3.0 g (yield: 62%) of Compound 1. Compound 1 was confirmed by LC-MS and $^1$H NMR.

$C_{26}H_{22}N_2O_2S$: M+1 427.2

$^1$H NMR (500 MHz, CDCl$_3$) δ=8.07-8.03 (m, 3H), 7.93 (t, 1H), 7.82 (s, 1H), 7.75 (t, 2H), 7.27-7.14 (m, 7H), 6.95 (t, 2H), 1.71 (s, 6H).

Synthesis Example 2: Synthesis of Compound 19

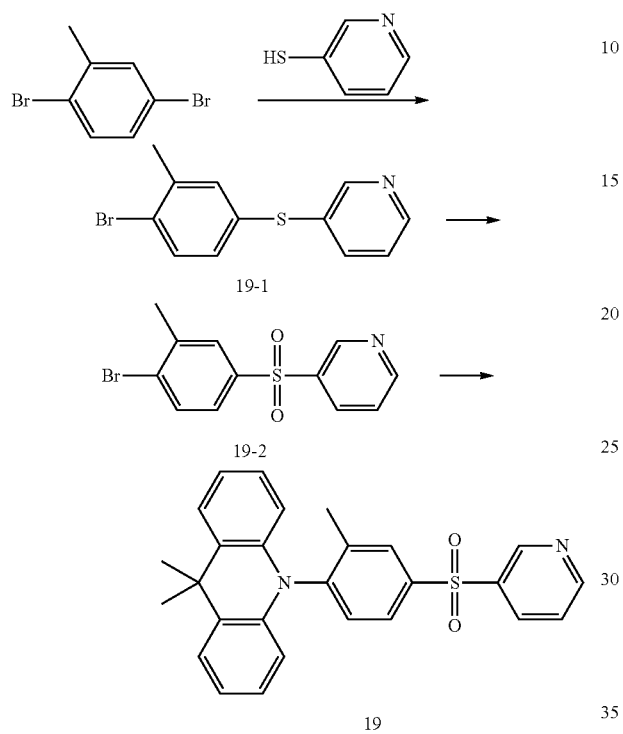

Synthesis of Intermediate 19-1

Intermediate 19-1 was prepared in the same manner as used to synthesize Intermediate 1-1, except that 3,6-dibromo-2-methylpyridine was used instead of 2,5-dibromopyridine, and pyridine-3-thiol was used instead of thiophenol. Intermediate 19-1 was confirmed by LC-MS.

C$_{12}$H$_{10}$BrNS: M+1 280.9

Synthesis of Intermediate 19-2

Intermediate 19-2 was prepared in the same manner as used to synthesize Intermediate 1-2, except that Intermediate 19-1 was used instead of Intermediate 1-1. Intermediate 19-2 was confirmed by LC-MS.

C$_{12}$H$_{10}$BrNO$_2$S: M+1 311.9

Synthesis of Compound 19

2.8 g (yield: 55%) of Compound 19 was prepared in the same manner as used to synthesize Compound 1, except that Intermediate 19-2 was used instead of Intermediate 1-2. Compound 19 was confirmed by LC-MS and $^1$H NMR.

C$_{27}$H$_{24}$N$_2$O$_2$S: M+1 441.1

$^1$H NMR (500 MHz, CDCl$_3$) δ=8.86 (s, 1H), 8.51 (d, 1H), 8.39 (d, 1H), 7.67-7.48 (m, 4H), 7.19-7.14 (m, 6H), 6.92 (t, 2H), 2.13 (s, 3H), 1.68 (s, 6H).

Synthesis Example 3: Synthesis of Compound 26

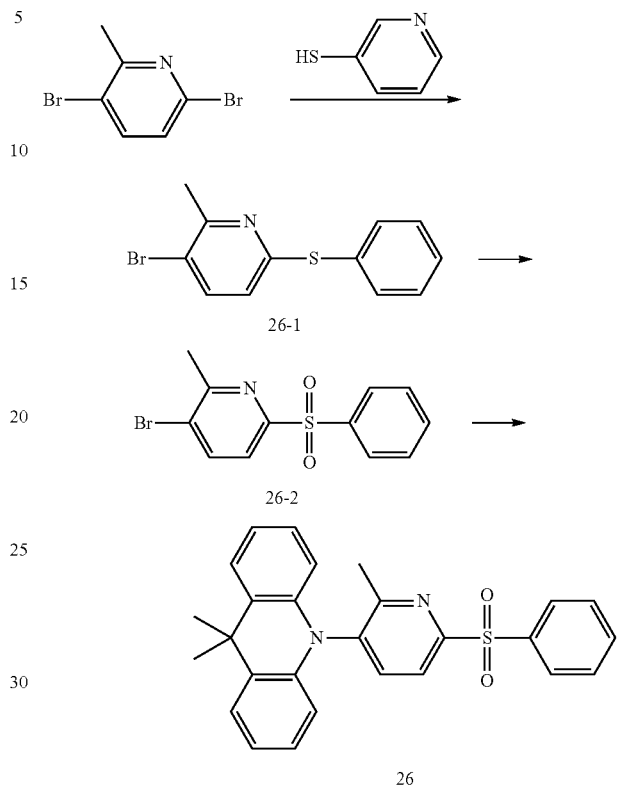

Synthesis of Intermediate 26-1

Intermediate 26-1 was prepared in the same manner as used to synthesize Intermediate 1-1, except that 3,6-dibromo-2-methylpyridine was used instead of 2,5-dibromopyridine. Intermediate 26-1 was confirmed by LC-MS.

C$_{12}$H$_{10}$BrNS: M+1 280.8

Synthesis of Intermediate 26-2

Intermediate 26-2 was prepared in the same manner as used to synthesize Intermediate 1-2, except that Intermediate 26-1 was used instead of Intermediate 1-1. Intermediate 26-2 was confirmed by LC-MS.

C$_{12}$H$_{10}$BrNO$_2$S: M+1 312.0

Synthesis of Compound 26

2.6 g (yield: 49%) of Compound 26 was prepared in the same manner as used to synthesize Compound 1, except that Intermediate 26-2 was used instead of Intermediate 1-2. Compound 26 was confirmed by LC-MS and $^1$H NMR.

C$_{27}$H$_{24}$N$_2$O$_2$S: M+1 441.2

$^1$H NMR (500 MHz, CDCl$_3$) δ=8.07 (d, 2H), 7.93 (t, 1H), 7.87 (d, 1H), 7.75 (t, 2H), 7.24 (d, 1H), 7.21-7.13 (m, 6H), 6.97 (t, 2H), 2.49 (s, 3H), 1.69 (s, 6H).

Synthesis Example 4: Synthesis of Compound 31

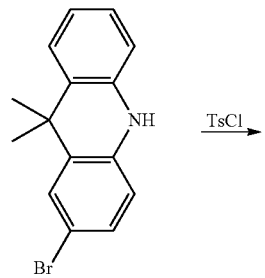

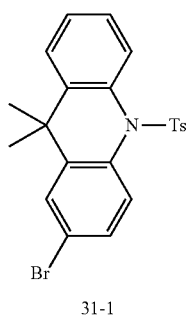
31-1

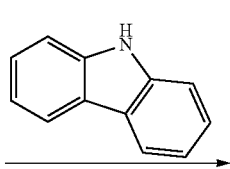

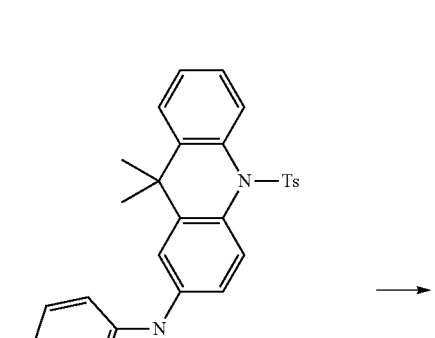
31-2

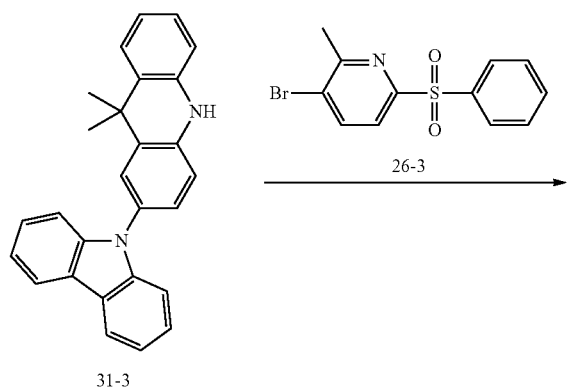
31-3

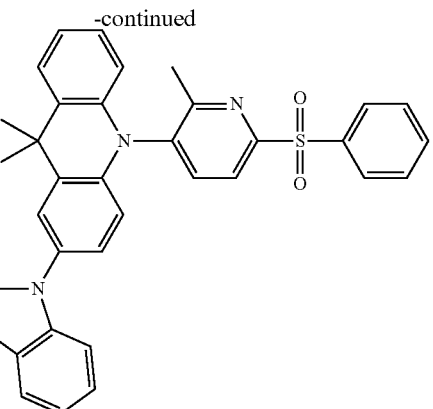
31

Synthesis of Intermediate 31-1

2-bromo-9,9-dimethyl-9,10-dihydroacridine (CAS: 1443680-94-1) was reacted with tosyl chloride (TsCl) under a basic condition to obtain Intermediate 31-1. Intermediate 31-1 was confirmed by LC-MS.

$C_{22}H_{20}BrNO_2S$ M+1: 442.1

Synthesis of Intermediate 31-2

Compound 31-1 was reacted with carbazole in the presence of a copper catalyst to obtain Intermediate 31-2. Intermediate 31-2 was confirmed by LC-MS.

$C_{34}H_{28}N_2O_2S$ M+1: 529.3

Synthesis of Intermediate 31-3

An acid was added to Compound 31-2 to obtain Intermediate 31-3. Intermediate 31-3 was confirmed by LC-MS.

$C_{27}H_{22}N_2$ M+1: 375.2

Synthesis of Compound 31

4.2 g of Compound 31-3, 3.5 g of Compound 26-3, 0.075 g of palladium (II) acetate, 0.18 g of triphenylphosphine, and 1.6 g of NaOtBu were dissolved in 60 mL of toluene, and the mixture was refluxed for 3 hours. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 5.2 g (yield: 77%) of Compound 31. Compound 31 was confirmed by LC-MS and $^1$H-NMR.

$C_{39}H_{31}N_3O_2S$ M+1: 606.1

$^1$H NMR (500 MHz, CDCl$_3$) δ=8.18 (d, 2H), 8.06 (d, 2H), 7.93 (t, 1H), 7.87 (d, 1H), 7.76-7.73 (m, 3H), 7.60-7.54 (m, 3H), 7.5 (t, 2H), 7.31 (d, 1H), 7.26 (d, 1H), 7.22-7.13 (m, 6H), 6.99 (t, 1H), 2.48 (s, 3H), 1.66 (s, 6H).

Synthesis Example 5: Synthesis of Compound 32

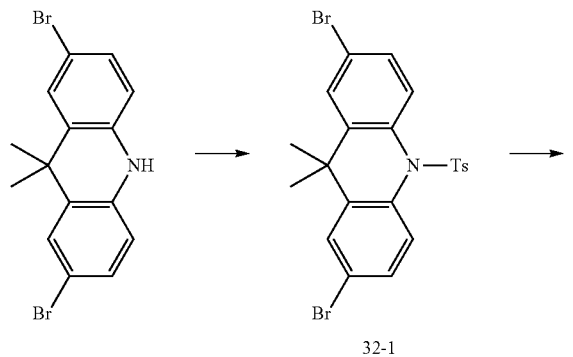

32-1

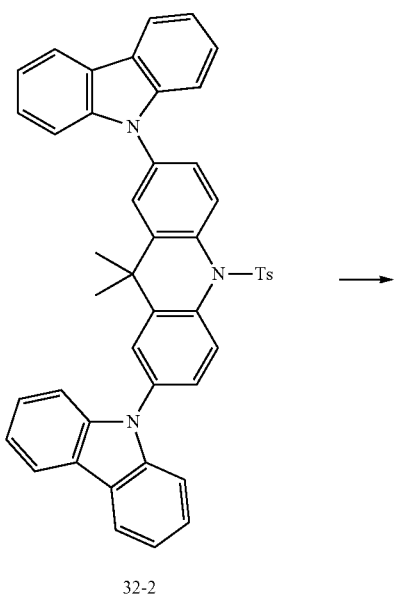

32-2

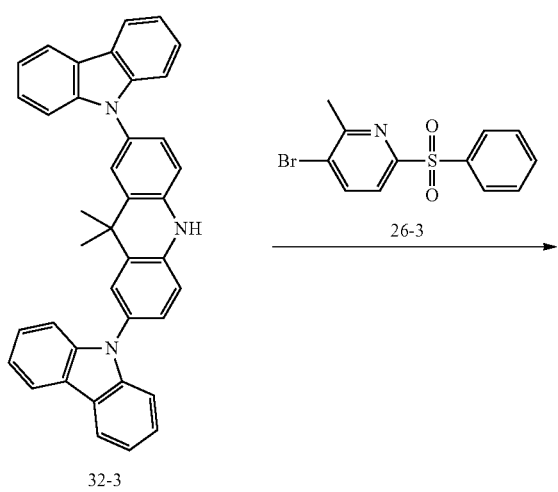

32-3

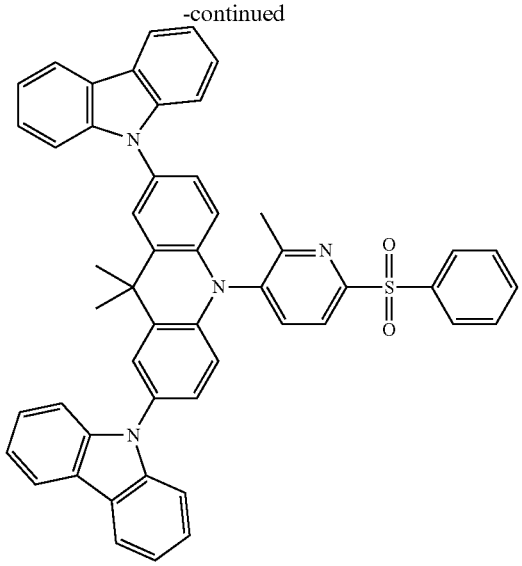

32

Synthesis of Intermediate 32-1

2,7-dibromo-9,9-dimethyl-9,10-dihydroacridine (CAS: 1333316-35-0) was reacted with TsCl under a basic condition to obtain Intermediate 32-1. Intermediate 32-1 was confirmed by LC-MS.

$C_{22}H_{19}Br_2NO_2S$ M+1: 519.8

Synthesis of Intermediate 32-2

Intermediate 32-1 was reacted with carbazole in the presence of a copper catalyst to obtain Intermediate 32-2. Intermediate 32-2 was confirmed by LC-MS.

$C_{46}H_{35}N_3O_2S$ M+1: 694.3

Synthesis of Intermediate 32-3

An acid was added to Intermediate 32-2 to obtain Intermediate 32-3.
Intermediate 32-3 was confirmed by LC-MS.
$C_{39}H_{29}N_3$ M+1: 539.1

Synthesis of Compound 32

2.9 g of Intermediate 32-3, 1.7 g of Intermediate 26-3, 0.036 g of palladium (II) acetate, 0.085 g of triphenylphosphine, and 0.78 g of NaOtBu were dissolved in 30 mL of toluene, and the mixture was refluxed for 3 hours. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 2.5 g (yield: 61%) of Compound 32. Compound 32 was confirmed by LC-MS and $^1$H-NMR.
$C_{51}H_{38}N_4O_2S$ M+1: 771.2
$^1$H NMR (500 MHz, CDCl$_3$) δ=8.21 (d, 4H), 8.04 (d, 2H), 7.94 (t, 1H), 7.88 (d, 1H), 7.76-7.73 (m, 4H), 7.59-7.54 (m, 6H), 7.51 (t, 4H), 7.32 (d, 2H), 7.27 (d, 1H), 7.22 (t, 4H), 2.48 (s, 3H), 1.71 (s, 6H).

Synthesis Example 6: Synthesis of Compound 41

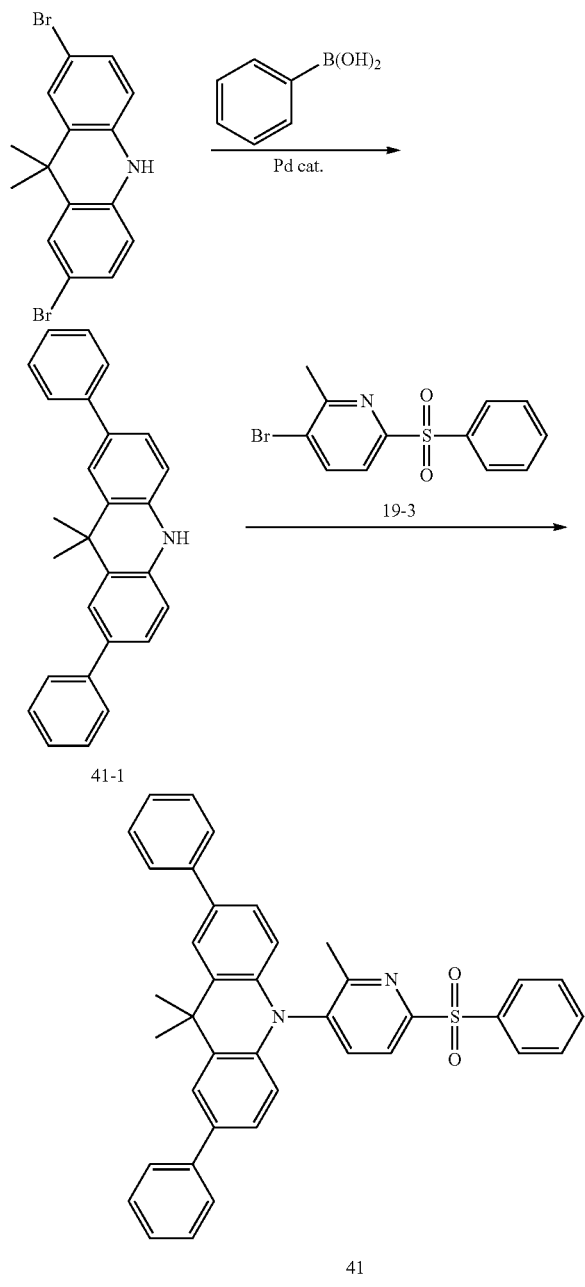

Synthesis of Intermediate 41-1

2,7-dibromo-9,9-dimethyl-9,10-dihydroacridine (CAS: 1333316-35-0) was reacted with phenylboronic acid in the presence of a palladium catalyst to obtain Intermediate 41-1. Intermediate 41-1 was confirmed by LC-MS.

$C_{27}H_{23}N$ M+1: 362.1

Synthesis of Compound 41

Intermediate 41-1 2.7 g, 2.3 g of Intermediate 26-3, 0.050 g of palladium (II) acetate, 0.12 g of triphenylphosphine, and 1.0 g of NaOtBu were dissolved in 40 mL of toluene, and then, the mixture was refluxed for 3 hours. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 3.60 g (yield: 81%) of Compound 41. Compound 41 was confirmed by LC-MS and $^1$H-NMR.

$C_{39}H_{32}N_2O_2S$ M+1: 593.3

$^1$H NMR (500 MHz, CDCl$_3$) δ=8.09 (d, 2H), 7.93 (t, 1H), 7.87 (d, 1H), 7.77-7-42 (m, 16H), 7.32 (d, 2H), 7.27 (d, 1H), 2.51 (s, 3H), 1.71 (s, 6H).

Synthesis Example 7: Synthesis of Compound 71

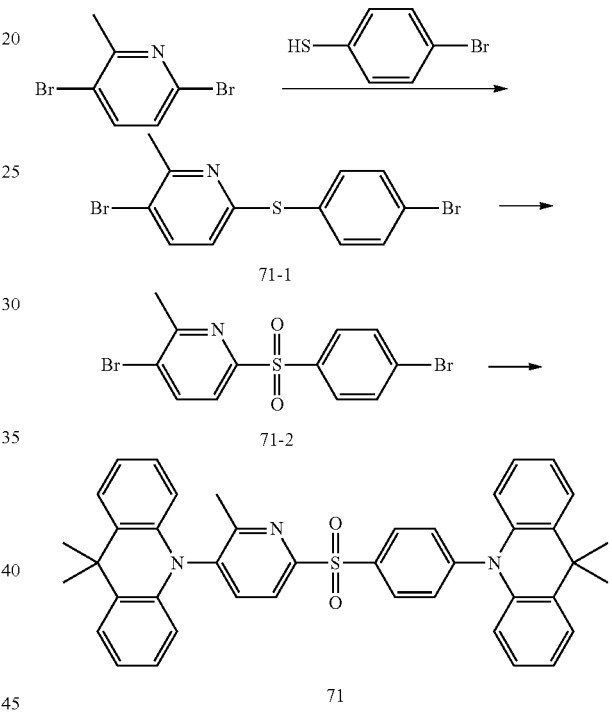

Synthesis of Intermediate 71-1

3,6-dibromo-2-methylpyridine was reacted with 4-bromothiophenol under a basic condition to obtain Intermediate 71-1. Intermediate 71-1 was confirmed by LC-MS.

$C_{12}H_9Br_2NS$, M+1: 357.9

Synthesis of Intermediate 71-2

Intermediate 71-1 was oxidized by using mCPBA to obtain Intermediate 71-2. Intermediate 71-2 was confirmed by LC-MS.

$C_{12}H_9Br_2NO_2S$, M+1: 389.7

Synthesis of Compound 71

1.7 g of Intermediate 71-2, 2.0 g of 9,9-dimethyl-9,10-dihydroacridine, 0.058 g of palladium (II) acetate, 0.14 g of triphenylphosphine, and 1.24 g of NaOtBu were dissolved in toluene, and the mixture was refluxed for 3 hours. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 1.4 g (yield: 49%) of Compound 71. Compound 71 was confirmed by LC-MS and $^1$H-NMR.

$C_{42}H_{37}N_3O_2S$, M+1: 648.2

$^1$H NMR (500 MHz, CDCl$_3$) δ=7.88-7.74 (m, 3H), 7.53 (m, 2H), 7.25 (d, 1H), 7.20-7.13 (m, 12H), 6.95 (t, 4H), 2.51 (s, 3H), 1.71 (s, 12H).

Synthesis Example 8: Synthesis of Compound 59

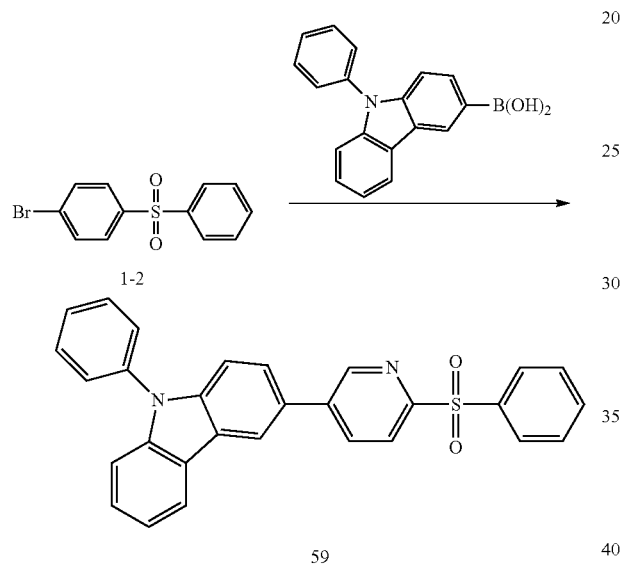

Synthesis of Compound 59

3.3 g of Intermediate 1-2, 3.8 g of (9-phenyl-9H-a carbazole-3-yl)boronic acid, 0.5 g of Pd(PPh$_3$)$_4$, and 3.8 g of potassium carbonate were loaded into a round-bottom flask, and then, 45 mL of toluene, 15 mL of ethanol, and 15 mL of distilled water were added thereto, and the resultant mixture was refluxed overnight. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 4.4 g (yield: 87%) of Compound 59. Compound 59 was confirmed by LC-MS and $^1$H-NMR.

$C_{29}H_{20}N_2O_2S$, M+1: 461.2

$^1$H NMR (500 MHz, CDCl$_3$) δ=9.1 (s, 1H), 8.31-8.03 (m, 7H), 7.93-7.87 (m, 2H), 7.75 (t, 2H), 7.62-7.51 (m, 7H), 7.24 (t, 1H).

Synthesis Example 9: Synthesis of Compound 60

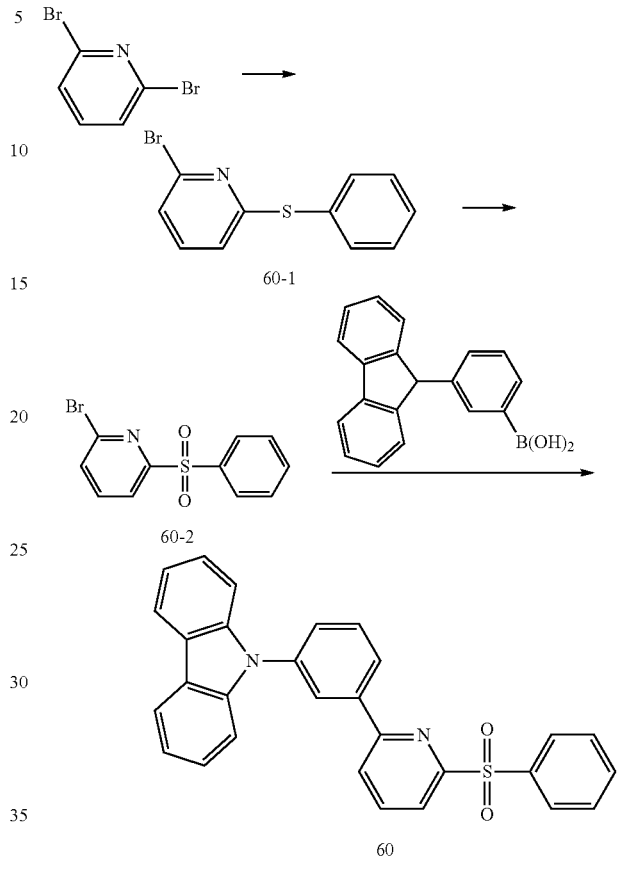

Synthesis of Intermediate 60-1

2,6-dibromipyridine was reacted with thiophenol under a basic condition to obtain Intermediate 60-1. Intermediate 60-1 was confirmed by LC-MS.

$C_{11}H_8BrNS$, M+1: 265.9

Synthesis of Intermediate 60-2

Intermediate 60-1 was oxidized by using mCPBA to obtain Intermediate 60-2.
Intermediate 60-2 was confirmed by LC-MS.
$C_{11}H_8BrNO_2S$, M+1 297.9

Synthesis of Compound 60

4.6 g of Intermediate 60-2, 5.3 g of 3-(9H-a carbazole-9-yl)boronic acid, 0.71 g of Pd(PPh$_3$)$_4$, and 5.3 g of potassium carbonate were loaded into a round-bottom flask, and then, 60 mL of toluene, 20 mL of ethanol, and 20 mL of distilled water were added thereto, and the resultant mixture was refluxed overnight. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 6.2 g (yield: 88%) of Compound 60. Compound 60 was confirmed by LC-MS and $^1$H-NMR.

$C_{29}H_{20}N_2O_2S$, M+1: 461.1

$^1$H NMR (500 MHz, CDCl$_3$) δ=8.57 (s, 1H), 8.19-8.07 (m, 5H), 7.93 (t, 1H), 7.75 (t, 2H), 7.68 (t, 1H), 7.61-7.55 (m, 5H), 7.50 (t, 2H), 7.21 (t, 2H), 7.16 (d, 1H).

Synthesis Example 10: Synthesis of Compound 61

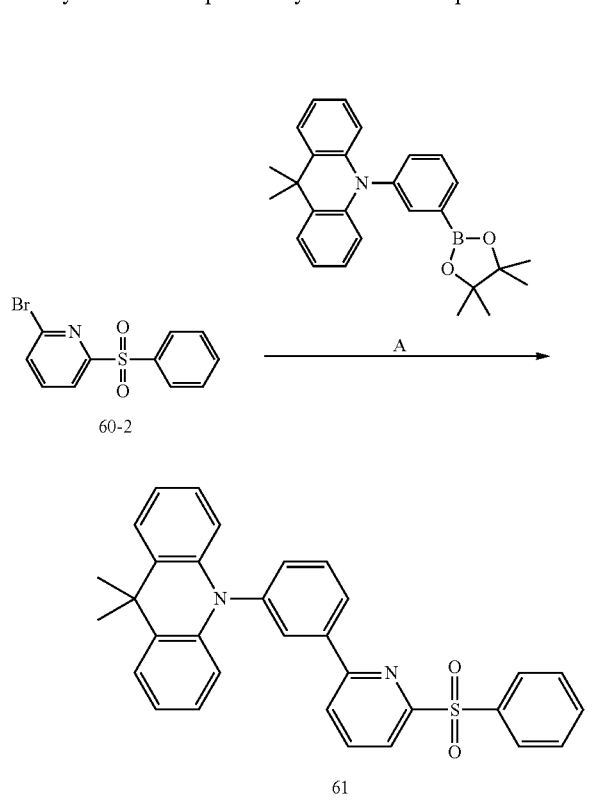

Synthesis of Compound 61

2.2 g of Intermediate 60-2, 3.6 g of Compound A (CAS No.: 1365090-67-0), 0.34 g of Pd(PPh$_3$)$_4$, and 2.5 g of potassium carbonate were loaded into a round-bottom flask round-bottom flask, and then, 30 mL of toluene, 10 mL of ethanol, and 10 mL of distilled water were added thereto, and the resultant mixture was refluxed overnight. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 2.2 g (yield: 58%) of Compound 61. Compound 61 was confirmed by LC-MS and $^1$H-NMR.

$C_{32}H_{26}N_2O_2S$, M+1: 503.2

$^1$H NMR (500 MHz, CDCl$_3$) δ=8.09 (d, 2H), 7.94-7.87 (m, 2H), 7.75 (t, 2H), 7.67 (s, 1H), 7.58 (t, 1H), 7.21-7.12 (m, 7H), 6.99 (t, 2H), 1.71 (s, 6H).

Synthesis Example 11: Synthesis of Compound 62

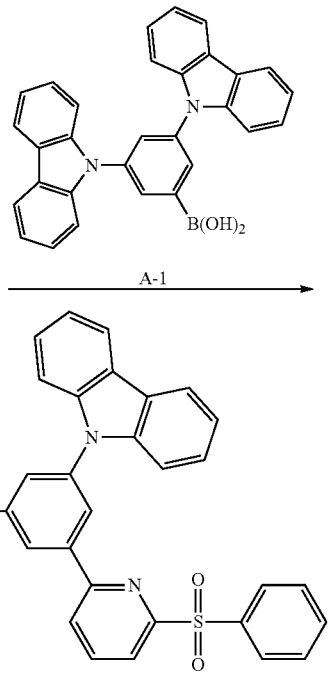

Synthesis of Compound 62

6.7 g of Intermediate 60-2, 12.2 g of Compound A-1 (CAS No.: 854952-51-5), 1.0 g of Pd(PPh$_3$)$_4$, and 7.7 g of potassium carbonate were loaded into a round-bottom flask round-bottom flask, and then, 90 mL of toluene, 30 mL of ethanol, and 30 mL of distilled water were added thereto, and the resultant mixture was refluxed overnight. The obtained reaction solution was cooled to ambient temperature, and an organic layer was extracted therefrom by using EA, and washed with water. Then, the collected organic layer was dried by using magnesium sulfate, and the residue obtained by evaporating a solvent therefrom was separation-purified by silica gel column chromatography, thereby completing the preparation of 10.4 g (yield: 74%) of Compound 62. Compound 62 was confirmed by LC-MS and $^1$H-NMR.

$C_{41}H_{27}N_3O_2S$, M+1: 626.2

$^1$H NMR (500 MHz, CDCl$_3$) δ=8.58 (s, 2H), 8.56 (d, 4H), 8.07 (d, 2H), 7.96-7.90 (m, 5H), 7.74 (t, 2H), 7.70-7.59 (m, 2H), 7.55 (t, 1H), 7.35 (t, 4H), 7.18-7.12 (m, 5H).

Example 1

As a substrate and an anode, a Corning 15 Ω/cm$^2$ (1,200 Å) ITO glass substrate was cut to a size of 50 mm×50 mm×0.7 mm, and then, sonicated by using isopropyl alcohol and pure water, each for 5 minutes, followed by exposure to ultraviolet light for 30 minutes, and then, to ozone. The resultant glass substrate was provided on a vacuum deposition device.

NPD was vacuum-deposited on the ITO anode on the substrate to form a hole injection layer having a thickness of 300 Å, and TCTA, which is a hole transport compound, was vacuum-deposited thereon to form a hole transport layer having a thickness of 200 Å.

Compound CzSi, which is a compound for forming the hole transport layer, was vacuum-deposited on the hole transport layer having a thickness of 100 Å, and then, DPEPO and Compound 1 were co-deposited thereon at a weight ratio of 90:10 to form an emission layer having a thickness of 200 Å.

Then, DPEPO was deposited on the emission layer to form an electron transport layer having a thickness of 200 Å. Then, TPBI was vacuum-deposited on the electron transport layer to form an electron injection layer having a thickness of 300 Å. Then, LiF was deposited thereon to a thickness of 10 Å, and then, Al was vacuum-deposited thereon to a thickness of 3,000 Å to form a LiF/Al cathode, thereby completing the preparation of an organic light-emitting device.

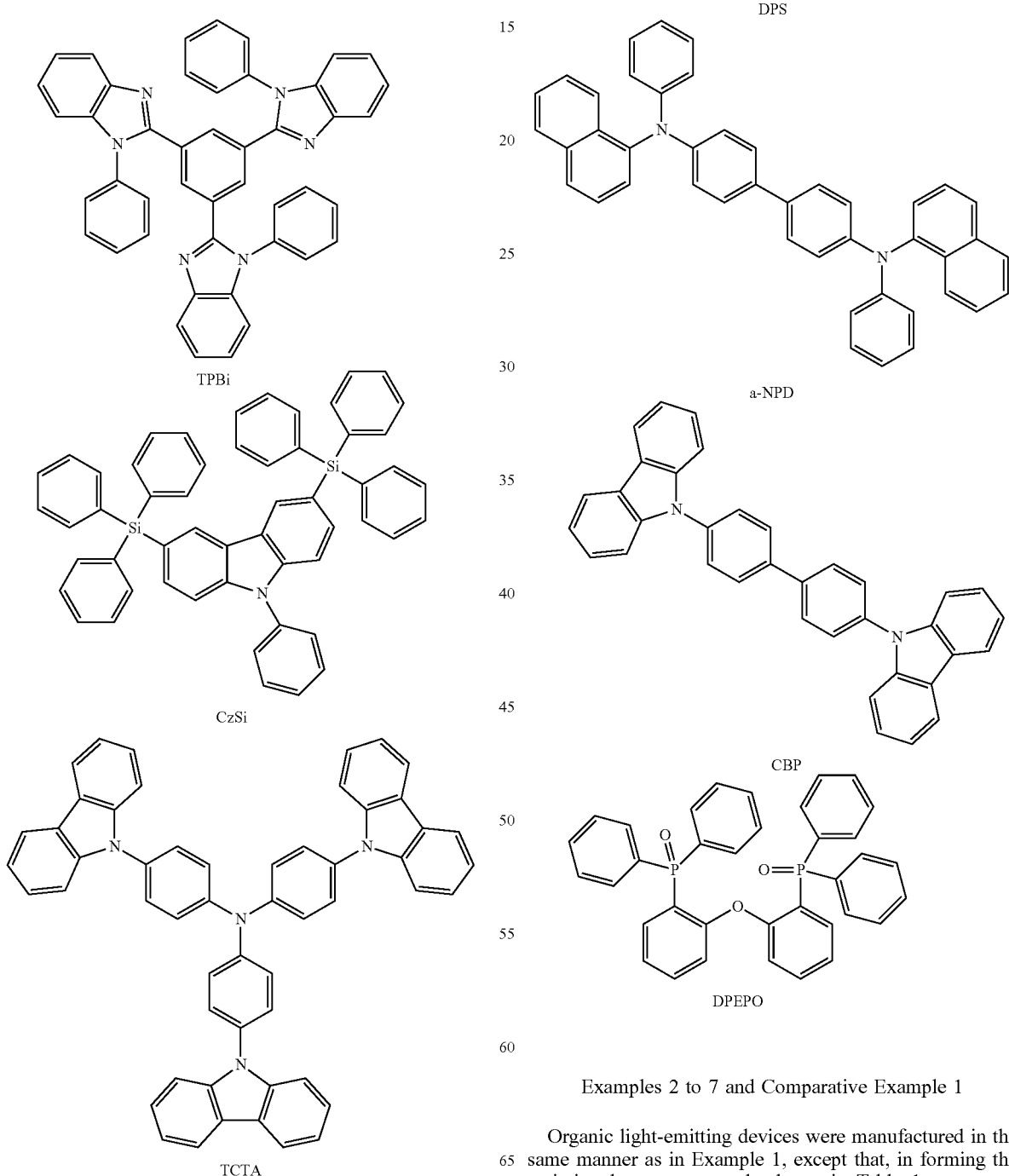

Examples 2 to 7 and Comparative Example 1

Organic light-emitting devices were manufactured in the same manner as in Example 1, except that, in forming the emission layer, compounds shown in Table 1 were used instead of Compound 1.

Example 8

As a substrate and an anode, a Corning 15 Ω/cm² (1,200 Å) ITO glass substrate was cut to a size of 50 mm×50 mm×0.7 mm, and then, sonicated by using isopropyl alcohol and pure water, each for 5 minutes, followed by exposure to ultraviolet light for 30 minutes, and then, to ozone. The resultant glass substrate was provided on a vacuum deposition device.

NPD was vacuum-deposited on the ITO anode on the substrate to form a hole injection layer having a thickness of 300 Å, and mCP, which is a hole transport compound, was vacuum-deposited thereon to form a hole transport layer having a thickness of 200 Å.

Compound 1 and Flrpic were co-deposited on the hole transport layer at a weight ratio of 90:10 to form an emission layer having a thickness of 250 Å.

Then, TAZ was deposited on the emission layer to form an electron transport layer having a thickness of 200 Å. Then, LiF was deposited on the electron transport layer to form an electron injection layer was having a thickness of 10 Å. Then, Al was vacuum-deposited on the electron injection layer to form a cathode having a thickness of 100 Å, thereby completing the preparation of an organic light-emitting device.

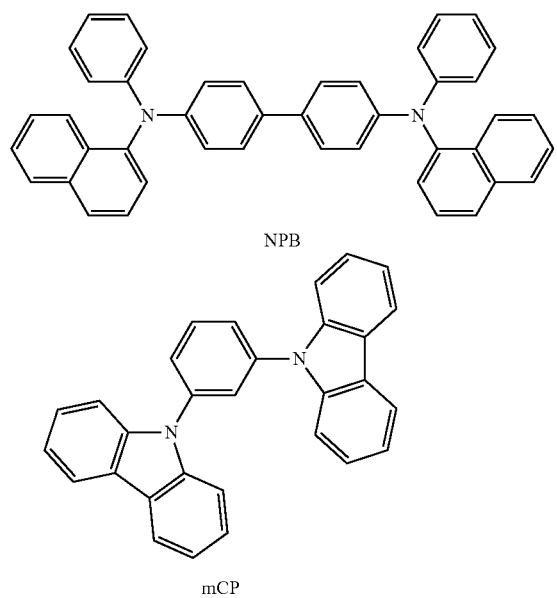

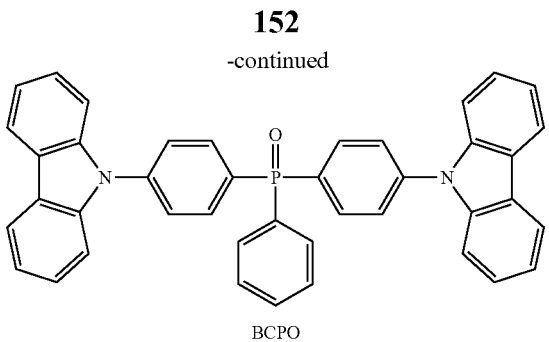

BCPO

Flrpic

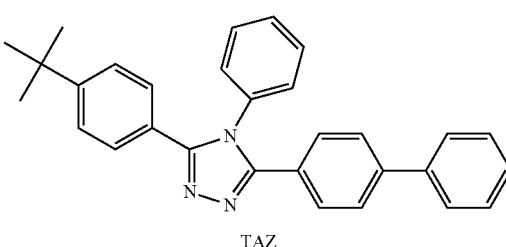

TAZ

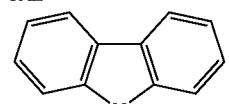

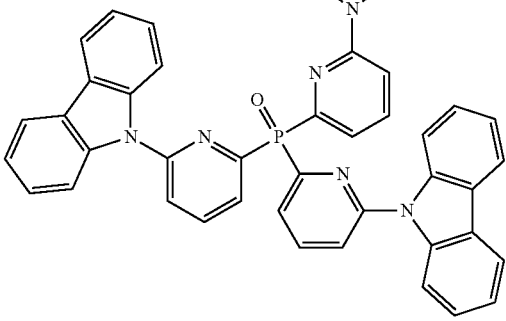

PPC

Example 9 to 14 and a Comparative Example 2

Organic light-emitting devices were manufactured in the same manner as in Example 8, except that, in forming the emission layer, compounds shown in Table 2 were used instead of Compound 1.

Evaluation Examples 1 and 2

The driving voltage, current density, efficiency, and emission color of the organic light-emitting devices of Examples 1 to 7, Comparative Example 1, and a Comparative Example 2 were measured. Results thereof are shown in Table 1.

TABLE 1

| TADF | Luminescent material | Driving voltage (V) | Current density (mA/cm²) | Efficiency (cd/A) | maximum quantum efficiency(%) | Emission color |
|---|---|---|---|---|---|---|
| Example 1 | Compound 1 | 6.0 | 2.65 | 13.9 | 22 | Blue |
| Example 2 | Compound 19 | 5.3 | 2.65 | 14.7 | 19.5 | Blue |
| Example 3 | Compound 26 | 6.2 | 2.65 | 15.9 | 24.5 | Blue |
| Example 4 | Compound 31 | 5.7 | 2.65 | 14.9 | 24 | Blue |
| Example 5 | Compound 32 | 6.2 | 2.65 | 17.1 | 22 | Blue |
| Example 6 | Compound 41 | 5.6 | 2.65 | 18.2 | 21.8 | Blue |
| Example 7 | Compound 71 | 5.2 | 2.65 | 15.8 | 19.1 | Blue |
| Comparative Example 1 | DPS | 6.5 | 2.65 | 12.3 | 17.3 | Blue |

Referring to Table 1, it may be seen that the organic light-emitting devices of Examples 1 to 7 had lower driving voltage and higher efficiency than the organic light-emitting device of Comparative Example 1.

The driving voltage, current density, efficiency, and emission color of the organic light-emitting devices of Examples 8 to 14 and a Comparative Example 2 were measured. Results thereof are shown in Table 2.

TABLE 2

| Host | Luminescent material | Driving voltage (V) | Current density (mA/cm$^2$) | Efficiency (cd/A) | Maximum quantum efficiency (%) | Emission color |
|---|---|---|---|---|---|---|
| Example 8 | 1 | 5.1 | 2.65 | 17.4 | 23.1 | Blue |
| Example 9 | 26 | 5.2 | 2.65 | 15.5 | 21.4 | Blue |
| Example 10 | 41 | 4.5 | 2.65 | 13.9 | 22.9 | Blue |
| Example 11 | 59 | 4.8 | 2.65 | 18.1 | 20.5 | Blue |
| Example 12 | 60 | 5.3 | 2.65 | 16.7 | 22.1 | Blue |
| Example 13 | 61 | 5.1 | 2.65 | 14.2 | 21.2 | Blue |
| Example 14 | 62 | 4.9 | 2.65 | 13.3 | 19.1 | Blue |
| Comparative Example 2 | PPC | 5.8 | 2.65 | 11.2 | 16.1 | Blue |

Referring to Table 2, it may be seen that the organic light-emitting devices of Examples 8 to 14 had lower driving voltage and higher efficiency than the organic light-emitting device of Comparative Example 2.

An organic light-emitting device including a heterocyclic compound according to an embodiment may have a low driving voltage, high efficiency, and a long lifespan.

The embodiments may provide an organic light-emitting device having a low driving voltage, high efficiency, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1:

$$A_1\text{-}(A_2)_{n2}, \qquad \text{<Formula 1>}$$

wherein, in Formula 1, $A_1$ is a group represented by one of Formulae 2A and 2B,

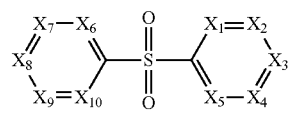

Formula 2A

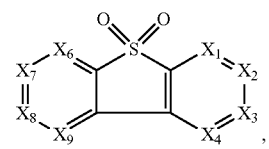

Formula 2B $A_2$ is a group represented by Formula 3, $$*\text{---}(L)_a\text{---}(Ar)_b \qquad \text{Formula 3}$$

n2 is an integer from 1 to 7, and, when n2 is two or more, groups represented by Formula 3 are identical to or different from each other, in Formulae 2A and 2B, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_9$ is N or $C(R_9)$, and $X_{10}$ is N or $C(R_{10})$, at least one of $X_1$ to $X_{10}$ in Formulae 2A and 2B is N, $R_1$ to $R_{10}$ are each independently selected from:

a binding site to A2 in Formula 1, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —C(=O)($Q_1$), and —P(=O)($Q_1$)($Q_2$), $R_1$ to $R_{10}$ are separate or are linked to form a substituted or unsubstituted condensed ring, L in Formula 3 is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, wherein L is not an anthracenylene group or a carbazolylene group, a is an integer from 0 to 3, and, when a is two or more, L(s) are identical to or different from each other,
Ar in Formula 3 is:
a group represented by one of Formulae 5-1 to 5-8; or
a group represented by one of Formulae 6-7 to 6-30, 6-32 to 6-34, 6-36 to 6-46, and 6-48 to 6-55:
Formula 5-1
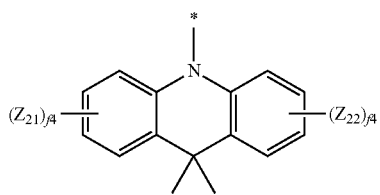
Formula 5-2
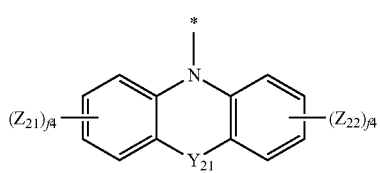
Formula 5-3
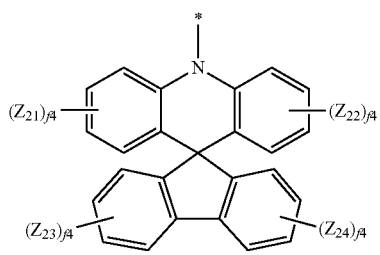
Formula 5-4
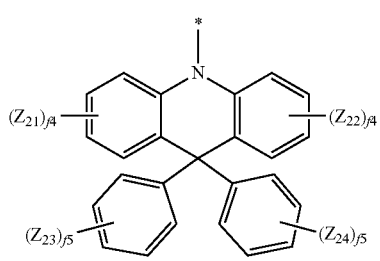
Formula 5-5
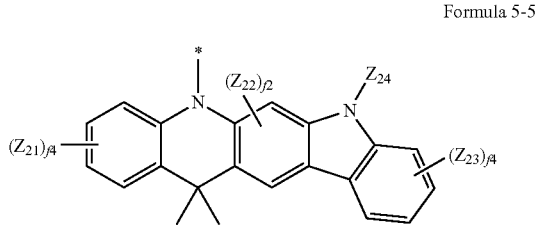
Formula 5-6
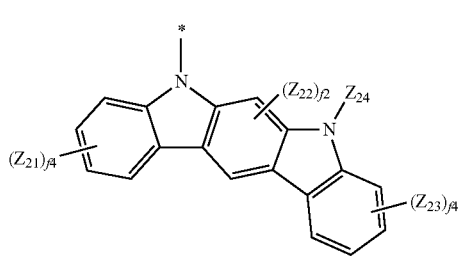
-continued
Formula 5-7
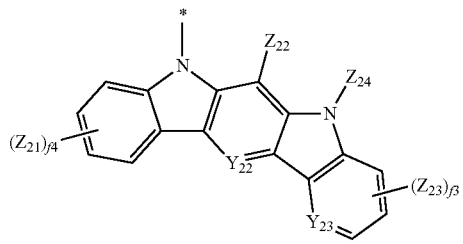
Formula 5-8
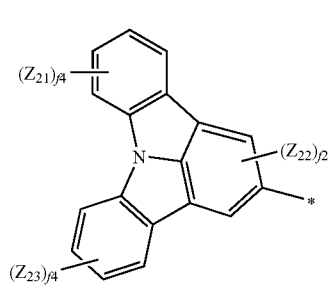
Formula 6-7
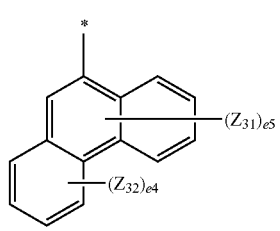
Formula 6-8
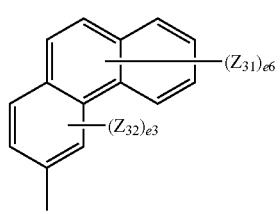
Formula 6-9
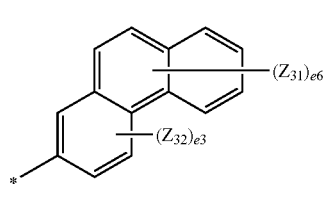
Formula 6-10
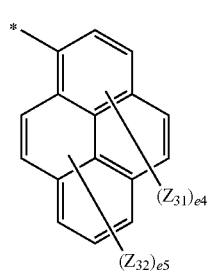

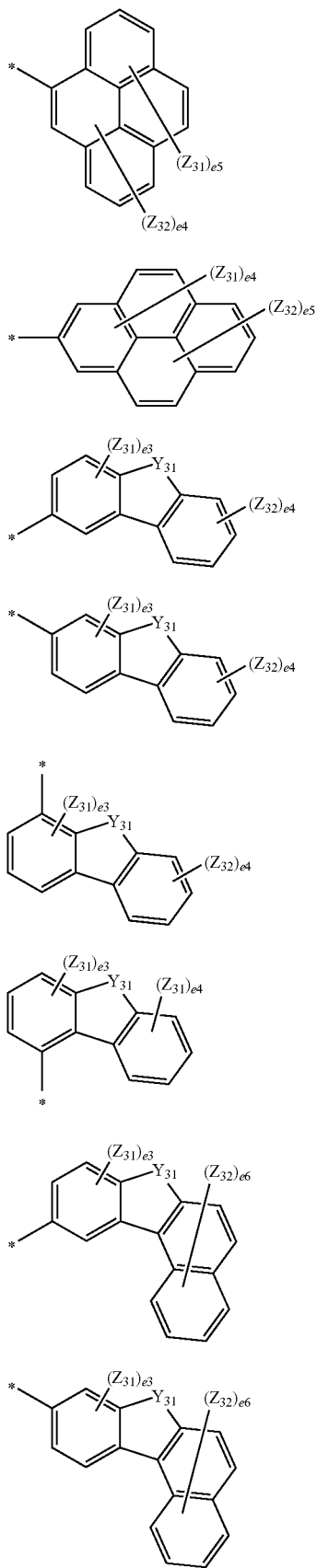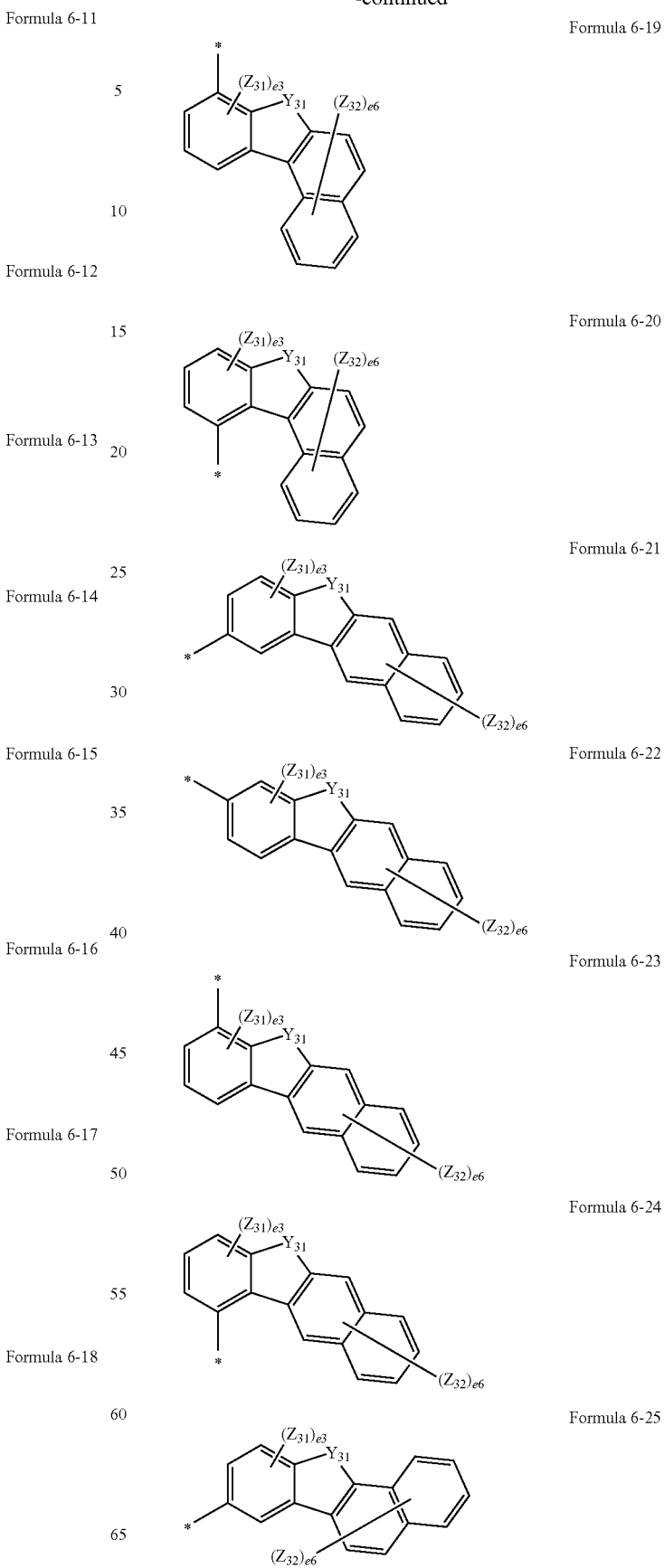

Formula 6-26
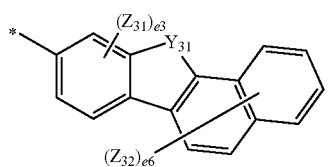
Formula 6-27
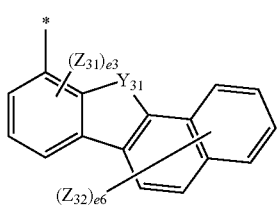
Formula 6-28
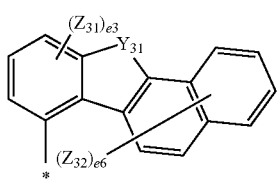
Formula 6-29
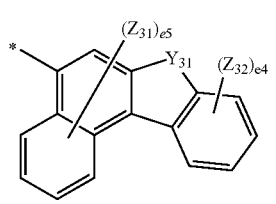
Formula 6-30
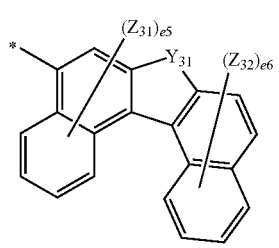
Formula 6-32
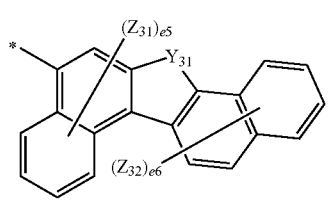
Formula 6-33
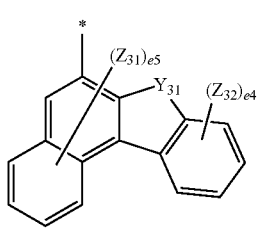
Formula 6-34
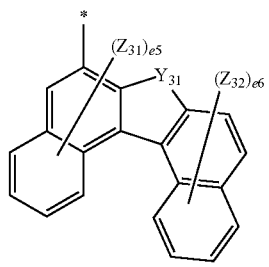
Formula 6-36
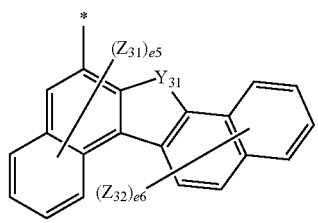
Formula 6-37
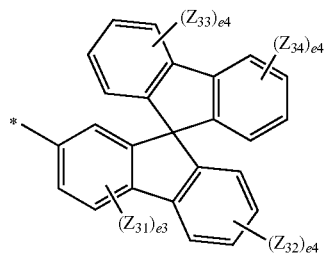
Formula 6-38
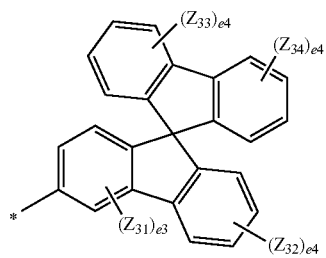
Formula 6-39
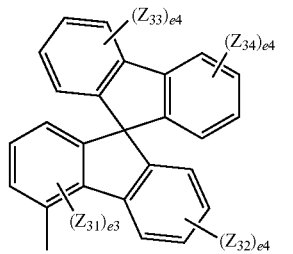
Formula 6-40
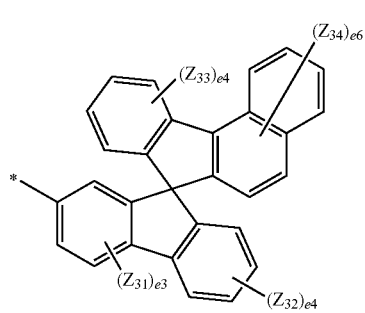

-continued
Formula 6-41
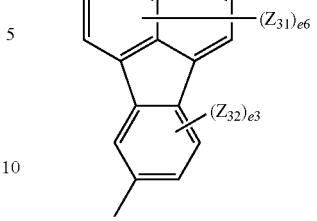
Formula 6-42
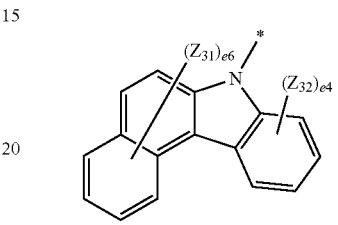
Formula 6-43
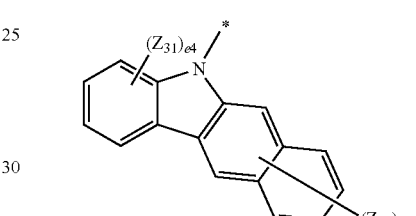
Formula 6-44
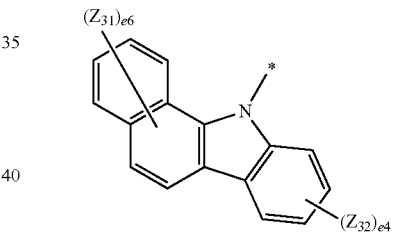
Formula 6-45
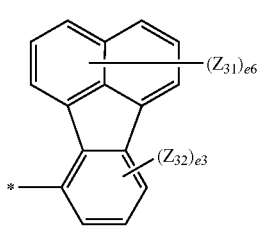
Formula 6-46
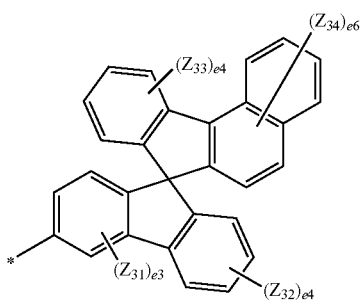
Formula 6-48
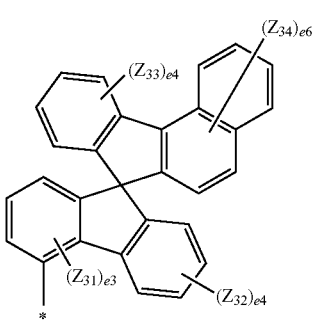
Formula 6-49
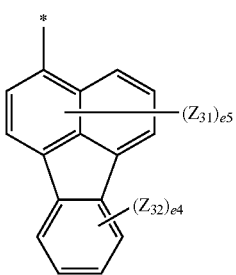
Formula 6-50
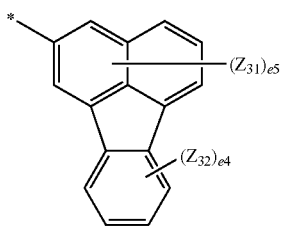
Formula 6-51
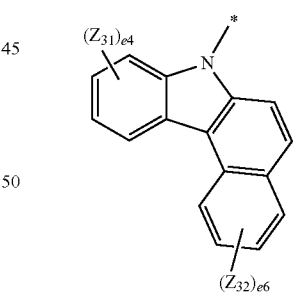
Formula 6-52
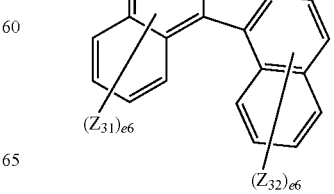

-continued

Formula 6-53

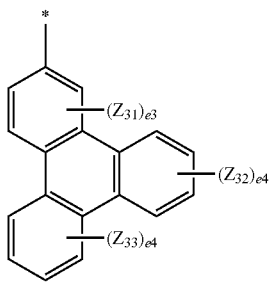

Formula 6-54

Formula 6-55

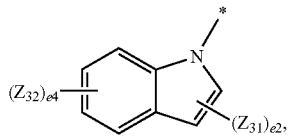

wherein, in Formulae 5-1 to 5-8, $Y_{21}$ is O or S, at least one selected from $Y_{22}$ and $Y_{23}$ is CH or N, $Z_{21}$ to $Z_{24}$ are each independently selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, benzoacridinyl group, a benzophenanthrenyl group, a dibenzophenanthrenyl group, a benzophenanthridinyl group, a dibenzophenanthridinyl group, an indenophenanthrenyl group, an indolophenanthrenyl group, a benzofuranophenanthrenyl group, a benzothiophenanthrenyl group, a benzosilolphenanthrenyl group, an indenophenanthridinyl group, an indolophenanthridinyl group, benzofuranophenanthridinyl group, a benzothiophenanthridinyl group, a benzosilolphenanthridinyl group, a dinaphthopyrrolyl group, a benzoanthracenyl group, and —$Si(Q_{31})(Q_{32})(Q_{33})$, wherein $Q_{31}$ to $Q_{33}$ are each independently selected from a $C_1$-$C_{10}$ alkyl group, a $C_1$-$C_{10}$ alkoxy group, a phenyl group, and a naphthyl group, f2 is an integer from 0 to 2,
f3 is an integer from 0 to 3,
f4 is an integer from 0 to 4,
f5 is an integer from 0 to 5, and
wherein, in Formulae 6-7 to 6-30, 6-32 to 6-34, 6-36 to 6-46, and 6-48 to 6-55, $Y_{31}$ is O, S, $C(Z_{35})(Z_{36})$, $N(Z_{37})$, or $Si(Z_{38})(Z_{39})$, $Z_{31}$ to $Z_{36}$, $Z_{38}$ and $Z_{39}$ are each independently selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, benzoacridinyl group, a benzophenanthrenyl group, a dibenzophenanthrenyl group, a benzophenanthridinyl group, a dibenzophenanthridinyl group, an indenophenanthrenyl group, an indolophenanthrenyl group, a benzofuranophenanthrenyl group, a benzothiophenanthrenyl group, a benzosilolphenanthrenyl group, an indenophenanthridinyl group, an indolophenanthridinyl group, benzofuranophenanthridinyl group, a benzothiophenanthridinyl group, a benzosilolphenanthridinyl group, a dinaphthopyrrolyl group, a benzoanthracenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group, $Z_{37}$ is selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a spiro-benzofluorene-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, an isobenzothiazolyl group, a benzoxazolyl group, an isobenzoxazolyl group, a triazolyl group, a tetrazolyl group, an oxadiazolyl group, a triazinyl group, a dibenzosilolyl group, a benzocarbazolyl group, a naphthobenzofuranyl group, a naphthobenzothiophenyl group, a naphthobenzosilolyl group, a dibenzocarbazolyl group, dinaphthothiophenyl group, a dinaphthosilolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, benzoacridinyl group, a benzophenanthrenyl group, a dibenzophenanthrenyl group, a benzophenanthridinyl group, a dibenzophenanthridinyl group, an indenophenanthrenyl group, an indolophenanthrenyl group, a benzofuranophenanthrenyl group, a benzothiophenanthrenyl group, a benzosilolphenanthrenyl group, an indenophenanthridinyl group, an indolophenanthridinyl group, benzofuranophenanthridinyl group, a benzothiophenanthridinyl group, a benzosilolphenanthridinyl group, a dinaphthopyrrolyl group, a benzoanthracenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group, e2 is an integer from 0 to 2,
e3 is an integer from 0 to 3,
e4 is an integer from 0 to 4,
e5 is an integer from 0 to 5,
e6 is an integer from 0 to 6,
e9 is an integer of 0 to 9,
b is an integer from 1 to 4, and, when b is two or more, Ar(s) are identical to or different from each other,
* indicates a binding site to a neighboring atom,
at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$ and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

2. The heterocyclic compound as claimed in claim 1, wherein:

in Formula 2A, $X_1$ is N, $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is C($R_8$), $X_9$ is C($R_9$), and $X_{10}$ is C($R_{10}$), and at least one selected from $R_2$ to $R_{10}$ is a binding site to A2 in Formula 1; and in Formula 2B, $X_1$ is N, $X_2$ is C($R_2$), $X_3$ is C($R_3$), $X_4$ is C($R_4$), $X_6$ is C($R_6$), $X_7$ is C($R_7$), $X_8$ is C($R_8$), and $X_9$ is C($R_9$), and at least one selected from $R_2$ to $R_4$ and $R_6$ to $R_9$ is a binding site to A2 in Formula 1.

3. The heterocyclic compound as claimed in claim 1, wherein:

in Formula 2A, $X_2$ is N, $X_1$ is C($R_1$), $X_3$ is C($R_3$), $X_4$ is C($R_4$), $X_5$ is C($R_5$), $X_6$ is C($R_6$), $X_7$ is C($R_7$), $X_8$ is C($R_8$), $X_9$ is C($R_9$), and $X_{10}$ is C($R_9$), and at least one selected from $R_1$ and $R_3$ to $R_{10}$ is a binding site to A2 in Formula 1; and in Formula 2B, $X_2$ is N, $X_1$ is C($R_1$), $X_3$ is C($R_3$), $X_4$ is C($R_4$), $X_6$ is C($R_6$), $X_7$ is C($R_7$), $X_8$ is C($R_8$), $X_9$ is C($R_9$), and at least one selected from $R_1$, $R_3$, $R_4$, and $R_6$ to $R_9$ is a binding site to A2 in Formula 1.

4. The heterocyclic compound as claimed in claim 1, wherein:

in Formula 2A, $X_3$ is N, $X_1$ is C($R_1$), $X_2$ is C($R_2$), $X_4$ is C($R_4$), $X_5$ is C($R_5$), $X_6$ is C($R_6$), $X_7$ is C($R_7$), $X_8$ is C($R_8$), $X_9$ is C($R_9$), and $X_{10}$ is C($R_{10}$), and at least one selected from $R_1$, $R_2$, and $R_4$ to $R_{10}$ is a binding site to A2 in Formula 1; and in Formula 2B, $X_3$ is N, $X_1$ is C($R_1$), $X_2$ is C($R_2$), $X_4$ is C($R_4$), $X_6$ is C($R_6$), $X_7$ is C($R_7$), $X_8$ is C($R_8$), and $X_9$ is C($R_9$), and at least one selected from $R_1$, $R_2$, $R_4$, and $R_6$ to $R_9$ is a binding site to A2 in Formula 1.

5. The heterocyclic compound as claimed in claim 1, wherein in Formula 2A, $X_1$ and $X_3$ are each N, $X_2$ is C($R_2$), $X_4$ is C($R_4$), $X_5$ is C($R_5$), $X_6$ is C($R_6$), $X_7$ is C($R_7$), $X_8$ is C($R_8$), $X_9$ is C($R_9$), and $X_{10}$ is C($R_{10}$), and at least one selected from $R_2$, $R_4$ and $R_5$ to $R_{10}$ is a binding site to A2 in Formula 1; and in Formula 2B, $X_1$ and $X_3$ is N, $X_2$ is C($R_2$), $X_4$ is C($R_4$), $X_6$ is C($R_6$), $X_7$ is C($R_7$), $X_8$ is C($R_8$), and $X_9$ is C($R_9$), and at least one from $R_2$, $R_4$ and $R_6$ to $R_9$ is a binding site to A2 in Formula 1.

6. The heterocyclic compound as claimed in claim 1, wherein in Formula 2A, $X_1$ and $X_6$ is N, $X_2$ is C($R_2$), $X_3$ is C($R_3$), $X_4$ is C($R_4$), $X_5$ is C($R_5$), $X_7$ is C($R_7$), $X_8$ is C($R_8$), $X_9$ is C($R_9$), and $X_{10}$ is C($R_{10}$), and at least one selected from $R_2$ to $R_5$ and $R_7$ to $R_{10}$ is a binding site to A2 in Formula 1, and in Formula 2B, $X_1$ and $X_6$ is N, $X_2$ is C($R_2$), $X_3$ is C($R_3$), $X_4$ is C($R_4$), $X_7$ is C($R_7$), $X_8$ is C($R_8$), and $X_9$ is C($R_9$), and at least one selected from $R_2$ to $R_4$ and $R_7$ to $R_9$ is a binding site to A2 in Formula 1.

7. The heterocyclic compound as claimed in claim 1, wherein:

$A_1$ is a group represented by Formula 2A, in Formula 2A, $X_1$, $X_3$ and $X_5$ is N, $X_2$ is C($R_2$), $X_4$ is C($R_4$), $X_6$ is C($R_6$), $X_7$ is C($R_7$), $X_8$ is C($R_8$), $X_9$ is C($R_9$), and $X_{10}$ is C($R_{10}$), and at least one selected from $R_2$, $R_4$ and $R_6$ to $R_{10}$ is a binding site to A2 in Formula 1.

8. The heterocyclic compound as claimed in claim 1, wherein n2 is an integer from 1 to 3.

9. The heterocyclic compound as claimed in claim 1, wherein $R_1$ to $R_{10}$ are each independently selected from:

a binding site to A2 in Formula 1;

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, and a hydrazono group; and —Si($Q_1$)($Q_2$)($Q_3$), wherein $R_1$ to $R_{10}$ are separate or are linked to form a substituted or unsubstituted condensed ring, and $Q_1$ to $Q_3$ are each independently selected from a $C_1$-$C_{10}$ alkyl group, a $C_1$-$C_{10}$ alkoxy group, a phenyl group, and a naphthyl group.

10. The heterocyclic compound as claimed in claim 1, wherein:

a in Formula 3 is an integer of 1 to 3, and

L in Formula 3 is selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a dihydroacridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a dihydroacridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

11. The heterocyclic compound as claimed in claim 1, wherein:
a is an integer of 1 to 3, and
L is a group represented by one of Formulae 4-1 to 4-22 and 4-25 to 4-27:
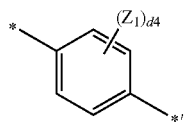
Formula 4-1
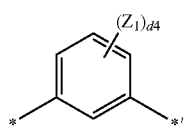
Formula 4-2
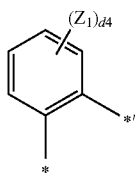
Formula 4-3
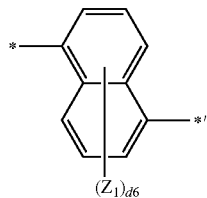
Formula 4-4
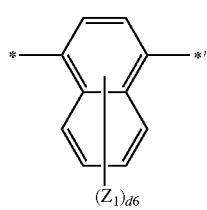
Formula 4-5
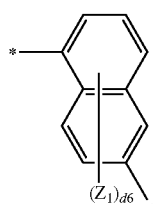
Formula 4-6
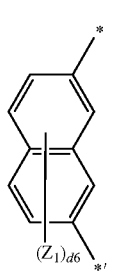
Formula 4-7
-continued
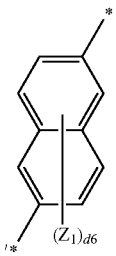
Formula 4-8
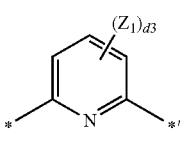
Formula 4-9
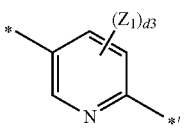
Formula 4-10
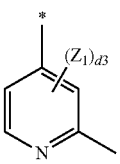
Formula 4-11
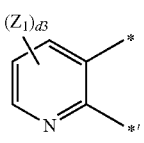
Formula 4-12
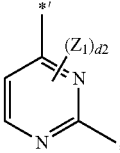
Formula 4-13
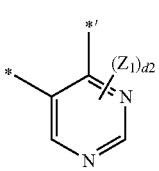
Formula 4-14
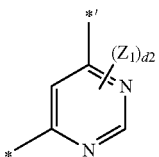
Formula 4-15
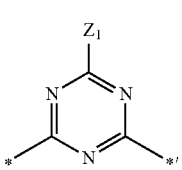
Formula 4-16

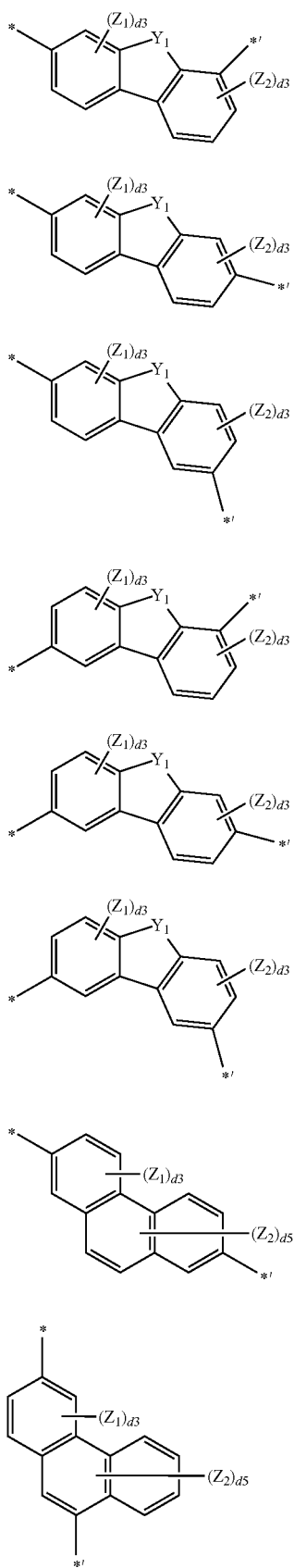

Formula 4-17
Formula 4-18
Formula 4-19
Formula 4-20
Formula 4-21
Formula 4-22
Formula 4-25
Formula 4-26

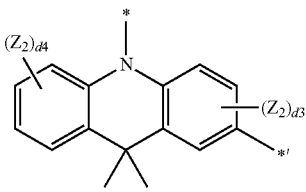

Formula 4-27 wherein, in Formulae 4-17 to 4-22,
$Y_1$ is O, S, $C(Z_3)(Z_4)$, or $Si(Z_6)(Z_7)$,
wherein, in Formulae 4-1 to 4-16 and 4-25 to 4-27,
$Y_1$ is O, S, $C(Z_3)(Z_4)$, $N(Z_5)$, or $Si(Z_6)(Z_7)$,
$Z_1$ to $Z_4$, $Z_6$ and $Z_7$ are each independently selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$, wherein $Q_{31}$ to $Q_{33}$ are each independently selected from a $C_1$-$C_{10}$ alkyl group, a $C_1$-$C_{10}$ alkoxy group, a phenyl group, and a naphthyl group,
d2 is an integer from 0 to 2,
d3 is an integer from 0 to 3,
d4 is an integer from 0 to 4,
d5 is an integer from 0 to 5,
d6 is an integer from 0 to 6,
d8 is an integer from 0 to 8, and
* and *' are each a binding site to a neighboring atom.

12. The heterocyclic compound as claimed in claim 11, wherein:
   L is a group represented by one of Formulae 4-1, 4-2, and 4-27, and
   $Z_1$ and $Z_2$ in Formulae 4-1, 4-2, and 4-27 are each independently be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$),
   wherein $Q_{31}$ to $Q_{33}$ are each independently selected from a $C_1$-$C_{10}$ alkyl group, a $C_1$-$C_{10}$ alkoxy group, a phenyl group, and a naphthyl group.

13. The heterocyclic compound as claimed in claim 1, wherein a is 0 or 1.

14. The heterocyclic compound as claimed in claim 1, Ar is a group represented by one of Formulae 5-1 to 5-8, Formula 6-13 to 6-16, 6-37 to 6-39, 6-48, and 6-50 to 6-55.

15. The heterocyclic compound as claimed in claim 1, wherein b is an integer from 1 to 3.

16. A heterocyclic compound, wherein the heterocyclic compound is one of Compounds 1 to 102:

1

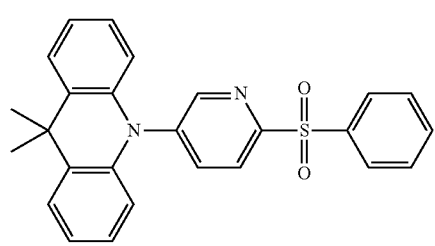

2

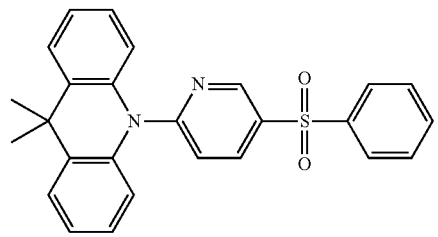

3

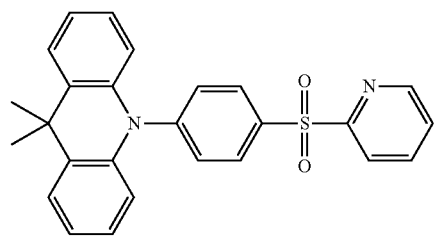

4

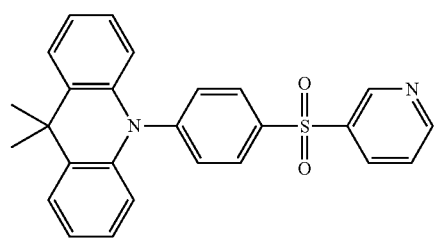

5

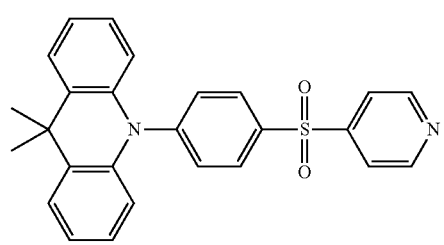

11

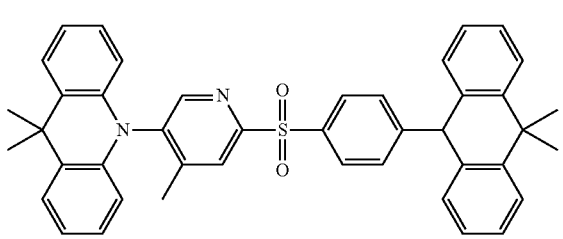

12

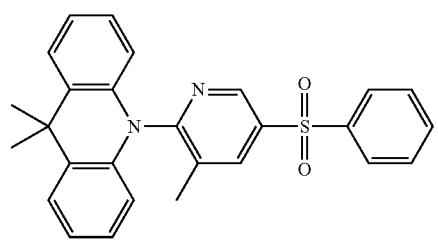

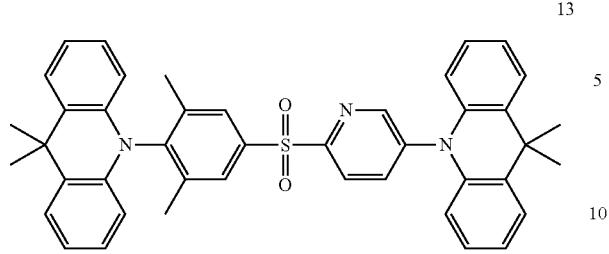
13
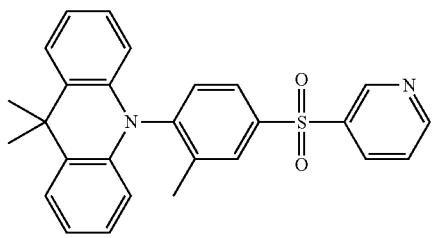
19
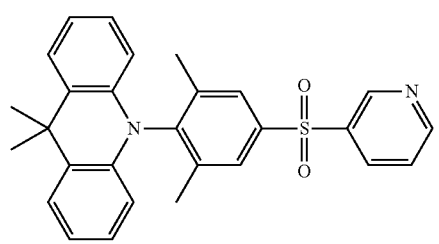
14
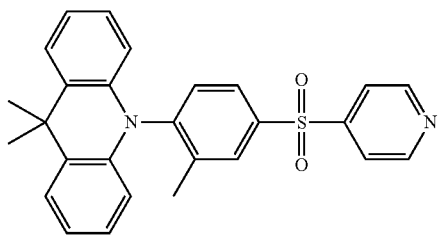
20
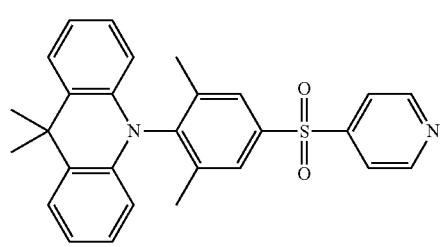
15
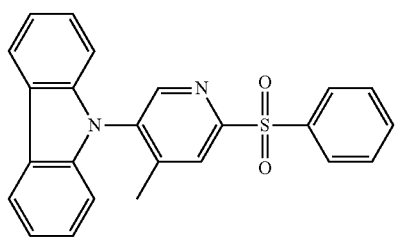
21
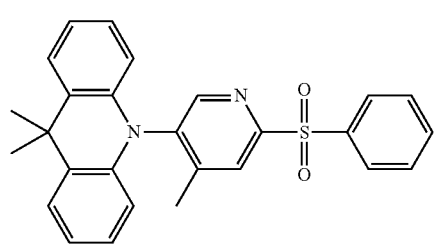
16
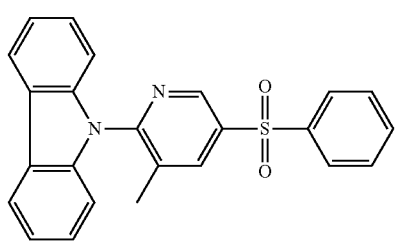
22
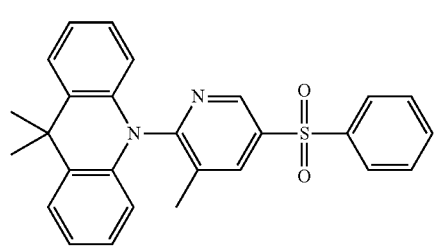
17
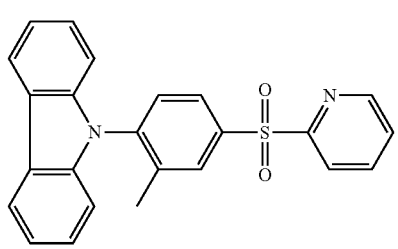
23
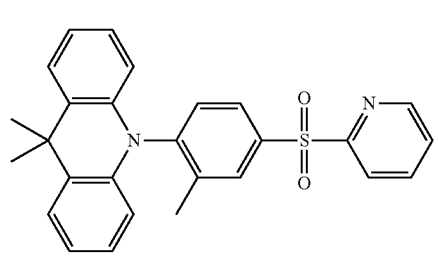
18
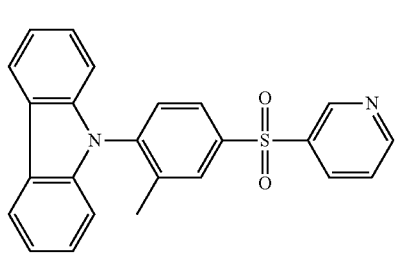
24

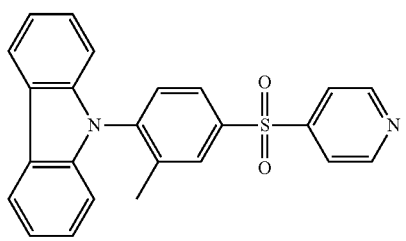
25
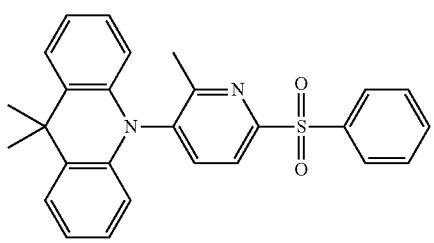
26
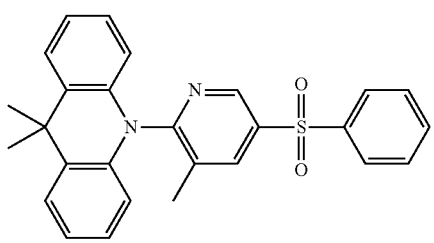
27
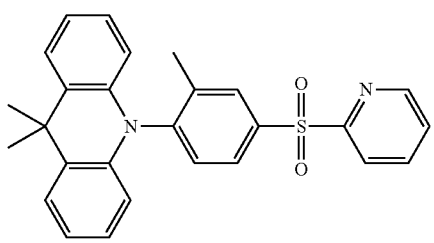
28
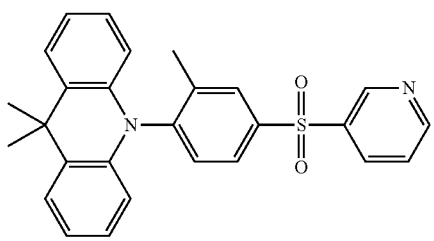
29
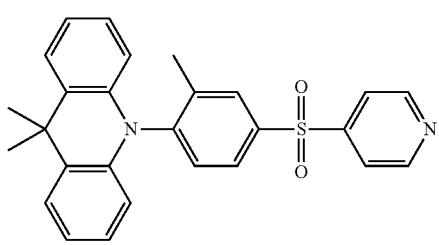
30
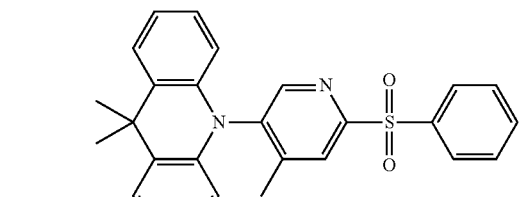
31
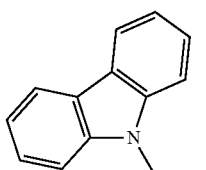
32
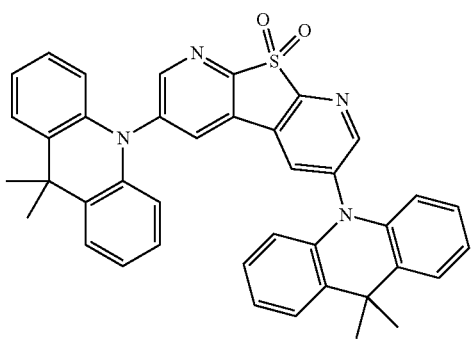
33
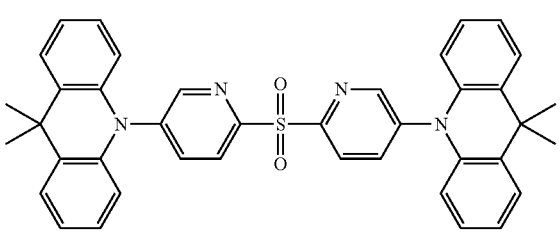
34

181
-continued
35
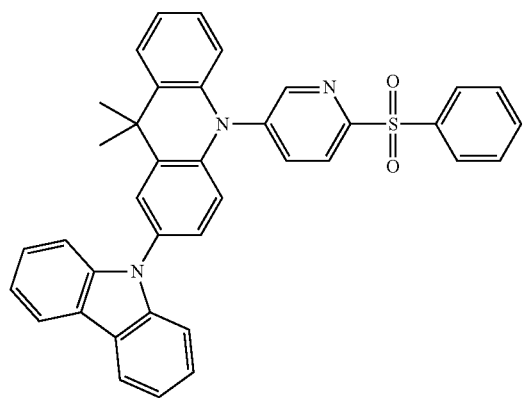
36
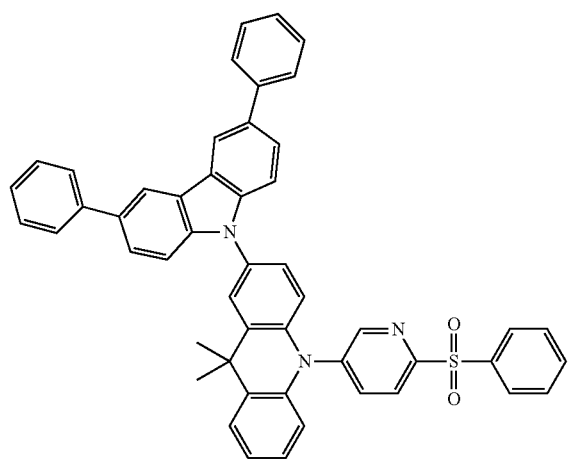
37
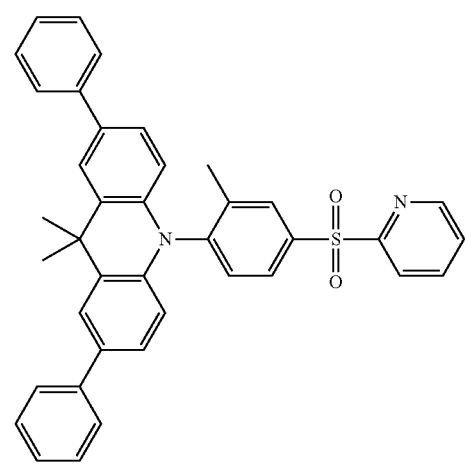
182
-continued
38
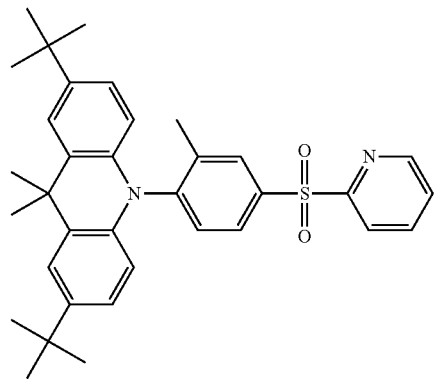
39
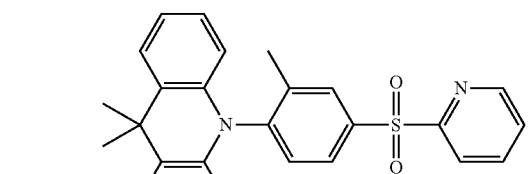
40
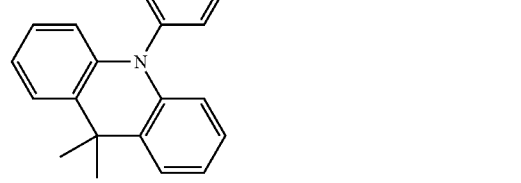
41
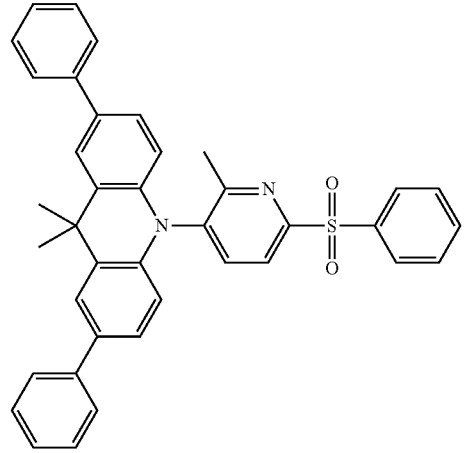

-continued
42
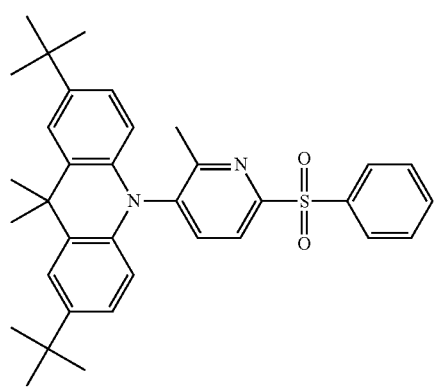
43
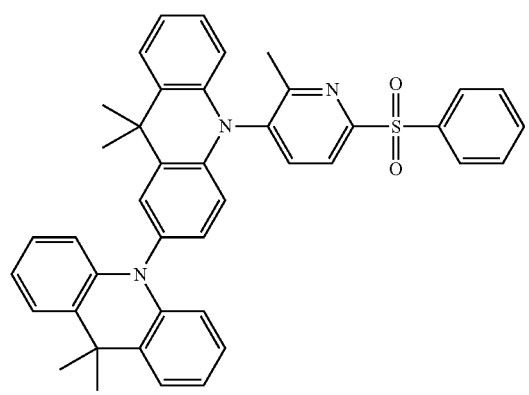
44
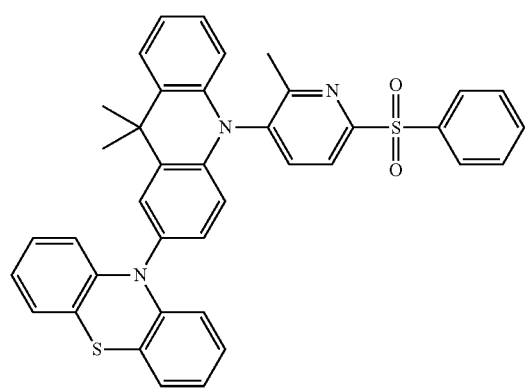
45
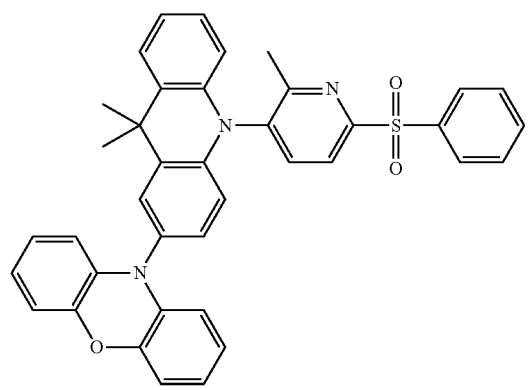
-continued
46
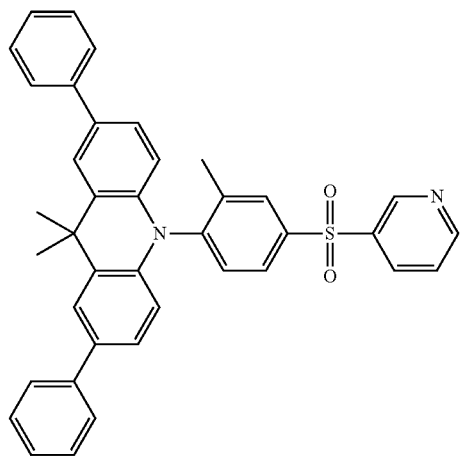
47
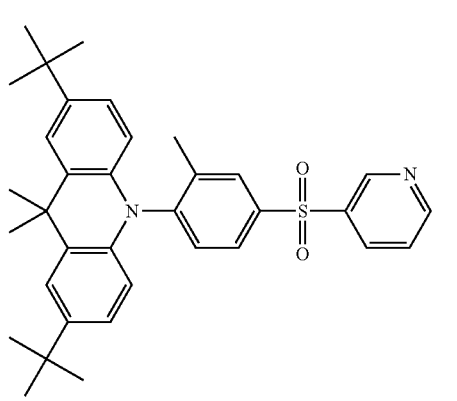
48
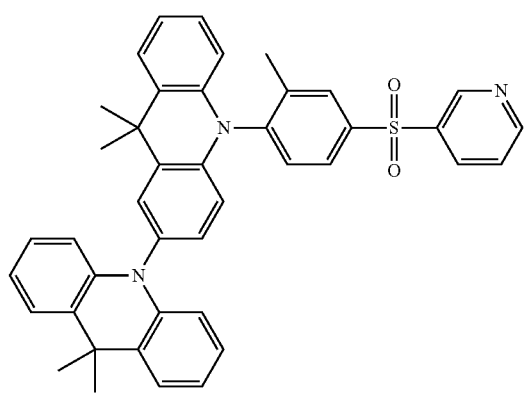
49
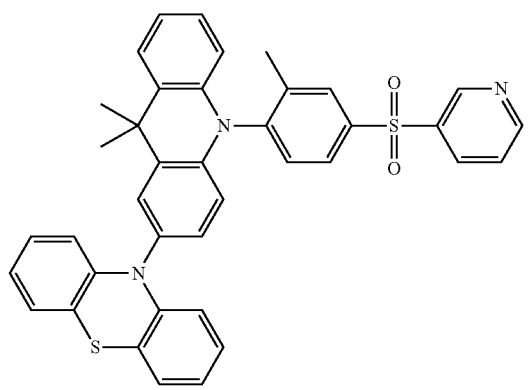

-continued
50
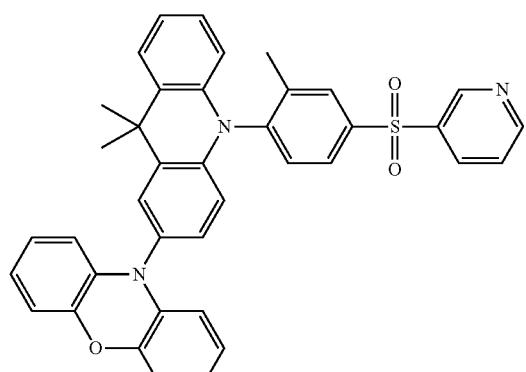
51
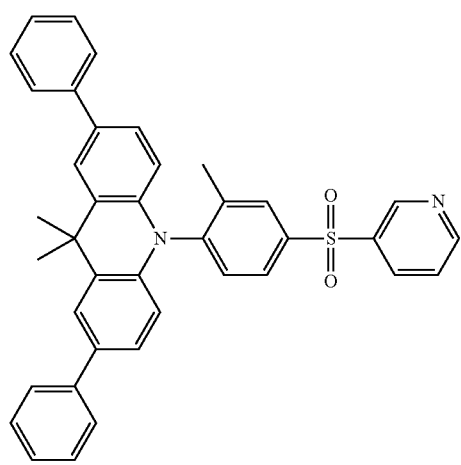
52
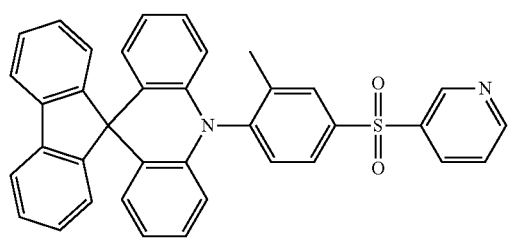
53
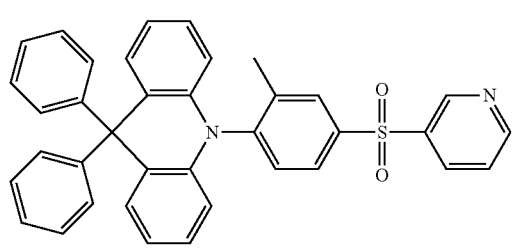
-continued
54
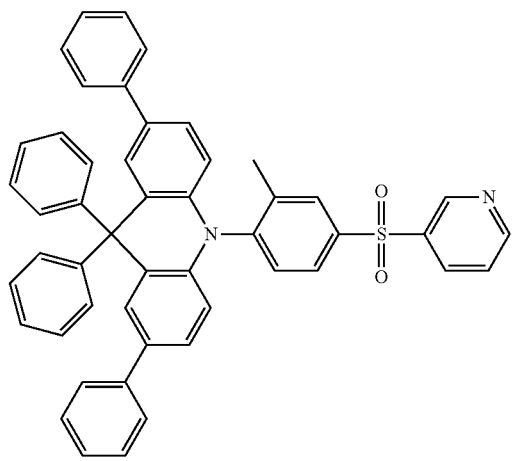
55
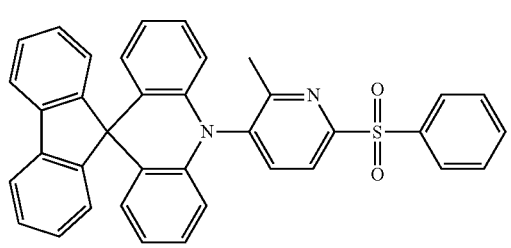
56
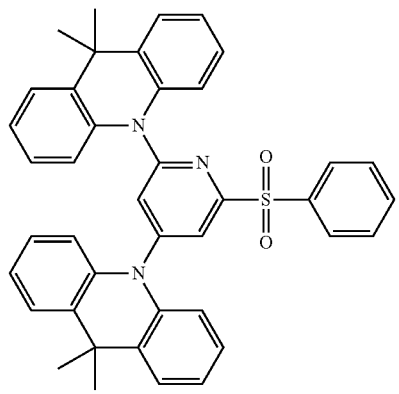
57
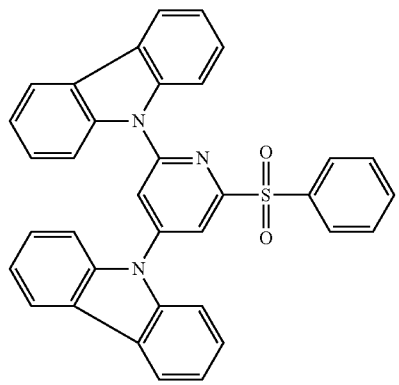

58
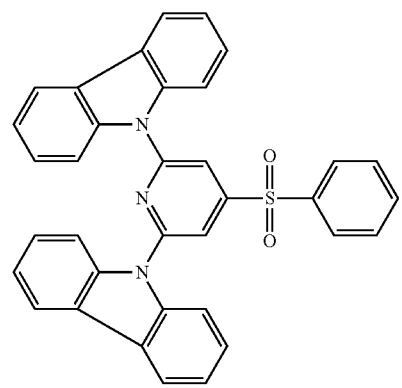
59
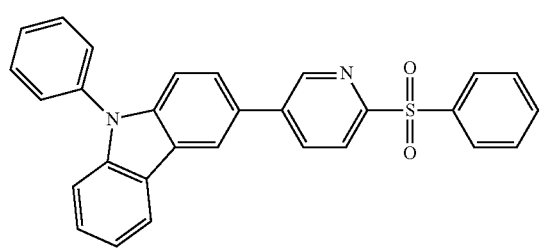
60
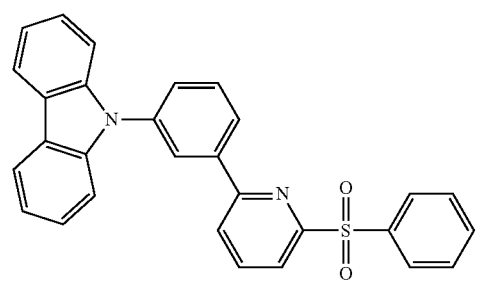
61
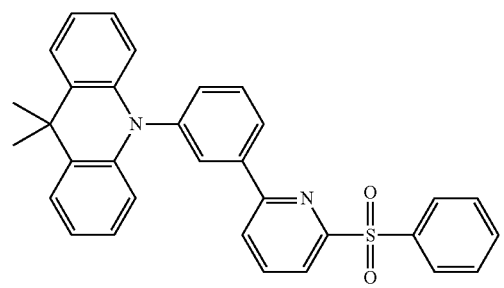
62
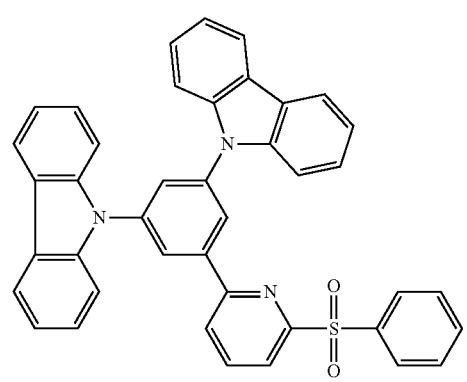
63
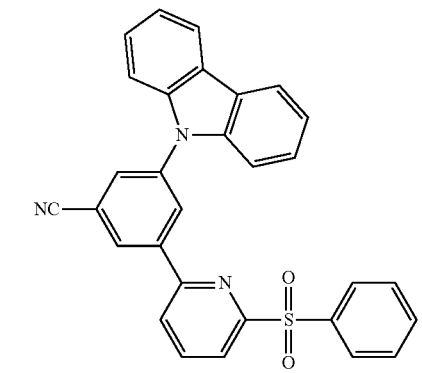
64
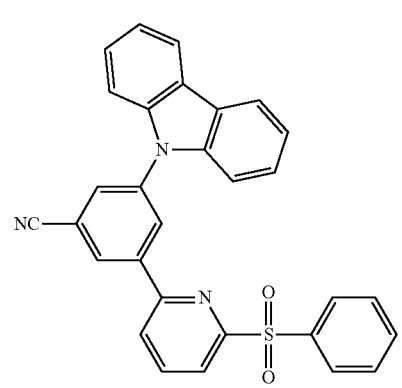
65
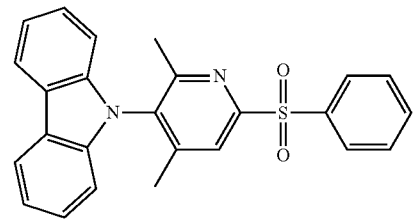
66
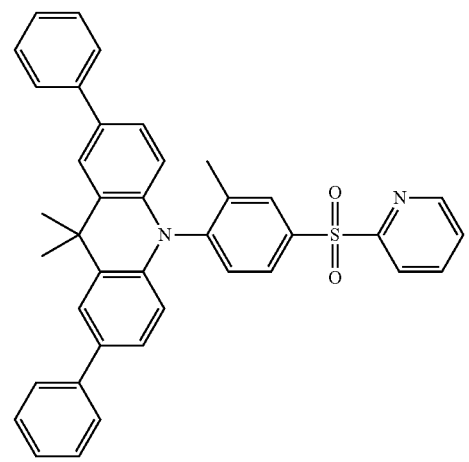

67
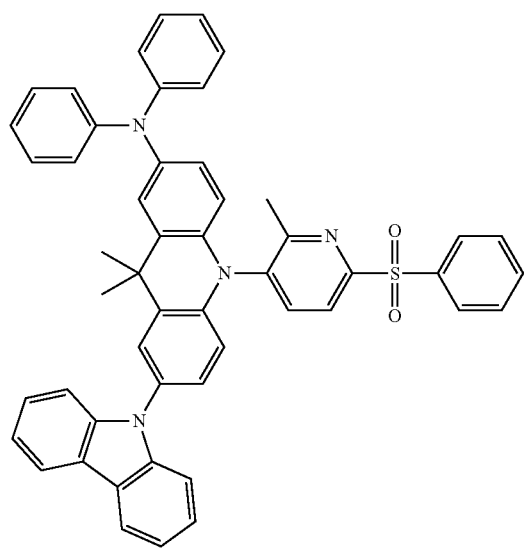
68
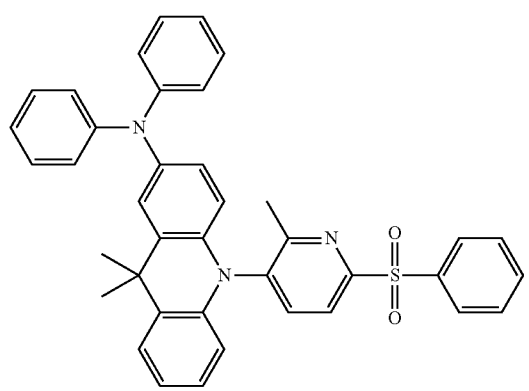
69
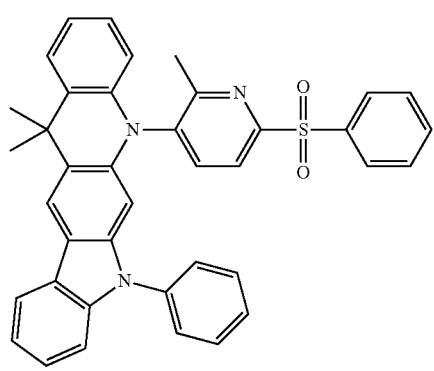
70
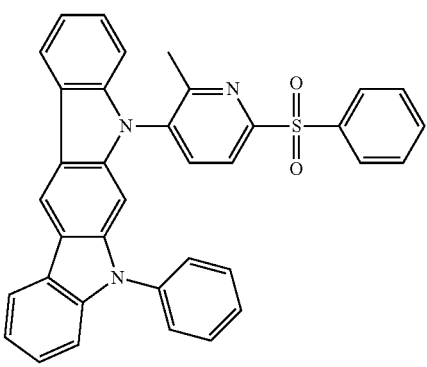
71
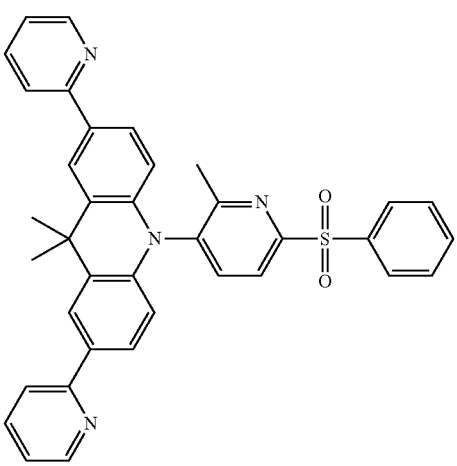
72
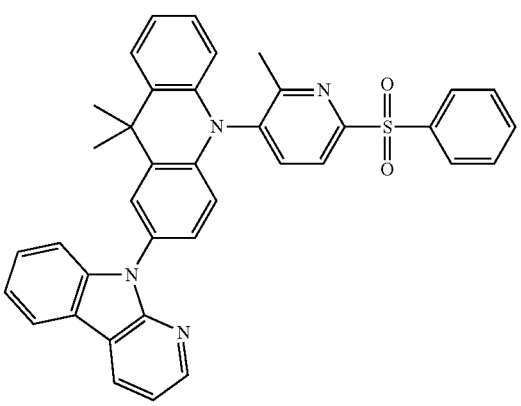

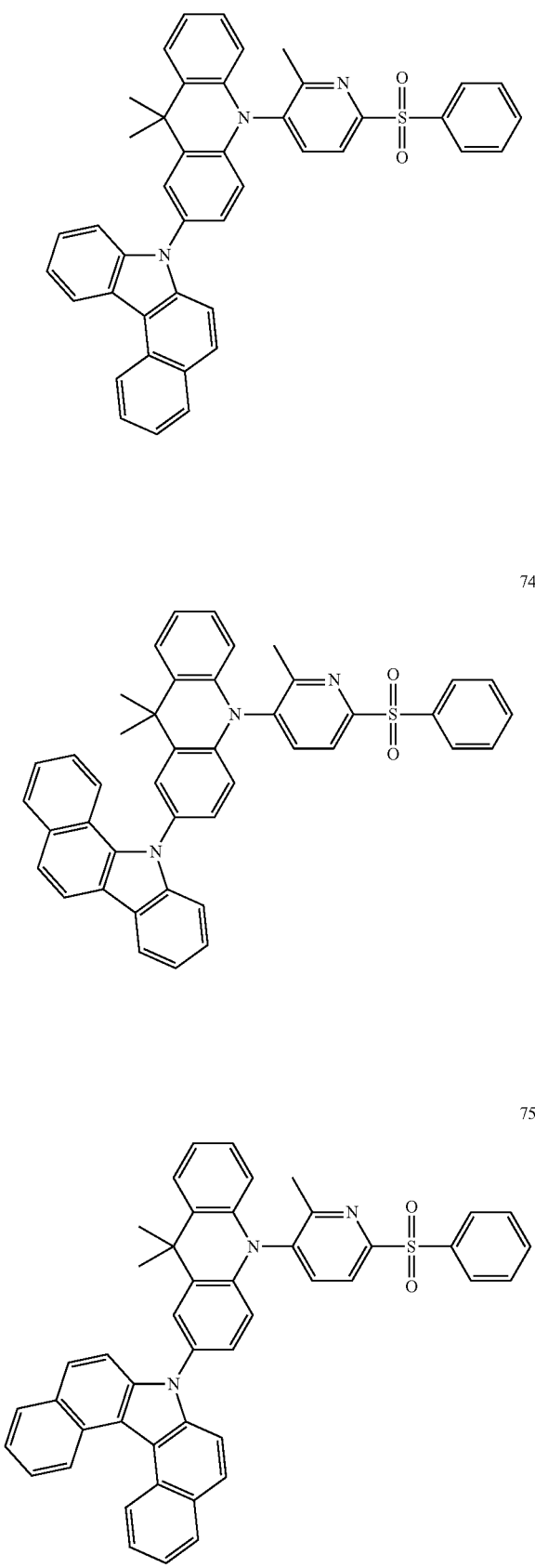
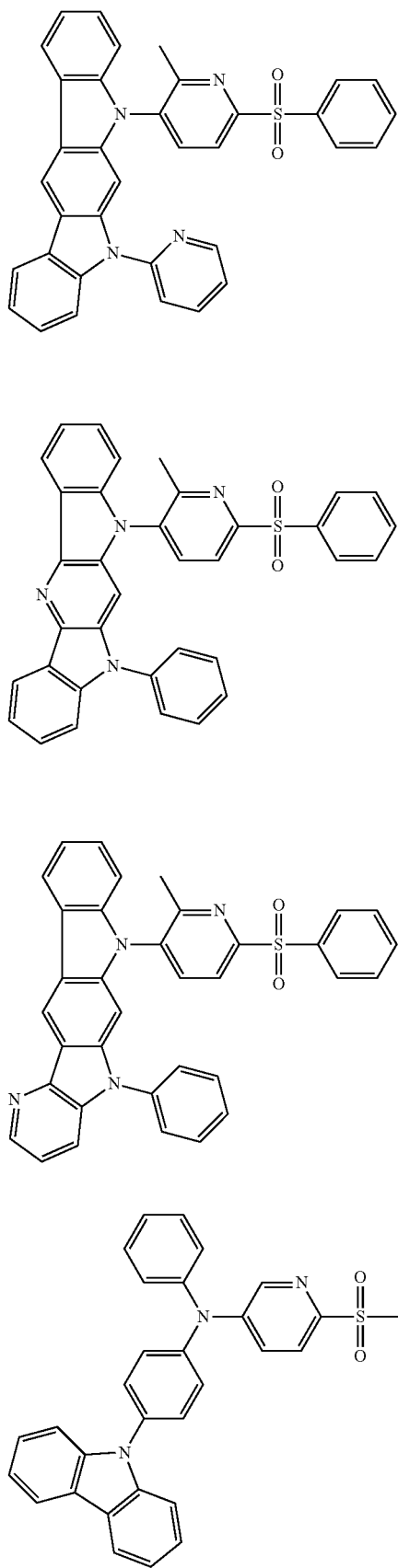

79
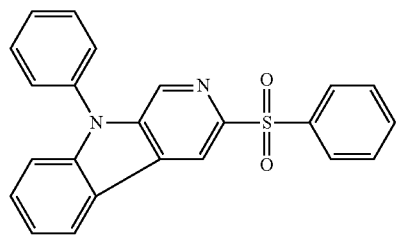
80
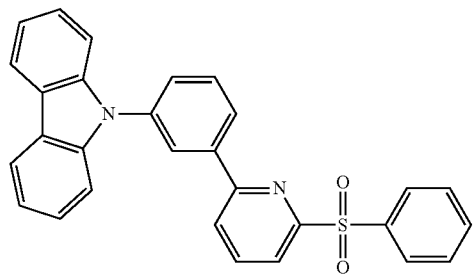
81
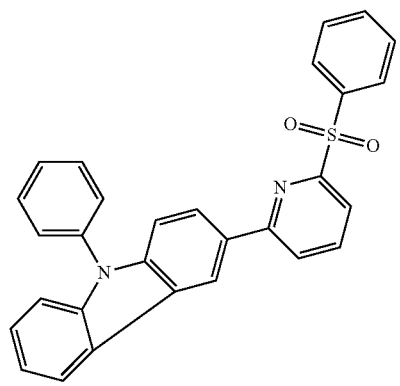
82
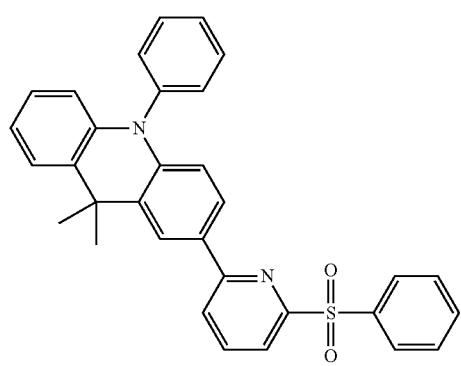
83
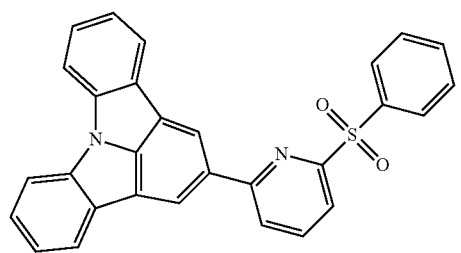
84
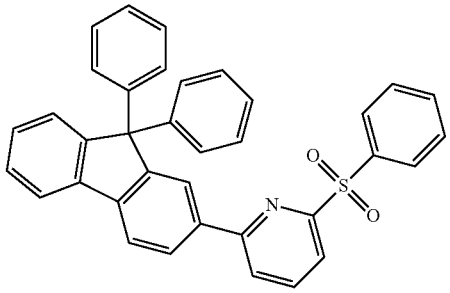
85
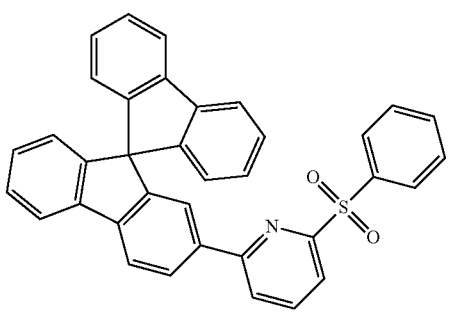
86
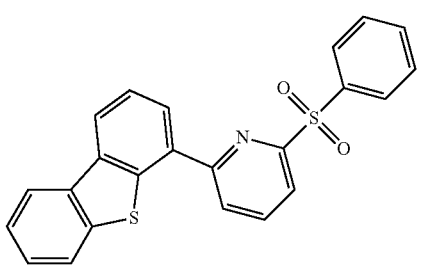
87
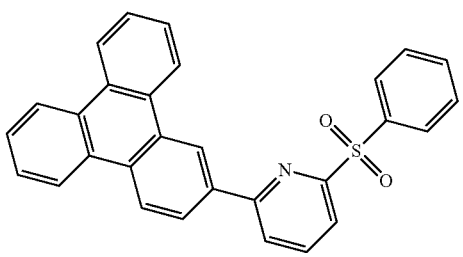
88
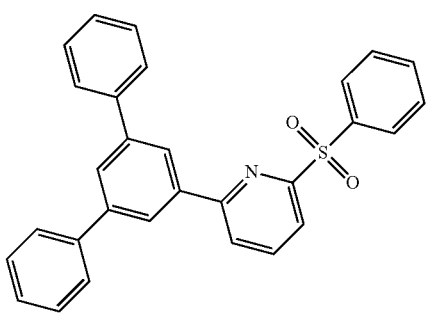

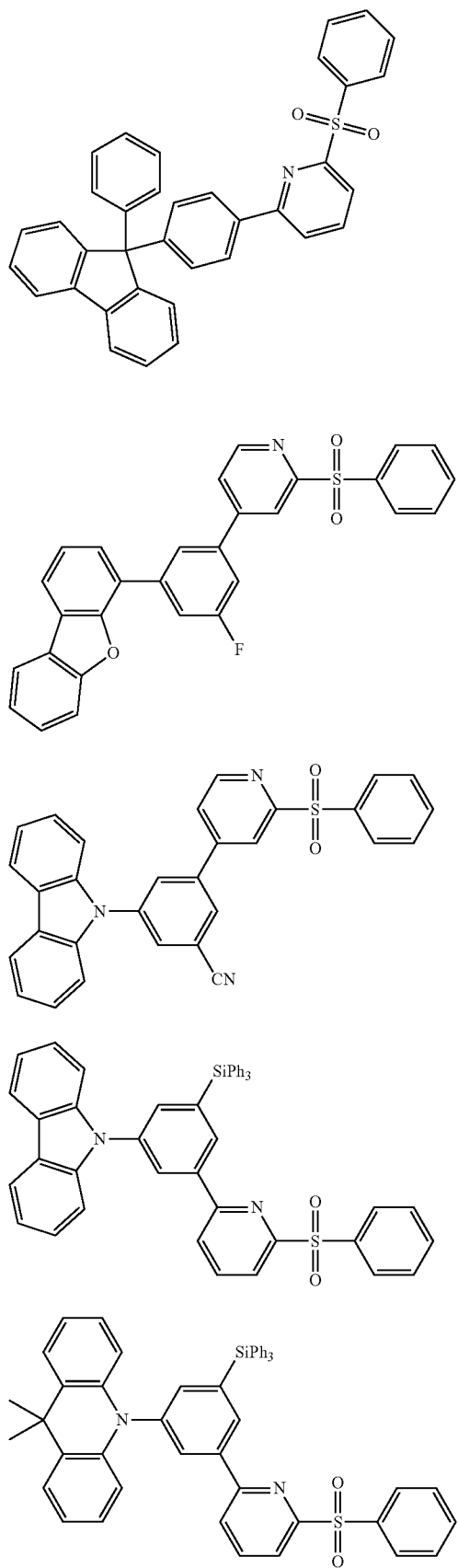

-continued

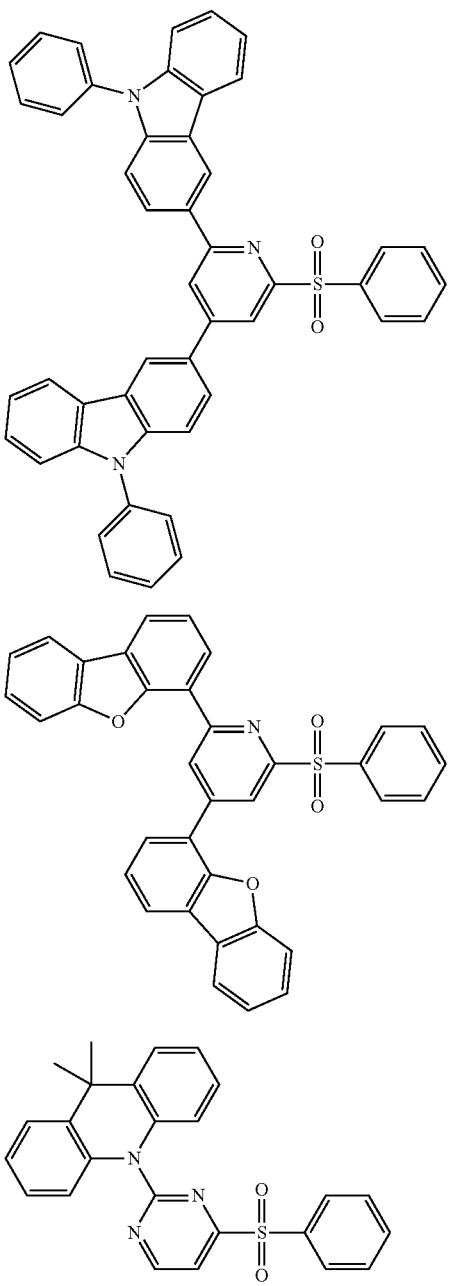

-continued

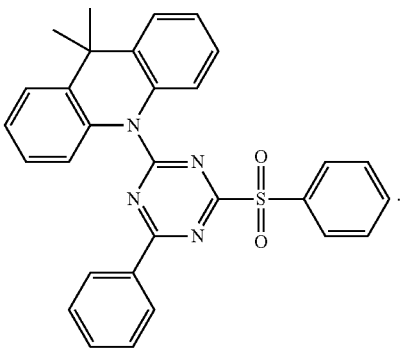

17. An organic light-emitting device comprising:
    a first electrode;
    a second electrode facing the first electrode; and
    an organic layer between the first electrode and the second electrode, the organic layer comprising an emission layer,
    wherein the organic layer includes the heterocyclic compound as claimed in claim 1.

18. The organic light-emitting device as claimed in claim 17, wherein:
    the emission layer includes a host and a dopant, and
    the host or the dopant includes the heterocyclic compound.

19. An organic light-emitting device comprising:
    a first electrode;
    a second electrode facing the first electrode; and
    an organic layer between the first electrode and the second electrode, the organic layer comprising an emission layer,
    wherein the organic layer includes the heterocyclic compound as claimed in claim 16.

20. The organic light-emitting device as claimed in claim 19, wherein:
    the emission layer includes a host and a dopant, and
    the host or the dopant includes the heterocyclic compound.

* * * * *